(12) United States Patent
Wolffe et al.

(10) Patent No.: US 6,919,204 B2
(45) Date of Patent: Jul. 19, 2005

(54) MODULATION OF GENE EXPRESSION USING LOCALIZATION DOMAINS

(75) Inventors: Alan P. Wolffe, deceased, late of Orinda, CA (US); by Elizabeth J. Wolffe, legal representative, Orinda, CA (US); Fyodor Urnov, Richmond, CA (US); Albert Lai, Richmond, CA (US); Eva Raschke, Berkeley, CA (US)

(73) Assignee: Sangamo Biosciences, Inc., Richmond, CA (US)

(*) Notice: Subject to any disclaimer, the term of this patent is extended or adjusted under 35 U.S.C. 154(b) by 86 days.

(21) Appl. No.: 09/967,869

(22) Filed: Sep. 28, 2001

(65) Prior Publication Data

US 2003/0082552 A1 May 1, 2003

Related U.S. Application Data

(60) Provisional application No. 60/236,884, filed on Sep. 29, 2000.

(51) Int. Cl.[7] .............................. C12N 5/02; C12N 15/63

(52) U.S. Cl. ....................................... 435/375; 435/455

(58) Field of Search .................................. 435/375, 455

(56) References Cited

U.S. PATENT DOCUMENTS

| 6,534,261 B1 | 3/2003 | Cox, III et al. |
| 6,607,882 B1 | 8/2003 | Cox, III et al. |
| 2002/0160940 A1 | 10/2002 | Case et al. |

FOREIGN PATENT DOCUMENTS

| WO | WO 97/11972 | 4/1997 |
| WO | WO 00/41566 | 7/2000 |
| WO | WO 00/42219 | 7/2000 |
| WO | WO 01/30843 | 5/2001 |
| WO | WO 01/83793 | 11/2001 |

OTHER PUBLICATIONS

Tweedie et al, Nature Genetics, Dec., 1999, vol. 23: pp. 389–390.*
Amir et al., "Rett Syndrome is Caused by Mutations in X–Lined *MECP2*, Encoding Methyl–CpG–Binding Protein 2," *Nature Genet.* 23:185–188 (1999).
Ashburner, Puffing Patterns in *Drosophila Melangogaster* and Related Species, *Results Probl. Cell Differ.* 4:101–151 (1972).
Bird, "Does DNA Methylation Control Transposition of Selfish Elements in the Germline?," *Trend Genet.* 13:469–472 (1997).
Bird et al., "Gene Number, Noise Reduction and Biological Complexity," *Trend Genet.* 11:94–99 (1995).
Bird and Wolffe, "Methylation–Induced Repression–Belts, Braces, and Chromatin," *Cell* 99:451–454 (1999).

Boeke et al., "The Minimal Repression Domain of MBD2b Overlaps with the Methyl–CpG–Bindign Domain and Binds Directly to Sin3A," *Journal of Biological Chemistry* 275(45):34963–34967 (2000).
Buschhausen et al., "Chromatin Structure is Required to Block Transcription of the Methylated Herpes Simplex Virus Thymidine Kinase Gene," *PNAS USA* 84:1177–1181 (1987).
Cao et al., "Conserved Plant Genes With Similarity to Mammalian de novo DNA Methyltransferases," *PNAS USA* 97:4979–4984 (2000).
Colot et al., "Eukaryotic DNA Methylation as an Evolutionary Device," *BioEssays* 21:402–411 (1999).
Cross et al., "Purification of CpG Islands Using a Methylated DNA Binding Column," *Nature Genetics* 6(3):236–244 (1994).
Grunstein et al., "Histone Acetylation in Chromatin Structure and Transcription," *Nature* 389:349–352 (1997).
Heard et al., "X–Chromosome Inactivation in Mammals," *Annual Rev. Gent.* 31:571–610 (1997).
Iguchi–Arigan et al., "CpG Methylation of the cAMP–Responsive Enhancer/Promoter Sequence TGACGTCA Abolishes Specific Factor Binding as Well as Transcriptional Activation," *Genes & Development* 3:612–619 (1989).
Kaludov and Wolffe, "MeCP2 Driven Transcriptional Repression In Vitro: Selectivity for Methylated DNA, Action at a Distance and Contacts with the Basal Transcription Machinery," *Nucleic Acids Research* 28(9):1921–1928 (2000).
Kass et al., "DNA Methylation Directs a Time–Dependent Repression of Transcription Initiation," *Current Biol.* 7:157–165 (1997).
Kremer et al., "Mapping of DNA Instability at the Fragile X to Trinucleotide Repeat Sequence p(CCG)n," *Science* 252:1711–1714 (1991).
Lei et al., "De novo DNA Cytosine Methyltransferase Activities in Mouse Embryonic Stem Cells," *Development* 122:3195–3205 (1996).
Li et al., "Targeted Mutation of the DNA Methyltransferase Gene Results in Embryonic Lethality," *Cell* 69:915–926 (1992).
Mannervik et al., "Transcriptional Coregulators in Development," *Science* 284:606–609 (1999).
Meehan et al., "Characterization of MeCP2, a Vertebrate DNA Binding Protein with Affinity for Methylated DNA," *Nucleic Acids Res.* 20:5085–5092 (1992).

(Continued)

*Primary Examiner*—Terry McKelvey
(74) *Attorney, Agent, or Firm*—Robins & Pasternak LLP; Sean M. Brennan

(57) ABSTRACT

Methods and compositions for regulating gene expression are provided. In particular, methods and compositions comprising localization domains, and fusions of localization domains with DNA binding domains and, optionally regulatory domains, are provided.

32 Claims, 9 Drawing Sheets

OTHER PUBLICATIONS

Nan et al., "MeCP2 is a Transcriptional Repressor With Abundant Binding Sites in Genomic Chromatin," *Cell* 88(4):471–481 (1997).

Ohki et al., "Solution Structure of the Methyl–CpG–Binding Domain of the Methylation–Dependent Transcriptional Respressor MBD1," *The EMBO J.* 18:(23):6653–6661 (1999).

Okano et al., "DNA Methyltransferases Dnmt3a and Dnmt3b Are Essential for De Novo Methylation and Mammalian Development," *Cell* 99:247–257 (1999).

Okano et al., "Cloning and Characterization of a Family of Novel Mammalian DNA (cytosine–5) Methyltransferases," *Nature Genet.* 19:219–220 (1998).

Siegfried et al., "DNA Methylation: A Molecular Lock," *Curr. Biol.* 7:R305–307 (1997).

Steinbach et al., "Somatic Linker Histones Cause Loss of Mesodermal Competence in *Xenopus*," *Nature* 389:395–399 (1997).

Van Steensel et al., "Identification of In Vivo DNA Trargets of Chromatin Proteins Using Tethered Dam Methyltransferase," *Nature Biotechnology* 18(4):424–428 (2000).

Wakefield et al., "The Solution Structure of the Domin From MeCP2 That Binds to Methylated DNA," *J. Mol. Biol.* 291:1055–1065 (1999).

Wolffe et al., "Co–Repressor Complexes and Remodeling Chromatin for Repression," *Biochemical Society Transactions* 28(4):379–386 (2000).

Xu et al., "Chromosome Instability and Immunodeficiency Syndrome Caused by Mutations in a DNA Methyltransferase Gene," *Nature* 402:187–189 (1999).

Yoder et al., "Cytosine Methylation and the Ecology of Intragenomic Parasites," *Trend Genet.* 13:335–340 (1997).

\* cited by examiner

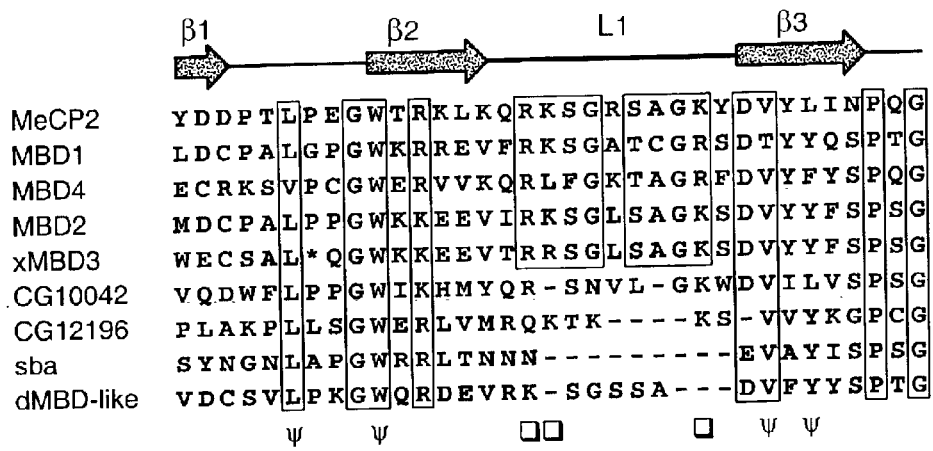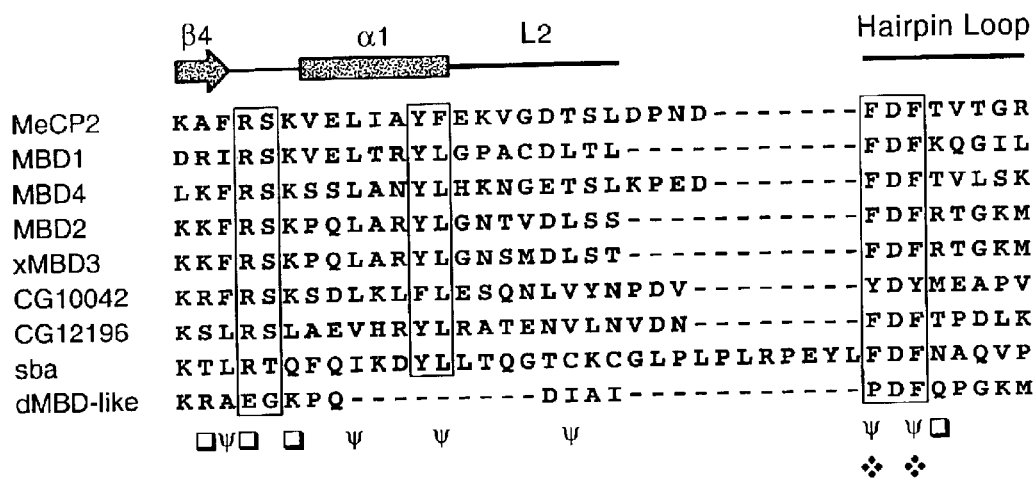
FIG._1A

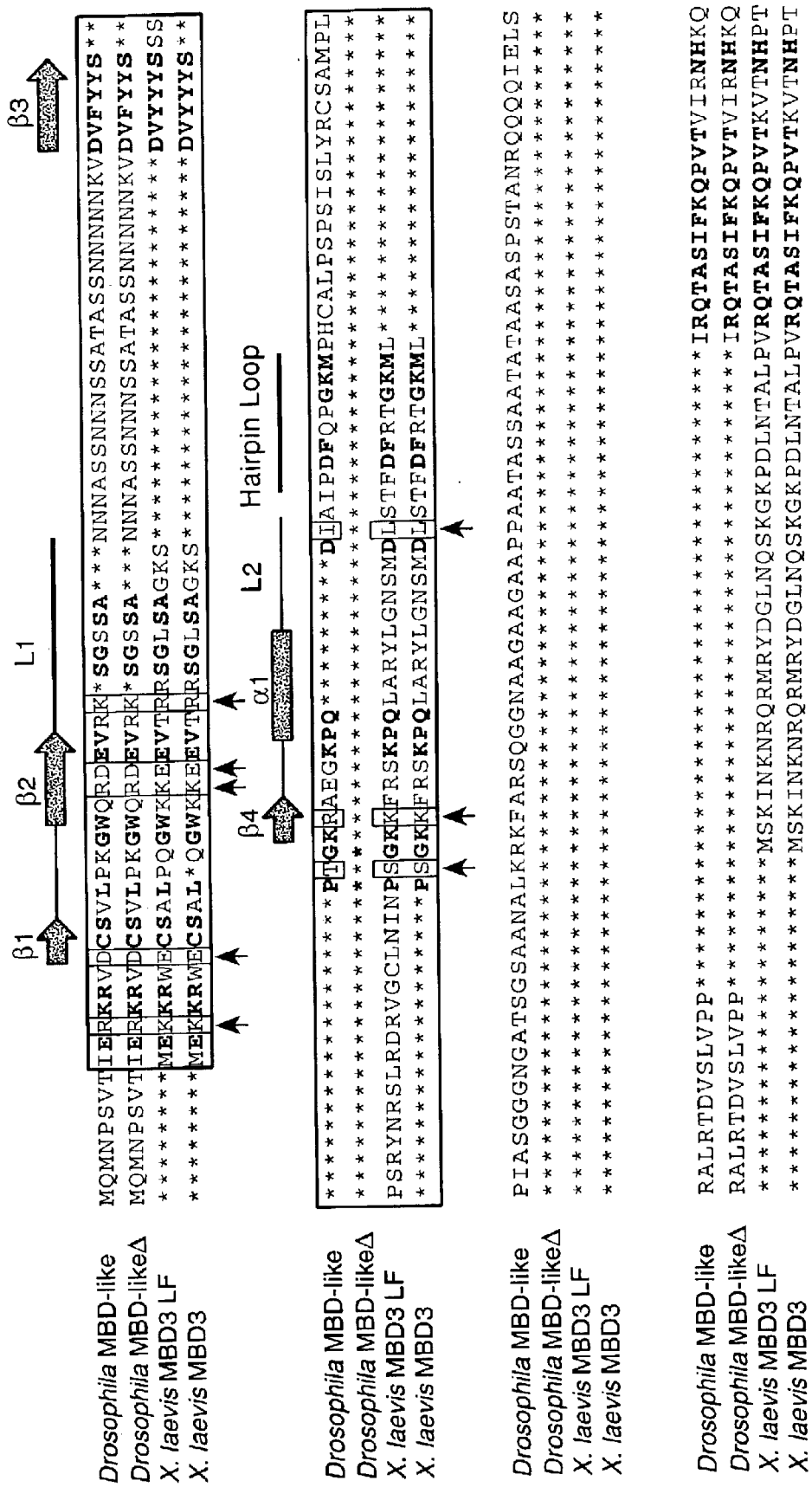
FIG. _1B-1

```
Drosophila MBD-like      DPAKAKNEPKHGTREKPKQLFWEKRLERLRACHDSGEELDDISLPKTIRTVGPNVNEQTVLQSVATALH*
Drosophila MBD-likeΔ     DPAKAKNEPKHGTREKPKQLFWEKRLERLRACHDSGEELDDISLPKTIRTVGPNVNEQTVLQSVATALH*
X. laevis MBD3 LF        **NKVKSDP*QKAVDQPRQLFWEKKLSGLNAFDIAEELVKTMELPKGLQGVGPGCTDETLLSAIASALHT
X. laevis MBD3           **NKVKSDP*QKAVDQPRQLFWEKKLSGLNAFDIAEELVKTMELPKGLQGVGPGCTDETLLSAIASALHT Drosophila MBD-like      *MLNAGVHGQSSTKADLTKNAMAFMNPE**********************QPLMHAVIISEDDIRKQE
Drosophila MBD-likeΔ     *MLNAGVHGQSSTKADLTKNAMAFMNPE**********************QPLMHAVIISEDDIRKQE
X. laevis MBD3 LF        STM*********************************PITGQLSAAVEKNPGVWLNTSQPLCKAFMVTDEDDIRKQE
X. laevis MBD3           STM*********************************PITGQLSAAVEKNPGVWLNTSQPLCKAFMVTDEDDIRKQE Drosophila MBD-like      DRVGVARRKLQDALKT
Drosophila MBD-likeΔ     DRVGVARRKLQDALKT
X. laevis MBD3 LF        ELVQQVRKKLEEALMADMLAHVEEISKDGGAPLDKDIDDEEEDQDPREQEADDV
X. laevis MBD3           ELVQQVRKKLEEALMADMLAHVEEISKDGGAPLDKDIDDEEEDQDPREQEADDV
```

*FIG._1B-2*

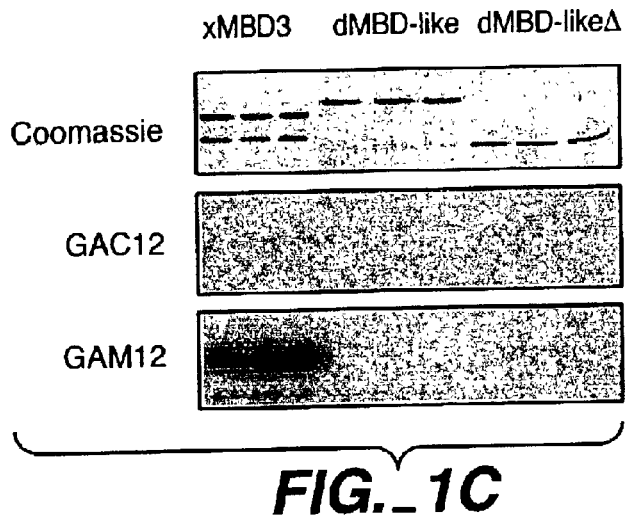
FIG._1C
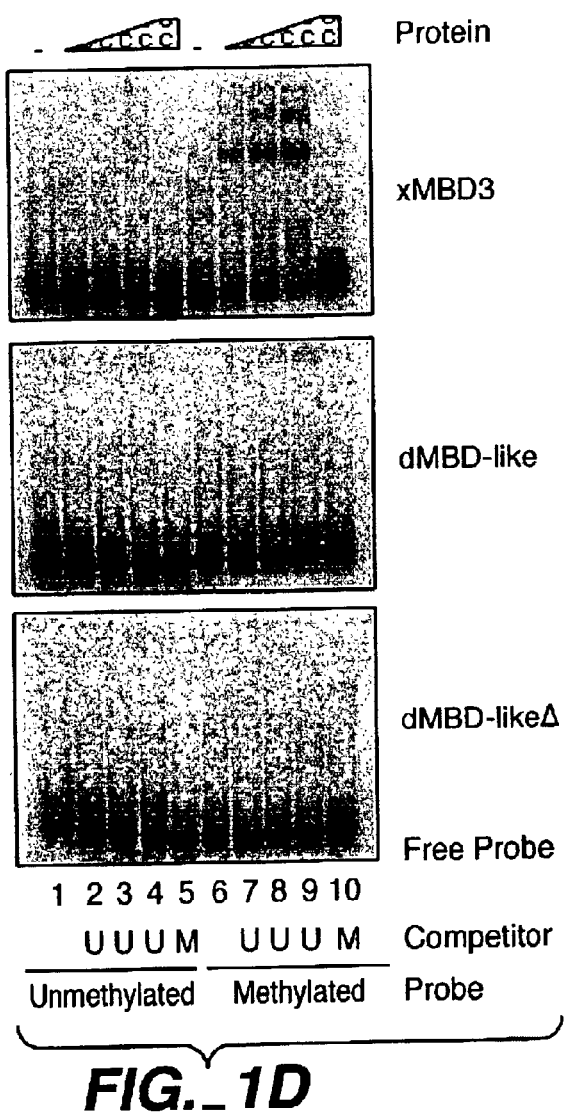
FIG._1D

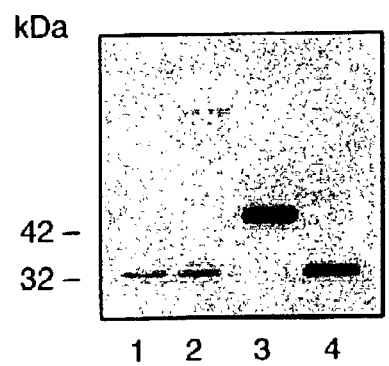
FIG._2A
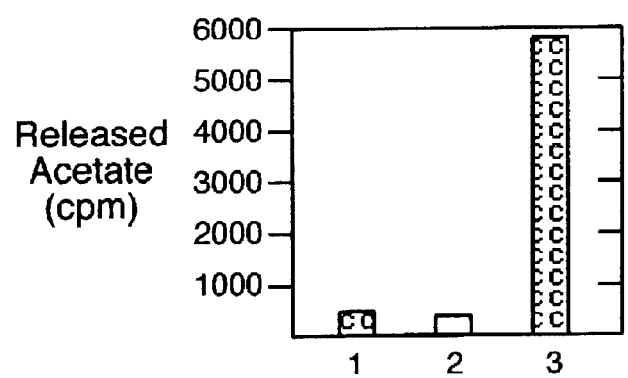
FIG._2B
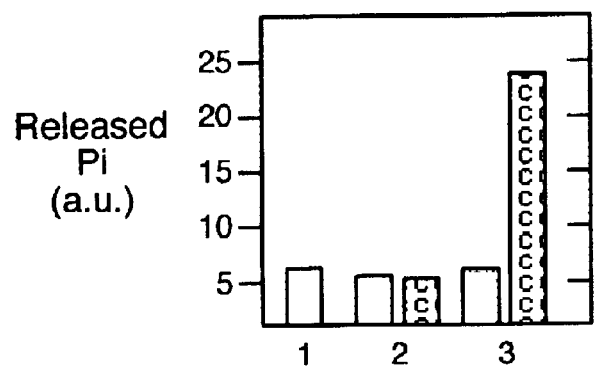
FIG._2C

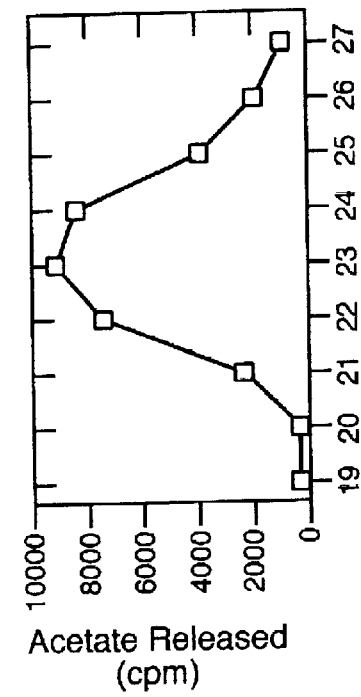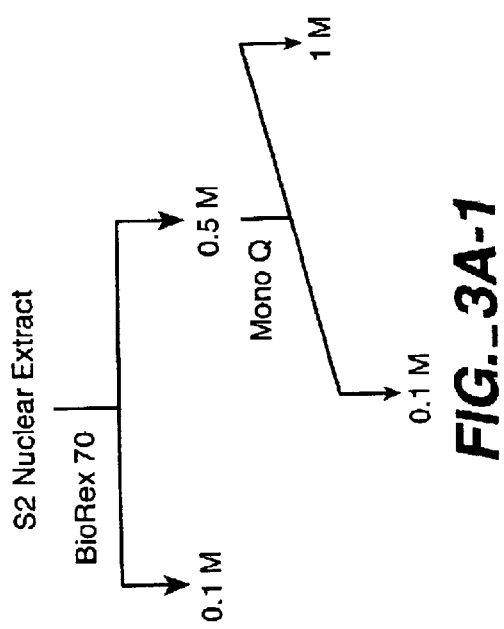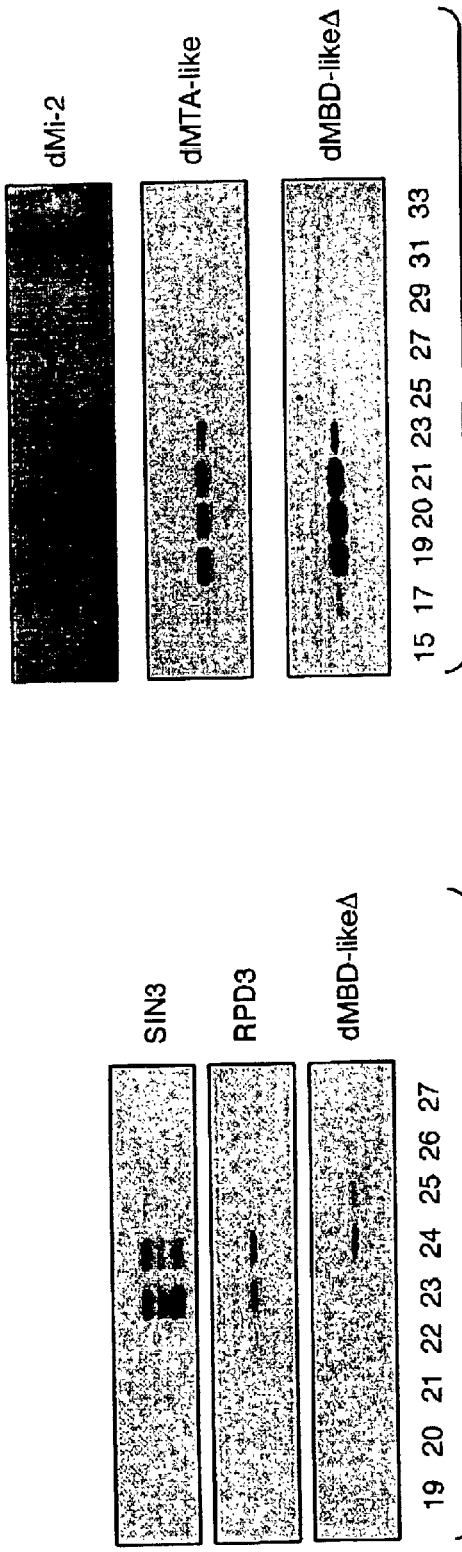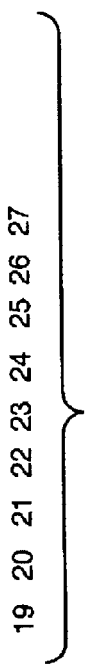

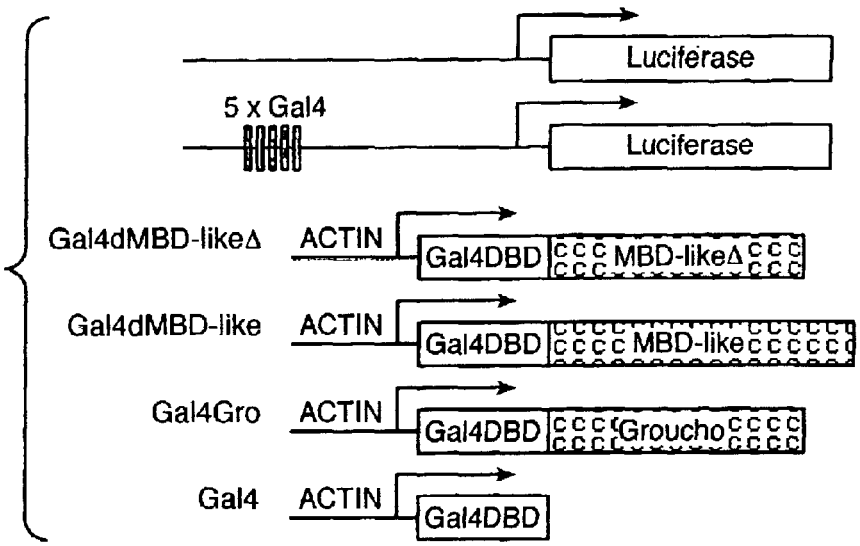
FIG._4A
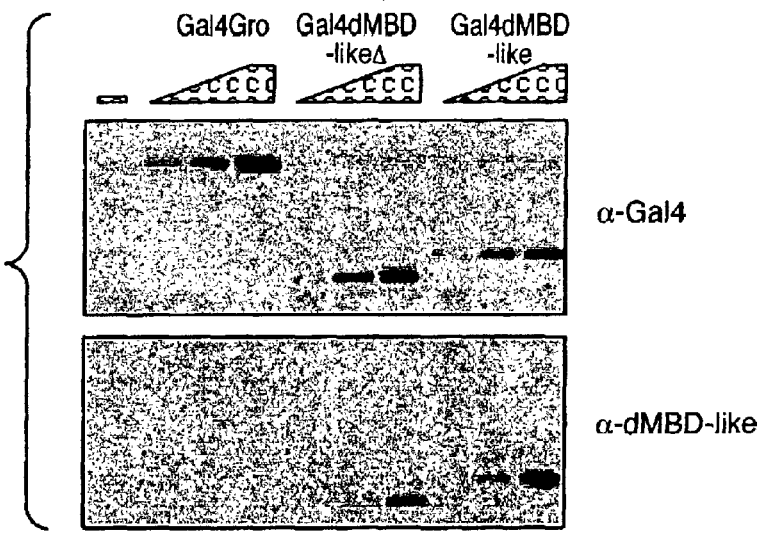
FIG._4C
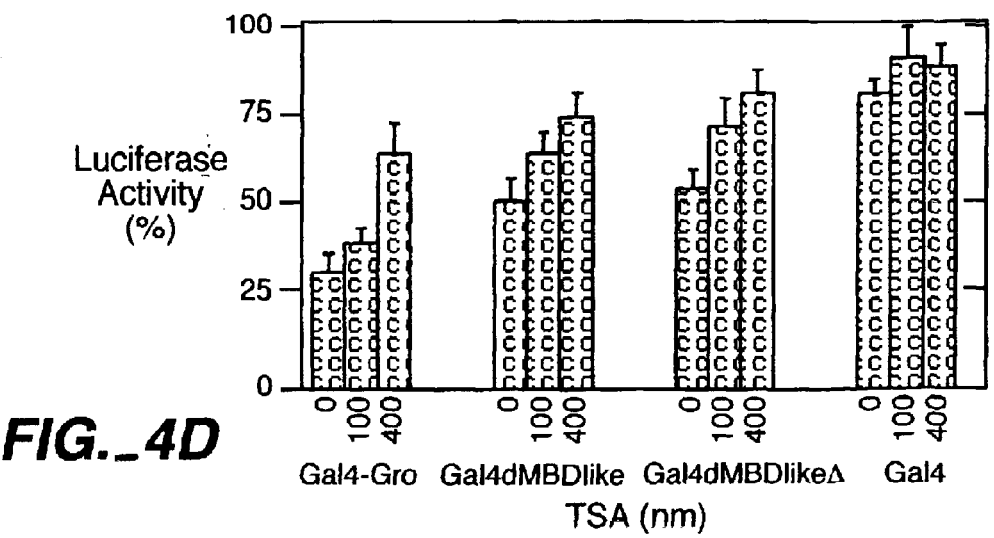
FIG._4D

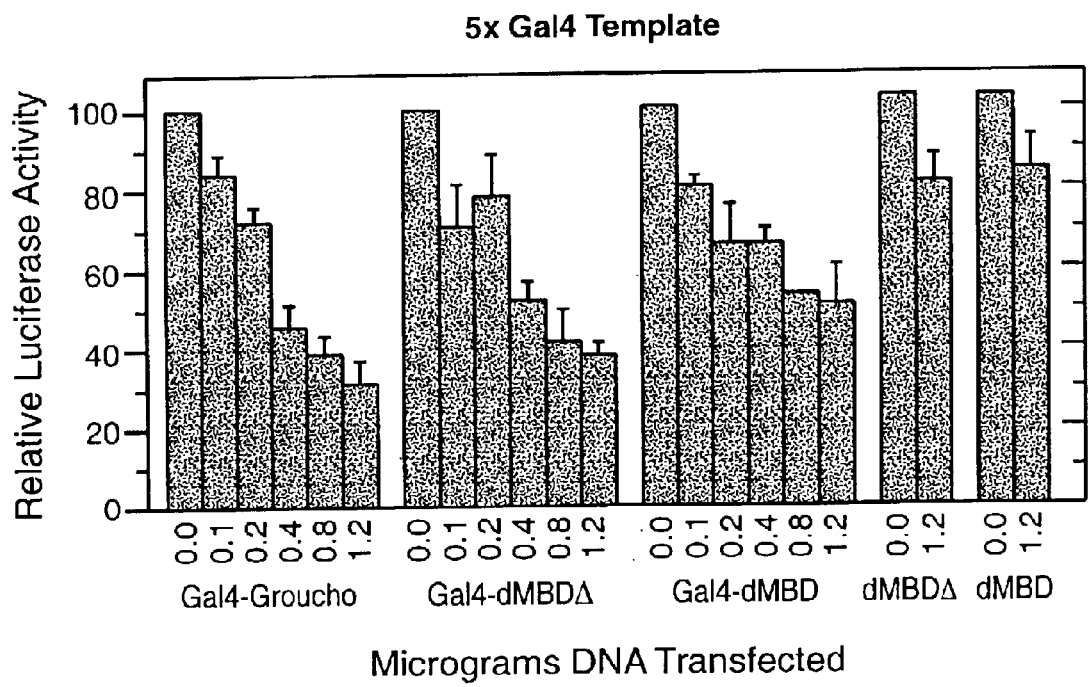
FIG._4B-1
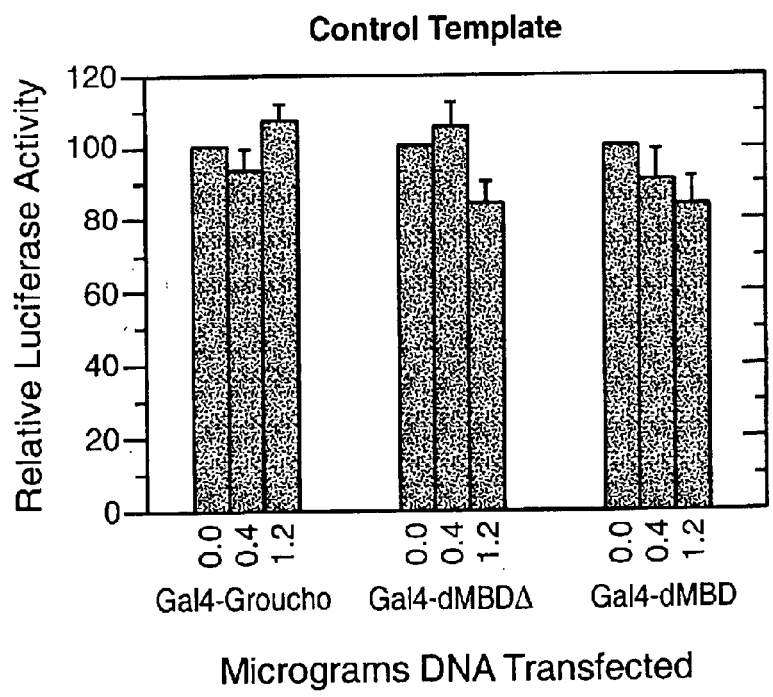
FIG._4B-2

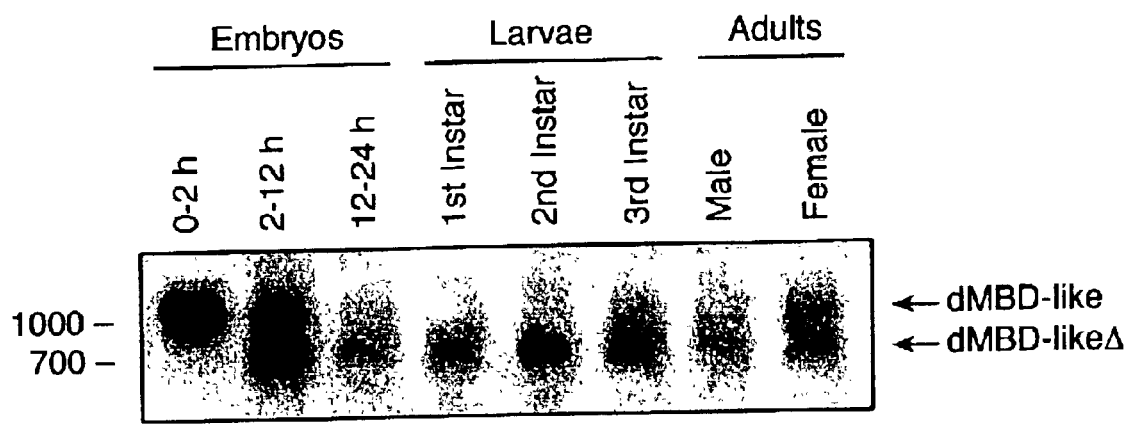
FIG._5A
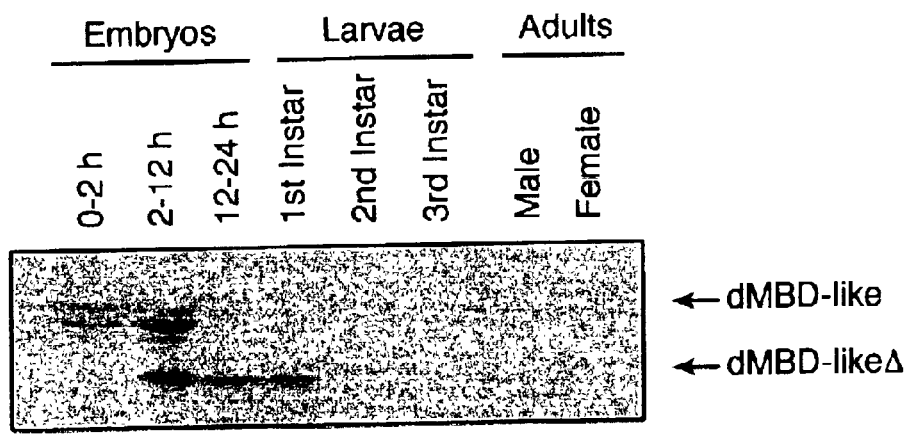
FIG._5B tion (Heard et al. (1997) *Annual Rev Genet* 31:571–610). A

MODULATION OF GENE EXPRESSION USING LOCALIZATION DOMAINS

CROSS-REFERENCE TO RELATED APPLICATIONS

This application is related to U.S. Provisional Patent Application Ser. No. 60/236,884, filed 29 Sep. 2000, from which priority is claimed under 35 USC §119(e)(1), and which application is incorporated herein by reference in its entirety.

TECHNICAL FIELD

The present disclosure is in the field of gene regulation, specifically, using compositions containing localization domain polypeptides, or functional fragments thereof, to modulate gene expression.

BACKGROUND

The development of an organism and ultimate function of any given cell in that organism depends on the particular set of genes being expressed (e.g., transcribed and translated) in the cell. Since virtually all the genes in the human genome have now been sequenced, the challenge now is to understand the molecular mechanisms that allow these genes to be selectively expressed.

In vertebrates, DNA methylation of CpG dinucleotides has long been identified as an important mechanism of development. DNA methylation is required for normal development (Ohki et al (1999) *EMBO J* 18:6653–6661; Okano et al. (1999) *Cell* 99:247–257); is correlated with genomic imprinting (Ashburner (1972) *Results Probl Cell Differ* 4:101–151; Grunstein et al. (1997) *Nature* 389:349–352) and is involved in X-chromosome inactivation (Heard et al. (1997) *Annual Rev Genet* 31:571–610). A large body of evidence indicates that cytosine methylation leads to the assembly of a specialized, heritable, repressive chromatin architecture through the recruitment of histone deacetylases (Bird and Wolffe (1999) *Cell* 99:451–454; Siegfried et al. (1997) *Curr Biol* 7:R305–307). However, the precise role of DNA methylation in tissue specific regulation of non-imprinted genes remains contentious (Bird (1997) *Trends Genet* 13:469–472).

Thus, DNA methylation appears to be critical in vertebrate development, which relies upon the imposition of progressively more stable states of transcriptional repression (Steinbach et al. (1997) *Nature* 389:395–399; Mannervik et al. (1999) *Science* 284:606–609). Further, DNA methylation may play a role in partitioning the genome, and the chromosomal infrastructure within which it is packaged, into active and inactive intranuclear compartments (Bird et al. (1995) *Trend Genet.* 11:94–99). For example, mouse primordial germ cells, embryonic stem cells and the cells of the blastocyst can progress through the cell cycle and divide without detectable DNA methylation (Lei et al. (1996) *Development* 122:3195–3205). Once differentiation begins, however, DNA methylation becomes essential for individual cell viability (Li et al. (1992) *Cell* 69:915–926; Okano et al. (1999) *Cell* 99:247–257).

DNA methylation has also been implicated in clinical disease states. Parasitic DNA, e.g., retrotransposons, retrovirus genomes, lentivirus genomes, L1 elements and Alu elements are known to be CpG rich. It has been proposed that DNA methylation may have arisen as a genome-defense system to silence expression of these parasitic elements and limit their spread through the genome (Yoder et al. (1997) *Trend Genet.* 13:335–340; Colot et al. (1999) *Bio Essays* 21:402–411). Additionally, several genetic diseases have been described that cause methylation defects, including the ICF syndrome (Xu et al. (1999) *Nature* 402:187–189), Rett syndrome (Amir et al. (1999) *Nature Genet.* 23:185–188) and fragile X syndrome (Oberle et al. (1991) *Science* 252:1711–1714).

Cellular DNA methylation patterns seem to be established by a complex interplay of at least three independent DNA methyltransferases: DNMT1, DNMT3A and DNMT3B (Kaludov and Wolffe (2000) *Nuc Acids Res* 28:1921–1928, and references cited therein). Methyltransferases are required for de novo methylation that occurs in the genome following embryo implantation and for the de novo methylation of newly integrated retroviral sequences in mouse ES cells (Okano et al. (1999) *Cell* 99:247–257). Proteins having significant homology to vertebrate methyltransferases been identified in zebrafish, *Arabidopsis thaliana* and maize (Okano et al. (1998) *Nature Genet* 19:219–220; Cao et al. (2000) *PNAS USA* 97:4979–4984).

In addition to the methyltransferases, a group of proteins which bind to methylated CpG sequences have also been identified. The methyl-CpG-binding protein MECP2 has been most characterized. MECP2 has been shown to selectively reocgnize methylated DNA and to repress transcription in methylated regions of the genome (Lewis et al. (1992) *Cell* 69:905–914). MECP2 contains at least two domains: the methyl-CpG-binding domain (MBD), which recognizes symmetrically methylated CpG dinucleotides through contacts in the major groove of the double helix (Wakefield et al. (1999) *J. Mol. Biol.* 291:1055–1065) and a transcriptional repression domain (TRD), which interacts with several other regulatory proteins (Nan et al. (1997) *Cell* 88:471–481. MECP2 selectively represses transcription of methylated templates in the absence of an organized chromatin structure and, when tethered to a specific heterologous Gal4-binding domain, its TRD confers transcriptional repression by interacting with TFIIB, a component of the basal transcription machinery (Kaludov et and Wolffe, (2000) *Nucleic Acids Res.* 28:1921–1928). Methyl binding domain proteins associate with corepressor complexes that include histone deacetylases. Methyl CpG binding proteins have also been shown to be components of chromatin-remodeling complexes, for example the MECP2 repressor complex. Recruitment of a histone deacetylase occurs indirectly through its interaction with the Sin3A adaptor proteins, which causes transcriptional silencing, in part by deacetylation of histones, directing the formation of stable repressive chromatin structures.

Thus, methylation of DNA can repress transcription through multiple mechanisms (see, e.g., Kaludov and Wolffe (2000) *Nuc Acids Res* 28:1921–1928, and references cited therein). Pathways of repression include direct inhibition of transcription through the failure of transcription factors to associate with methylated recognition elements (Iguchi-Arigan et al. (1989) *Genes Dev.* 3:612–619) and indirect pathways involving either occlusion of methylated sequences by transcriptional repressors that recognize methylated DNA (Meehan et al. (1992) *Nucleic Acids Res.* 20:5085–5092) or the modification of chromatin structure targeted by methyl-CpG-specific transcriptional repressors (Buschhausen et al. (1987) *PNAS USA* 84:1177–1181; Kass et al. (1997) *Curr. Biol.* 7:157–165).

Despite the characterization of the functional properties of methyl-CpG-specific binding proteins and their constituent MBDs, it has not heretofore been possible to target the various functional activities of MBDs, for use in specific and directed modulation of gene expression.

SUMMARY

In one aspect, methods of compartmentalizing a region of interest in cellular chromatin are provided. The methods comprise contacting the region of interest with a composition that binds to a binding site in cellular chromatin, wherein the binding site is in a gene of interest and wherein the composition comprises a localization domain or functional fragment thereof, and a DNA binding domain or functional fragment thereof. In certain embodiments, the composition is a fusion molecule, for example a fusion polypeptide. In other embodiments, the region of interest is compartmentalized into a nuclear compartment for packaging as heterochromatin. The methods are useful in a variety of cells, including but not limited to, plant cells and animal cells (e.g., human). The localization domain can be a methyl CpG binding domain obtained, for example, from MECP2, MBD1, MBD2, MBD3, dMBD-like and dMBD-likeΔ, or one or more functional fragments thereof. The DNA-binding domain can be, for example, a zinc finger protein or a triplex-forming nucleic acid or a minor groove binder. In certain embodiments, any of the methods described herein facilitate modulation of expression of a gene associated with the region of interest, for example repression of the gene. In other embodiments, the methods described herein further comprise the step of contacting a cell with a polynucleotide encoding a fusion polypeptide, wherein the fusion polypeptide is expressed in the cell. The gene can encode any product, for example, vascular endothelial growth factor, erythropoietin, androgen receptor, PPAR-γ2, p16, p53, pRb, dystrophin and e-cadherin. Furthermore, in other embodiments, the region of interest is involved in disease states selected from the group consisting of ICF syndrome, Rett syndrome and Fragile X syndrome.

In another aspect, methods are provided for modulation of gene expression, wherein the methods comprise the step of contacting a region of DNA in cellular chromatin with a fusion molecule that binds to a binding site in cellular chromatin, wherein the binding site is in the gene and wherein the fusion molecule comprises a DNA binding domain and a localization domain, for example, a methyl CpG binding domain. Modulation of the gene can be, for example, repression of the target gene. The DNA-binding domain of the fusion molecule can be, for example, a zinc finger DNA-binding domain. Further, the DNA binding domain can bind to a variety of target sites, for example to a target site in a gene encoding a product selected from the group consisting of vascular endothelial growth factor, erythropoietin, androgen receptor, PPAR-γ2, p16, p53, pRb, dystrophin and e-cadherin. The localization domain can be a methyl CpG binding domain obtained from, for example, MECP2, MBD1, MBD2, MBD3, dMBD-like and dMBD-likeΔ, or one or more functional fragments thereof. In still further embodiments, the methods involve contacting cellular chromatin with a plurality of fusion molecules.

In other aspects, methods of modulating gene expression are provided, wherein the methods comprise the step of contacting a region of DNA in cellular chromatin with a fusion molecule that binds to a binding site in cellular chromatin, wherein the binding site is in the gene and wherein the fusion molecule comprises a DNA binding domain, a localization domain such as, for example, a methyl CpG binding domain and a regulatory domain (such fusion molecules can include functional fragments of any of these domains). Modulation of gene expression can be, for example, repression (e.g., using a repression domain or functional fragment thereof as the transcriptional regulatory domain) or activation (e.g, using an activation domain, such as for example VP16, or a functional fragment thereof, as the transcriptional regulatory domain). The regulatory domain can also comprise a component of a chromatin remodeling complex (or a functional fragment thereof) with the capacity to recruit complexes capable of remodeling chromatin of the target gene into either a transcriptionally active or a transcriptionally inactive state, as desired. The DNA-binding domain of the fusion molecule can comprise a zinc finger DNA-binding domain. Further, the DNA binding domain can bind to any target site, for example a target site in a gene encoding a product selected from the group consisting of vascular endothelial growth factor, erythropoietin, androgen receptor, PPAR-γ2, p16, p53, pRb, dystrophin and e-cadherin. The localization domain can be a methyl CpG binding domain obtained, for example, from MECP2, MBD1, MBD2, MBD3, dMBD-like and dMBD-likeΔ, or one or more functional fragments thereof. In still further embodiments, a plurality of fusion molecules is contacted with cellular chromatin, wherein each of the fusion molecules binds to a distinct binding site, for example, to modulate expression of one or more genes.

In yet another aspect, a fusion polypeptides comprising a localization domain or functional fragment thereof; and a DNA binding domain or a functional fragment thereof is provided. In certain embodiments, the fusion polypeptide also comprises a regulatory domain, for example an activation domain (e.g., VP-16, p65), a repression domain (e.g., KRAB, v-erbA) or a component of a chromatin remodeling complex. Any of the polypeptides described herein can include a DNA-binding domain which is a zinc finger DNA binding domain and a localization domain which can be, for example, a methyl CpG binding domain such as obtained, for example, from MECP2, MBD 1, MBD2, MBD3, dMBD-like and dMBD-likeΔ or functional fragments thereof. These fusion polypeptides can bind, for example, to a target site in a gene encoding a product selected from the group consisting of vascular endothelial growth factor, erythropoietin, androgen receptor, PPAR-γ2, p16, p53, pRb, dystrophin and e-cadherin. Polynucleotides encoding any of the fusion polypeptides described herein are also provided, as are cells comprising the polypeptides and/or polynucleotides encoding the polypeptides.

These and other embodiments will be readily apparent to one of skill in the art upon reading the present disclosure.

BRIEF DESCRIPTION OF THE DRAWINGS

FIGS. 1A and 1B, are sequence alignments depicting that *Drosophila* contains multiple proteins with significant similarity to vertebrate methyl CpG binding proteins.

FIG. 1A depicts the similarity of Drosophila proteins to the methyl CpG binding domain motif. The amino acid sequences corresponding to the methyl CpG binding motif of human MeCP2 (SEQ ID NO:5), human MBDI (SEQ ID NO:6), human MBD4 (SEQ ID NO:7), human MBD2 (SEQ ID NO:8), and *Xenopus* MBD3 (xMBD3) (SEQ ID NO:9) are aligned with the corresponding sequences from the indicated *Drosophila* gene products (CG10042, SEQ ID NO:10; CG12196, SEQ ID NO:11; sba, SEQ ID NO:12; dMBD-like, SEQ ID NO:13). A 23 amino acid segment from the *Drosophila* MBD-like sequence (NNNASSNNNSSATASSNNNNNKV, SEQ ID NO: 1) has been omitted in the loop L1 to facilitate the alignment. Positions of beta strands, loops, and the alpha helix defined by the solution structures of MeCP2 and MBD1 are indicated above the alignment. Residues boxed in the alignment are identical or similar in all or all but one the sequences depicted. Residues indicated by the symbol ψ define hydrophobic residues crucial for the basic fold of the motif. Residues indicated by the squares constitute the basic patch on one surface of the wedge structure. The two residues indicated by the diamond symbols are conserved hydrophobic residues critical for the structure of the hairpin loop.

FIG. 1B depicts the similarity of dMBD-like to *Xenopus* MBD3. The deduced amino acid sequence of *Drosophila* MBD-like (SEQ ID NO:14) and MBD-likeΔ (SEQ ID NO: 15) are aligned with *Xenopus* MBD3 (SEQ ID NO:17) and MBD3-LF (SEQ ID NO: 16). Amino acids identical in all the proteins are shaded in dark gray, amino acids with similar side chain chemistry are shaded light gray and indicated by upward arrows. A box indicates the methyl CpG binding domains. The secondary structure of the methyl-CpG binding domain is indicated at the top. Arrows represent β-sheet segments, rectangles represent α-helices. Loops appear as thick lines.

FIG. 1C is an immunoblot depicting that immobilized dMBD-like fails to bind methylated DNA. The bottom two panels depict Southwestern assays performed with recombinant X. laevis MBD3, Drosophila MBD-like and MBD-likeΔ. The middle panel (labeled GAC 12) is probed with the unmethylated DNA probe. The lower panel (labeled GAM12) is probed with the methylated probe. The top panel (labeled Coomassie) is a Coomassie Blue stained gel of lanes identical to those in the middle and lower panels. Each panel contains triplicate samples of the indicated protein.

FIG. 1D is an immunoblot depicting that dMBD-like fails to bind methylated DNA in solution. *Xenopus* MBD3, Drosophila MBD-like and MBD-likeΔ were examined for the ability to bind to methylated (GAM12) or unmethylated (GAC12) DNA probes. Binding reactions were performed as described in Example 1. Lanes 1–5 of each gel contain radiolabelled, unmethylated GAC 12 as a probe and lanes 6–10 contain radiolabelled, fully methylated GAM12. For each gel, lanes 1 and 6 contain only the probe without any added protein. Lanes 2 and 7 contain 50 ng of protein, lanes 3 and 8 contain 75 ng of protein and lanes 4, 5, 9 and 10 contain 150 ng of protein. Binding was competed with either GAC12 or GAM12 as competitor (U, unmethylated GAC12; M, methylated GAM12) as indicated at the bottom of the figure.

FIG. 2A is an immunoblot showing that dMBD-likeΔ is the predominant form of dMBD-like protein found in *Drosophila* S2 cells. The immunoblot was prepared and analyzed with α-dMBD-like serum as described in Example 1. The lanes were loaded as follows: Lane 1, 5 μl S2 nuclear extract, Lane 2, 10 μl nuclear extract, Lane 3, recombinant dMBD-like. Lane 4, recombinant dMBD-likeΔ.

FIG. 2B shows association of dMBD-likeΔ with histone deacetylase activity in S2 nuclear extracts. Immunoprecipitations were performed as described in Example 1 on S2 nuclear extracts using the α-dMBD-like antiserum or pre-immune serum from the same rabbit. Precipitates were analyzed for HDAC activity using the deacetylase assay described in Example 1. Acetate released is indicated in the bar graph as cpm tritium. Samples are as follows: 1, no antiserum control; 2, pre-immune serum; 3 α-dMBD-like serum. Precipitations were performed multiple times; a representative example is depicted.

FIG. 2C shows association of dMBD-like with nucleosome-stimulated ATPase activity. Immunoprecipitations were performed on S2 nuclear extracts as described in FIG. 2B. Precipitated proteins were analyzed for ATPase activity as described in Example 1. The bar graph depicts inorganic phosphate produced in arbitrary units. Samples are as follows: 1, no antiserum control; 2, pre-immune serum; 3, α-dMBD-like serum. Light and dark bars correspond respectively to the absence and the presence of chicken erythrocyte mononucleosomes during the ATPase assay.

FIG. 3A is a schematic depicting partial resolution of dMBD-likeΔ from SIN3 and RPD3 by ion exchange chromatography. S2 nuclear extract was fractionated according to the scheme depicted in FIG. 3A and described in detail in Example 1. HDAC activity assays and immunoblot analysis of the indicated fractions from the MonoQ column are shown below the flow chart. FIG. 3B is an immunoblot depicting coelution of dMBD-likeΔ with components of the Mi-2 complex on a gel filtration column. Fraction 24 from the MonoQ column was resolved on a Superose 6 gel filtration column as described in Example 1. Indicated fractions were analyzed by immunoblot using the antisera are indicated.

FIG. 4A shows schematic depictions of the plasmids used for the transfection assays. A description of plasmid construction is presented in Example 1.

FIG. 4B depicts transcriptional repression as a function of dose of Gal4-tethered dMBD-like, dMBD-likeΔ, and Groucho. Experiments were performed in triplicate and error bars are shown.

FIG. 4C is an immunoblot showing that expression of the transiently transfected Gal4 derivatives is equivalent. Extracts from cells transfected with each of the indicated constructs were analyzed by immunoblot using either α-dMBD-like or α-Gal4 antisera.

FIG. 4D shows that TSA relieves repression by Gal4-Gro, Gal4-dMBD-like and Gal4-dMBD-likeΔ. The graph depicts luciferase activity from the $G_5DE_5tkLuc$ reporter driven by the indicated Gal4 derivatives as a percentage of luciferase expression from the same reporter in the absence of any transfected Gal4 protein. All the samples are the average of triplicates. TSA was used at 100 nM and 400 nM as indicated in the figure.

FIGS. 5A and 5B show regulation dMBD-like and dMBD-likeΔ mRNA and protein expression during development.

FIG. 5A is a Northern (RNA) blot showing dMBD-like and dMBD-likeΔ expression through development. Total RNA isolated from various developmental stages (~10 μg/lane) was fractionated on a formaldehyde-agarose gel and transferred to a nylon membrane as described in Example 1. Lanes 1–3, embryonic stages: 0–3 h, 3–12 h, 12–24 h; lanes 4–6, larval stages, $1^{st}$, $2^{nd}$ and $3^{rd}$ Instars. Lane 7 male adult flies, lane 8, female adult flies.

FIG. 5B is an immunoblot showing dMBD-like and dMBD-likeΔ levels during development. Lanes 1–8 correspond to the same samples as in panel A. Equivalent amounts of protein were loaded in each lane.

DETAILED DESCRIPTION

Disclosed herein are compositions containing localization domains and methods for their preparation and use. The methods and compositions allow, for example, localization of corepression complexes either (1) to facilitate their recruitment to particular sites within chromatin by fusion of a localization domian to a DNA binding domain that can access such a site to repress gene activity or (2) to interfere with corepressive function, for example by attaching an activation domain to a DNA binding domain-localization domain fusion to affect repressive influences and promote gene activation.

In a preferred embodiment, a localization domain is a methyl binding domain (MBD) or a functional fragment thereof. Vertebrate methyl binding domain proteins are known to recognize and bind to CpG dinucleotide sequences in which the C residue is methylated. However, a surprising and unexpected ability of MBDs (including invertebrate MBDs which do not bind to methylated DNA) is their capacity to localize DNA, for example in corepression complexes. Thus, the methods and compositions disclosed herein allow for modulation of gene expression by employing a composition comprising a localization domain polypeptide or functional fragment thereof. The localization domain polypeptides can be selected for their ability to affect transcription, for example via their capacity to interact with corepression complexes and/or facilitate compartmentalization of target sequences in repressive compartments of the nucleus.

In one aspect, compositions and methods useful in modulating expression of a target gene are provided. The compositions typically comprise a fusion molecule comprising a localization domain and a DNA-binding domain. In one preferred embodiment, the localization domain comprises a MBD (or functional fragment thereof) and the DNA binding domain comprises a zinc finger protein (ZFP) or functional fragment thereof. In still further aspects, the compositions further comprise a transcriptional regulatory domain (a "functional domain"), for example an activation or repression domain.

Thus, it will be apparent to one of skill in the art that the use of localization domain(s) or functional fragments thereof will facilitate the regulation of many processes involving gene expression including, but not limited to, replication, recombination, repair, transcription, telomere function and maintenance, sister chromatid cohesion, mitotic chromosome segregation and, in addition, binding of transcription factors.

General

The practice of the disclosed methods, and the uses of the disclosed compositions, employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989; Sambrook et al MOLECULAR CLONING: A LABORATORY MANUAL, Third edition, Cold Spring Harbor Laboratory Press, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

The terms "nucleic acid," "polynucleotide," and "oligonucleotide" are used interchangeably and refer to a deoxyribonucleotide or ribonucleotide polymer in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties. In general, an analogue of a particular nucleotide has the same base-pairing specificity; i.e., an analogue of A will base-pair with T. The terms also encompasses nucleic acids containing modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Nucleic acids include, for example, genes, cDNAs, and mRNAs. Polynucleotide sequences are displayed herein in the conventional 5'-3' orientation.

Chromatin is the nucleoprotein structure comprising the cellular genome. "Cellular chromatin" comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 (or its equivalent) is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin, and includes both transcriptionally active chromatin (euchromatin) and transcriptionally inactive chromatin (heterochromatin).

A "chromosome" is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

An "exogenous molecule" is a molecule that is not normally present in a cell, but can be introduced into a cell by one or more genetic, biochemical or other methods. Normal presence in the cell is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotien, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., protein or nucleic acid (i.e., an exogenous gene), providing it has a sequence that is different from an endogenous molecule. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer.

By contrast, an "endogenous molecule" is one that is normally present in a particular cell at a particular developmental stage under particular environmental conditions. For example, an endogenous nucleic acid can comprise an endogenous gene, a chromosome, the genome of a mitochondrion, chloroplast or other organelle, or a naturally-occurring episomal nucleic acid. Additional endogenous molecules can include proteins, for example, transcription factors and components of chromatin remodeling complexes.

A "fusion molecule" is a molecule in which two or more subunit molecules are linked, preferably covalently. The subunit molecules can be the same chemical type of molecule, or can be different chemical types of molecules. Examples of the first type of fusion molecule include, but are not limited to, fusion polypeptides (for example, a fusion between a ZFP DNA-binding domain and a methyl binding domain) and fusion nucleic acids (for example, a nucleic acid encoding the fusion polypeptide described supra). Examples of the second type of fusion molecule include, but are not limited to, a fusion between a triplex-forming nucleic acid and a polypeptide, and a fusion between a minor groove binder and a nucleic acid.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of a mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Gene activation" and "augmentation of gene expression" refer to any process which results in an increase in production of a gene product. A gene product can be either RNA (including, but not limited to, mRNA, rRNA, tRNA, and structural RNA) or protein. Accordingly, gene activation includes those processes which increase transcription of a gene and/or translation of a mRNA. Examples of gene activation processes which increase transcription include, but are not limited to, those which facilitate formation of a transcription initiation complex, those which remodel chromatin into an active state, those which increase transcription initiation rate, those which increase transcription elongation rate, those which increase processivity of transcription and those which relieve transcriptional repression (by, for example, blocking the binding of a transcriptional repressor). Gene activation can constitute, for example, inhibition of repression as well as stimulation of expression above an existing level. Examples of gene activation processes which increase translation include those which increase translational initiation, those which increase translational elongation and those which increase mRNA stability. In general, gene activation comprises any detectable increase in the production of a gene product, preferably an increase in production of a gene product by about 2-fold, more preferably from about 2- to about 5-fold or any integer therebetween, more preferably between about 5- and about 10-fold or any integer therebetween, more preferably between about 10- and about 20-fold or any integer therebetween, still more preferably between about 20- and about 50-fold or any integer therebetween, more preferably between about 50- and about 100-fold or any integer therebetween, more preferably 100-fold or more.

"Gene repression" and "inhibition of gene expression" refer to any process which results in a decrease in production of a gene product. A gene product can be either RNA (including, but not limited to, mRNA, rRNA, tRNA, and structural RNA) or protein. Accordingly, gene repression includes those processes which decrease transcription of a gene and/or translation of a mRNA. Examples of gene repression processes which decrease transcription include, but are not limited to, those which inhibit formation of a transcription initiation complex, those which remodel chromatin into an inactive state, those which decrease transcription initiation rate, those which decrease transcription elongation rate, those which decrease processivity of transcription and those which antagonize transcriptional activation (by, for example, blocking the binding of a transcriptional activator). Gene repression can constitute, for example, prevention of activation as well as inhibition of expression below an existing level. Examples of gene repression processes which decrease translation include those which decrease translational initiation, those which decrease translational elongation and those which decrease mRNA stability. Transcriptional repression includes both reversible and irreversible inactivation of gene transcription. In general, gene repression comprises any detectable decrease in the production of a gene product, preferably a decrease in production of a gene product by about 2-fold, more preferably from about 2- to about 5-fold or any integer therebetween, more preferably between about 5- and about 10-fold or any integer therebetween, more preferably between about 10- and about 20-fold or any integer therebetween, still more preferably between about 20- and about 50-fold or any integer therebetween, more preferably between about 50- and about 100-fold or any integer therebetween, more preferably 100-fold or more. Most preferably, gene repression results in complete inhibition of gene expression, such that no gene product is detectable.

"Eucaryotic cells" include, but are not limited to, fungal cells (such as yeast), plant cells, insect cells, animal cells, teleost cells, mammalian cells and human cells.

The terms "operable linkage," "operably linked," "operative linkage" and "operatively linked" are used with reference to a juxtaposition of two or more components (such as sequence elements), in which the components are placed into a functional relationship with one another. Thus operatively linked components are arranged such that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. An operatively linked transcriptional regulatory sequence is generally joined in cis with a coding sequence, but need not be directly adjacent to it. For example, an enhancer can constitute a transcriptional regulatory sequence that is operatively-linked to a coding sequence, even though they are not contiguous. Similarly, certain amino acid sequences that are non-contiguous in a primary polypeptide sequence may nonetheless be operably linked due to, for example folding of a polypeptide chain.

With respect to fusion polypeptides, the terms "operably linked" and "operatively linked" can refer to the fact that each of the components performs the same function in linkage to the other component as it would if it were not so linked. For example, with respect to a fusion polypeptide in which a ZFP DNA-binding domain is fused to a transcriptional activation domain (or functional fragment thereof), the ZFP DNA-binding domain and the transcriptional activation domain (or functional fragment thereof) are in operative linkage if, in the fusion polypeptide, the ZFP DNA-binding domain portion is able to bind its target site and/or its binding site, while the transcriptional activation domain (or functional fragment thereof) is able to activate transcription.

A "functional fragment" of a protein, polypeptide or nucleic acid is a protein, polypeptide or nucleic acid whose sequence is not identical to its native or full-length counterpart, yet retains the same function as the native or full-length counterpart. A functional fragment can possess more, fewer, or the same number of residues as the corresponding native or full-length molecule, and/or can contain one ore more amino acid or nucleotide analogues or substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. See Ausubel et al., supra. The ability of a protein to interact with another protein can be determined, for example, by co-immunoprecipitation, two-hybrid assays or complementation, both genetic and biochemical. See, for example, Fields et al (1989) Nature 340:245–246; U.S. Pat. No. 5,585,245 and PCT WO 98/44350.

The term "recombinant," when used with reference to a cell, indicates that the cell replicates an exogenous nucleic acid, or expresses a peptide or protein encoded by an exogenous nucleic acid. Recombinant cells can contain genes that are not found within the native (non-recombinant) form of the cell. Recombinant cells can also contain genes found in the native form of the cell wherein the genes are modified and re-introduced into the cell by artificial means. The term also encompasses cells that contain a nucleic acid endogenous to the cell that has been modified without removing the nucleic acid from the cell; such modifications include those obtained by gene replacement, site-specific mutation, and related techniques. Thus, for example, recombinant cells express genes that are not found within the native (naturally occurring) form of the cell or express a second copy of a native gene that is otherwise normally or abnormally expressed, underexpressed or not expressed at all. Recombinant cells also include cells or cell lines derived from cells that have been modified as described.

The term "recombinant" when used with reference, e.g., to a nucleic acid, protein, or vector, refers to nucleic acids, proteins or vectors that have been modified by the introduction of heterologous nucleic acid or amino acid sequence, and includes any other alterations of a native nucleic acid or protein.

An "expression vector" is a nucleic acid construct, generated recombinantly or synthetically, with a series of specified nucleic acid elements that permit transcription of a particular nucleic acid in a host cell, and optionally integration and/or replication of the expression vector in a host cell. The expression vector can be part of a plasmid, viral genome, or nucleic acid fragment, of viral or non-viral origin. Expression vectors can be, for example, naked DNA molecules, or can comprise nucleic acid of viral or nonviral origin packaged into viral particles. Typically, the expression vector includes an "expression cassette," which comprises a nucleic acid to be transcribed operably linked to control elements that are capable of effecting expression of a nucleic acid that is operatively linked to the control elements in hosts compatible with such sequences. Expression cassettes include at least promoters and optionally, transcription termination signals. Typically, a recombinant expression cassette includes at least a nucleic acid to be transcribed (e.g., a nucleic acid encoding a desired polypeptide) and a promoter. Additional factors necessary or helpful in effecting expression can also be used, for example, an expression cassette can also include nucleotide sequences that encode a signal sequence that directs secretion of an expressed protein from the host cell. Transcription termination signals, enhancers, and other nucleic acid sequences that influence gene expression can also be included in an expression cassette.

The term "naturally occurring," as applied to an object, means that the object can be found in nature.

The terms "polypeptide," "peptide" and "protein" are used interchangeably herein to refer to a polymer of amino acid residues. The terms apply to amino acid polymers in which one or more amino acid residue is an analog or mimetic of a corresponding naturally occurring amino acid, as well as to naturally occurring amino acid polymers. Polypeptides can be modified, e.g., by phosphorylation, methylation, myristilation, acetylation and/or the addition of carbohydrate residues to form glycoproteins. The terms "polypeptide," "peptide" and "protein" include all of these modified polypeptides, as well as polypeptides comprising any additional covalent or non-covalent modification. Polypeptide sequences are displayed herein in the conventional N-terminal to C-terminal orientation.

A "subsequence" or "segment" when used in reference to a nucleic acid or polypeptide refers to a sequence of nucleotides or amino acids that comprise a part of a longer sequence of nucleotides or amino acids (e.g., a polypeptide), respectively.

The term "antibody" as used herein includes antibodies obtained from both polyclonal and monoclonal preparations, as well as, the following: (i) hybrid (chimeric) antibody molecules (see, for example, Winter et al. (1991) Nature 349:293–299; and U.S. Pat. No. 4,816,567); (ii) F(ab')2 and F(ab) fragments; (iii) Fv molecules (noncovalent heterodimers, see, for example, Inbar et al. (1972) Proc. Natl. Acad. Sci. USA 69:2659–2662; and Ehrlich et al. (1980) Biochem 19:4091–4096); (iv) single-chain Fv molecules (sFv) (see, for example, Huston et al. (1988) Proc. Natl. Acad. Sci. USA 85:5879–5883); (v) dimeric and trimeric antibody fragment constructs; (vi) humanized antibody molecules (see, for example, Riechmann et al. (1988) Nature 332:323–327; Verhoeyan et al. (1988) Science 239:1534–1536; and U.K. Patent Publication No. GB 2,276, 169, published Sep. 21, 1994); (vii) Mini-antibodies or minibodies (i.e., sFv polypeptide chains that include oligomerization domains at their C-termini, separated from the sFv by a hinge region; see, e.g., Pack et al. (1992) Biochem 31:1579–1584; Cumber et al. (1992) J. Immunology 149B:120–126); and, (vii) any functional fragments obtained from such molecules, wherein such fragments retain specific-binding properties of the parent antibody molecule.

"Specific binding" between an antibody or other binding agent and an antigen, or between two binding partners, means that the dissociation constant for the interaction is less than $10^{-6}$ M. Preferred antibody/antigen or binding partner complexes have a dissociation constant of less than about $10^{-7}$ M, and preferably $10^{-8}$ M to $10^{-9}$ M or $10^{-10}$ M or lower.

A "binding protein" or binding domain" is a protein or polypeptide that is able to bind non-covalently to another molecule. A binding protein can bind to, for example, a DNA molecule (a DNA-binding domain), an RNA molecule (an RNA-binding domain) and/or a protein molecule (a protein-binding domain). In the case of a protein-binding protein, it can bind to itself (to form homodimers, homotrimers, etc.) and/or it can bind to one or more molecules of a different protein or proteins. A binding domain can have more than one type of binding activity. For example, zinc finger proteins have DNA-binding, RNA-binding and protein-binding activity.

A "zinc finger binding protein" is a protein or polypeptide that binds DNA, RNA and/or protein, preferably in a sequence-specific manner, as a result of stabilization of protein structure through coordination of a zinc ion. The term zinc finger binding protein is often abbreviated as zinc finger protein or ZEP. The individual DNA binding domains are typically referred to as "fingers" A ZFP has least one finger, typically two fingers, three fingers, or six fingers. Each finger binds from two to four base pairs of DNA, typically three or four base pairs of DNA. A ZFP binds to a nucleic acid sequence called a target site or target segment. Each finger typically comprises an approximately 30 amino acid, zinc-chelating, DNA-binding subdomain. An exemplary motif characterizing one class of these proteins ($C_2H_2$ class) is -Cys-$(X)_{2-4}$-Cys-$(X)_{12}$-His-$(X)_{3-5}$-His (where X is any amino acid) (SEQ ID NO:4). Studies have demonstrated that a single zinc finger of this class consists of an alpha helix containing the two invariant histidine residues co-ordinated with zinc along with the two cysteine residues of a single beta turn (see. e.g., Berg & Shi, Science 271:1081–1085 (1996)).

Zinc finger proteins can be engineered to bind to predetermined sequences. Examples of zinc finger engineering include designed zinc finger proteins and selected zinc finger proteins. A "designed" zinc finger protein is a protein not occurring in nature whose structure and composition result principally from rational criteria. Rational criteria for design include application of substitution rules and computerized algorithms for processing information in a database storing information of existing ZFP designs and binding data, for example as described in PCT WO 98/53058, WO 98/53059, WO 99/53060 and WO 00/42219. A "selected" zinc finger protein is a protein not found in nature whose production results primarily from an empirical process such as phage display. See e.g., U.S. Pat. Nos. 5,789,538; 6,007,988; 6,013,453; WO 95/19431; WO 96/06166 WO 98/53057 and WO 98/54311.

A "target site" or "target sequence" is a sequence that is bound by a binding protein such as, for example, a ZFP. Target sequences can be nucleotide sequences (either DNA or RNA) or amino acid sequences. A single target site typically has about four to about ten base pairs, but can be as long as 18–20 base pairs, e.g., for a six-finger ZFP. Typically, a two-fingered ZFP recognizes a four to seven base pair target site, and a three-fingered ZFP recognizes a six to ten base pair target site. By way of example, a DNA target sequence for a three-finger ZFP is generally either 9 or 10 nucleotides in length, depending upon the presence and/or nature of cross-strand interactions between the ZFP and the target sequence. Target sequences can be found in any DNA or RNA sequence, including regulatory sequences, exons, introns, or any non-coding sequence.

A "target subsite" or "subsite" is the portion of a DNA target site that is bound by a single zinc finger, excluding cross-strand interactions. Thus, in the absence of cross-strand interactions, a subsite is generally three nucleotides in length. In cases in which a cross-strand interaction occurs (e.g., a "D-able subsite," as described for example in co-owned PCT WO 00/42219, incorporated by reference in its entirety herein) a subsite is four nucleotides in length and overlaps with another 3- or 4-nucleotide subsite.

"$K_d$" refers to the dissociation constant for the compound, i.e., the concentration of a compound (e.g., a zinc finger protein) that gives half maximal binding of the compound to its target (i.e., half of the compound molecules are bound to the target) under given conditions (i.e., when [target]<<$K_d$), as measured using a given assay system (see, e.g., U.S. Pat. No. 5,789,538). Any assay system can be used, as long is it gives an accurate measurement of the actual $K_d$. In one embodiment, the $K_d$ for a ZFP is measured using an electrophoretic mobility shift assay ("EMSA"), as described, for example, in WO 00/441566 and WO 00/42219.

"Administering" an expression vector, nucleic acid, ZFP, or a delivery vehicle to a cell comprises transducing, transfecting, electroporating, translocating, fusing, phagocytosing, shooting or ballistic methods, etc., i.e., any means by which a protein or nucleic acid can be transported across a cell membrane and preferably into the nucleus of a cell.

The term "effective amount" includes that amount which results in the desired result, for example, repression of an active gene, activation of a repressed gene, or inhibition of transcription of a structural gene or translation of RNA.

A "delivery vehicle" refers to a compound, e.g., a liposome, toxin, or a membrane translocation polypeptide, which is used to administer an exogenous molecule. Delivery vehicles can be used, for example, to administer nucleic acids encoding fusion molecules such as, for example ZFP-localization domain fusions. Exemplary delivery vehicles include lipid:nucleic acid complexes, expression vectors, viruses, and the like.

The term "modulate" refers to a change in the quantity, degree or extent of a function. For example, the modified zinc finger-nucleotide binding polypeptides disclosed herein may modulate the activity of a promoter sequence by binding to a motif within the promoter, thereby inducing, enhancing or suppressing transcription of a gene operatively linked to the promoter sequence. Alternatively, modulation may include inhibition of transcription of a gene wherein the modified zinc finger-nucleotide binding polypeptide binds to the structural gene and blocks DNA dependent RNA polymerase from reading through the gene, thus inhibiting transcription of the gene. The structural gene may be a normal cellular gene or an oncogene, for example. Alternatively, modulation may include inhibition of translation of a transcript. Thus, "modulation" of gene expression includes both gene activation and gene repression.

Modulation can be assayed by determining any parameter that is indirectly or directly affected by the expression of the target gene. Such parameters include, e.g., changes in RNA or protein levels; changes in protein activity; changes in product levels; changes in downstream gene expression; changes in transcription or activity of reporter genes such as, for example, luciferase, CAT, beta-galactosidase, or GFP (see, e.g., Mistili & Spector, (1997) *Nature Biotechnology* 15:961–964); changes in signal transduction; changes in phosphorylation and dephosphorylation; changes in receptor-ligand interactions; changes in concentrations of second messengers such as, for example, cGMP, cAMP, $IP_3$, and $Ca^{2+}$; changes in cell growth, changes in neovascularization, and/or changes in any functional effect of gene expression. Measurements can be made in vitro, in vivo, and/or ex vivo. Such functional effects can be measured by conventional methods, e.g., measurement of RNA or protein levels, measurement of RNA stability, and/or identification of downstream or reporter gene expression. Readout can be by way of, for example, chemiluminescence, fluorescence, colorimetric reactions, antibody binding, inducible markers, ligand binding assays; changes in intracellular second messengers such as cGMP and inositol triphosphate ($IP_3$); changes in intracellular calcium levels; cytokine release, and the like.

Accordingly, the terms "modulating expression" "inhibiting expression" and "activating expression" of a gene can refer to the ability of a molecule to activate or inhibit transcription of a gene. Activation includes prevention of transcriptional inhibition (i.e., prevention of repression of gene expression) and inhibition includes prevention of transcriptional activation (i.e., prevention of gene activation).

To determine the level of gene expression modulation by a ZFP, cells contacted with ZFPs are compared to control cells, e.g., without the zinc finger protein or with a non-specific ZFP, to examine the extent of inhibition or activation. Control samples are assigned a relative gene expression activity value of 100%. Modulation/inhibition of gene expression is achieved when the gene expression activity value relative to the control is about 80%, preferably 50% (i.e., 0.5× the activity of the control), more preferably 25%, more preferably 5–0%. Modulation/activation of gene expression is achieved when the gene expression activity value relative to the control is 110%, more preferably 150% (i.e., 1.5× the activity of the control), more preferably 200–500%, more preferably 1000–2000% or more.

A "promoter" is defined as an array of nucleic acid control sequences that direct transcription. As used herein, a promoter typically includes necessary nucleic acid sequences near the start site of transcription, such as, in the case of certain RNA polymerase II type promoters, a TATA element, enhancer, CCAAT box, SP-1 site, etc. As used herein, a promoter also optionally includes distal enhancer or repressor elements, which can be located as much as several thousand base pairs from the start site of transcription. The promoters often have an element that is responsive to transactivation by a DNA-binding moiety such as a polypeptide, e.g., a nuclear receptor, Gal4, the lac repressor and the like.

A "constitutive" promoter is a promoter that is active under most environmental and developmental conditions. An "inducible" promoter is a promoter that is active under certain environmental or developmental conditions.

A "regulatory domain" or "functional domain" refers to a protein or a polypeptide sequence (or portion thereof) that has transcriptional modulation activity, or that is capable of interacting with proteins and/or protein domains that have transcriptional modulation activity. Such proteins include, e.g., transcription factors and co-factors (e.g., KRAB, MAD, ERD, SID, nuclear factor kappa B subunit p65, early growth response factor 1, and nuclear hormone receptors, VP 16, VP64), endonucleases, integrases, recombinases, methyltransferases, histone acetyltransferases, histone deacetylases and polypeptides which are components of a chromatin remodeling complex, and their functional fragments. Exemplary components of chromatin remodeling complexes are disclosed in co-owned PCT/US01/40616, the disclosure of which is incorporated by reference herein in its entirety. A functional domain can be covalently or non-covalently linked to a DNA-binding domain (e.g., a ZFP) to modulate transcription of a gene of interest. Alternatively, some binding domains, such as for example ZFPs can act in the absence of a functional domain to modulate transcription. Furthermore, transcription of a gene of interest can be modulated by a binding domain, such as a ZFP, linked to multiple functional domains.

The term "heterologous" is a relative term, which when used with reference to portions of a nucleic acid indicates that the nucleic acid comprises two or more subsequences that are not found in the same relationship to each other in nature. For instance, a nucleic acid that is recombinantly produced typically has two or more sequences from unrelated genes synthetically arranged to make a new functional nucleic acid, e.g., a promoter from one source and a coding region from another source. The two nucleic acids are thus heterologous to each other in this context. When added to a cell, the recombinant nucleic acids would also be heterologous to the endogenous genes of the cell. Thus, in a cell, a heterologous nucleic acid would include a recombinant nucleic acid that has integrated into the chromosome, or a recombinant extrachromosomal nucleic acid.

Similarly, a heterologous protein indicates that the protein comprises two or more subsequences that are not found in the same relationship to each other in nature (e.g., a "fusion protein," where the two subsequences are encoded by a single nucleic acid sequence). See, e.g., Ausubel, supra, for an introduction to recombinant techniques.

By "host cell" is meant a cell that contains one or more exogenous molecules such as, for example, expression vectors and/or heterologous nucleic acids. The host cell typically supports the replication or expression of an expression vector. Host cells may be prokaryotic cells such as *E. coli*, or eukaryotic cells such as fungal cells (e.g., yeast), protozoal cells, plant cells, insect cells, animal cells, avian cells, teleost cells, amphibian cells, mammalian cells, primate cells or human cells. Exemplary mammalian cell lines include CHO, HeLa, 293, COS-1, and the like, e.g., cultured cells (in vitro), explants and primary cultures (in vitro and ex vivo), and cells in vivo.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine, and methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605–2608 (1985); Rossolini et al., *Mol. Cell. Probes* 8:91–98 (1994)). Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon in an amino acid herein, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid and nucleic acid sequences, individual substitutions, deletions or additions that alter, add or delete a single amino acid or nucleotide or a small percentage of amino acids or nucleotides in the sequence create a "conservatively modified variant," where the alteration results in the substitution of an amino acid with a chemically similar amino acid. Conservative substitution tables providing functionally similar amino acids are well known in the art. Such conservatively modified variants are in addition to and do not exclude polymorphic variants and alleles. See, e.g., Creighton, *Proteins* (1984) for a discussion of amino acid properties.

Localization Domains

Transcriptionally inactive regions of chromatin (e.g., telomeres, heterochromatin, matrix attachment regions, scaffold attachment regions, centromeres) have been observed to occupy distinct nuclear addresses. See, for example, Cockell et al (1999) *Curr. Opin. Genet. Devel.* 9:199–205; Mahy et al. (2000) in "Chromatin Structure and Gene Expression," Second Edition (S. C. R. Elgin & J. L. Workman, eds.) Oxford University Press, Oxford. Pp. 300–321 and references therein. Thus, there exists, in at least some cases, a correlation between transcriptional activity and nuclear localization. Moreover, certain nuclear proteins have been observed to be localized to specific regions within the nucleus. For example, the HP1 protein is localized to regions of the nucleus that are rich in transcriptionally inactive heterochromatin. See, for example, Eissenberg et al. (2000) *Curr. Opin. Genet. Devel.* 10:204–210. This heterochromatic localization of HP1 is mediated, at least in part, by a region of the HP1 protein known as the chromodomain. See, for example, Platero et al (1995) *EMBO J.* 14:3977–3986. One property of HP1-type chromodomains is their ability to bind to histone H3 that is methylated at lysine 9. See, for example, Lachner et al. (2001) *Nature* 410:116–120. Thus, exemplary localization domains include HP1 and the chromodomain, which is also found in a number of other proteins in addition to HP1.

Additional examples of correlations between intranuclear localization and transcriptional regulatory activity are provided by certain proteins involved in generating and recognizing methylated chromosomal DNA. Methylation of cytosine within CpG dinucleotide sequences in chromosomal DNA often leads to transcriptional repression of genes associated with these methylated sequences. Two types of proteins are directly involved with CpG methylation: DNA-N-methyl transferases (DNMTs), which catalyze the methylation reaction, and methylated DNA binding proteins (known as MBDs because they possess a methylated DNA binding domain), which bind to methylated DNA and mediate certain transcriptional effects of DNA methylation. Both of these classes of proteins possess transcriptional regulatory activities in addition to their methylation, or methylated DNA-binding, activities. These additional activities are related to the ability of these proteins to recruit transcriptional regulatory and chromatin remodeling proteins and/or to localize to discrete nuclear compartments, thereby drawing bound DNA into the compartment in which the protein is localized.

Accordingly, additional exemplary localization domains include DNMTs and methylated DNA-binding domains (MBDs).

A. DNA-N-methyl Transferases

The DNA methyltransferases Dnmt3a and Dnmt3b are responsible for cytosine methylation of CpG dinucleotide sequences. CpG methylation is often associated with transcriptional repression, especially in the context of CpG islands located at or near the promoter of many mammalian genes. However, DNA methyltransferases also possess transcriptional repression activity that is independent of their ability to methylate DNA and which involves association with histone deacetylases (HDACs). See, e.g., Rountree et al. (2000) *Nature Genet.* 25:269277; Robertson et al. (2000) *Nature Genet.* 25:338–342; Fuks et al. (2001) *EMBO J.* 20:2536–2544. DNA methyltransferases are also able to localize to heterochromatic regions of the nucleus; this localizing ability resides in the N-terminal region of these proteins. See, for example, Bachman et al. (2001) *J. Biol. Chem.* 276:32,282–32,287. Thus, the transcriptional repression activity of DNMTs and related proteins is due, at least in part, to their ability to recruit HDACs and to localize DNA sequences to which they are bound to heterochromatic regions of the nucleus.

Accordingly, a DNMT, or functional fragment thereof, can serve as a localization domain in the practice of the disclosed methods and the use of the disclosed compositions. Exemplary DNMTs include, but are not limited to, DNMT1, DNMT2, DNMT3a, and DNMT3b. See also Robertson (2001) *Oncogene* 20:3139–3155.

B. Methyl Binding Domains

In vertebrates, methyl-CpG-binding domain proteins comprise two functional domains: one which binds to methylated CpG dinucleotides and one which appears to be involved in transcriptional silencing. It is known that components of certain chromatin remodeling complexes bind to methylated DNA. Chromatin remodeling complexes from human (NRD complex) and amphibian cells (Mi-2 complex) contain a nucleosome-dependent ATPase activity called Mi-2 (also known as CHD). Additional protein components of the amphibian Mi-2 complex include Mta1-like (a DNA-binding protein homologous to metastasis-associated protein), RPD3 (the amphibian homologue of histone deacetylases HDAC1 and HDAC2), RbAp48 (a protein which interacts with histone H4), and MBD3 (a protein containing a methylated CpG binding domain). The amphibian complex additionally contains a serine- and proline-rich subunit, p66. Activities of the amphibian Mi-2 complex include a nucleosome-dependent ATPase that is not stimulated by free histones or DNA, translational movement of histone octamers relative to DNA, and deacetylation of core histones within a nucleosome. Guschin et al. (2000) *Biochemistry* 39:5238–5245; Wade et al. (1999) *Nature Genet.* 23:62–66.

As described in the Examples below, Applicants have identified a structural motif in invertebrates (which lack DNA methylation) that is homologous to the vertebrate MBD and is a component of a Mi-2-like complex. The results described herein indicate that these MBDs fulfill additional functions besides binding methylated DNA. For example, invertebrate MBDs appear to be included in a chromatin remodeling complex (the Mi-2 complex, see Examples) and are also able to repress transcription when fused to the Gal4 DNA binding domain (see Examples). Thus, the term methyl CpG binding domain or "MBD" as used herein refers to polypeptides sharing the identified structural motif and functions (e.g., as components of chromatin remodeling complexes; as agents of transcriptional repression, corepressors, etc.). Accordingly, MBDs may, but need not, bind to methylated CpG residues.

The methylated DNA-binding proteins MBD2 and MBD3 have been shown to localize to heterochromatic regions of the nucleus. Hendrich et al. (1998) *Mol. Cell. Biol.* 18:6538–6547. Additional proteins which possess the ability to localize to heterochromatin include HP1 and DNA-N-methyl transferases (see supra). Accordingly, in one embodiment, the compositions and methods described herein are directed to using a localization domain to facilitate the recruitment of corepression complexes to a particular site within chromatin, by fusion of the localization domain to a DNA binding domain that can access such a site, thereby repressing gene activity. In other aspects, the localization domain is used to interfere with corepression complexes and function by constructing fusion molecules containing a localization domain, a DNA binding domain and one or more regulatory domains that influence gene expression (e.g., activation domains, repression domains and/or components of a chromatin remodeling complex).

Any MBD having the requisite function and specificity is suitable. Thus, the MBD can be from any species. In certain embodiments, the MBD is derived from *Drosophila* MBD family members, for example dMBD-like and dMBD-likeΔ proteins described in the Examples. In other embodiments, the MBD is derived from vertebrate (e.g., mammalian) MBD proteins, for example, MBD1, MBD2, MBD3, MBD4, MeCP1 and MeCP2. See, for example, Bird et al. (1999) *Cell* 99:451–454. To give but one example, the methylated DNA-binding protein MeCP2 comprises identifiable transcriptional repression functions and methylated DNA-binding functions, and localizes to heterochromatin. Nan et al. (1993) *Nucleic Acids Res.* 21:4886–4892. Accordingly, these regions of MeCP2 can be used as localization domains.

It will be clear from the disclosure that the term "localization domain," as used herein, refers to a molecule capable, either actively or passively, of taking up a particular intranuclear address, such address often constituting a nuclear compartment having specific characteristics related to transcriptional activity. The term is to be distinguished from the terms "nuclear localization sequence" and "nuclear localization signal" which refer to sequences responsible for transport of a polypeptide from the cytoplasm into the nucleus.

For the purposes of this disclosure, it is intended that the term "localization domain" additionally encompass those proteins or polypeptides, or functional fragments thereof, that associate or interact with a protein or protein domain capable of being localized. For example, the KRAB transcription regulatory domain interacts with the KAP-1 protein, which, in turn, interacts with HP1, which is localized to heterochromatin (see supra). Matsuda et al. (2001) *J. Biol. Chem.* 276:14,222–14,229. Accordingly, proteins such as KAP-1 and KRAB, as well as any other proteins capable of being localized, either intrinsically or through association with one or more additional proteins, can serve as a localization domain.

DNA-Binding Domains

In certain embodiments, the compositions and methods disclosed herein involve fusions between a DNA-binding domain and a localization domain. In additional embodiments, the compositions and methods disclosed herein involve fusions between a DNA-binding domain and a domain which participates in modulation of gene expression (i.e., a regulatory domain) such as, for example a transcriptional activation domain, a transcriptional repression domain or a component of a chromatin remodeling complex. A DNA-binding domain can comprise any molecular entity capable of sequence-specific binding to chromosomal DNA. Binding can be mediated by electrostatic interactions, hydrophobic interactions, or any other type of chemical interaction. Examples of moieties which can comprise part of a DNA-binding domain include, but are not limited to, minor groove binders, major groove binders, antibiotics, intercalating agents, peptides, polypeptides, oligonucleotides, and nucleic acids. An example of a DNA-binding nucleic acid is a triplex-forming oligonucleotide.

Minor groove binders include substances which, by virtue of their steric and/or electrostatic properties, interact preferentially with the minor groove of double-stranded nucleic acids. Certain minor groove binders exhibit a preference for particular sequence compositions. For instance, netropsin, distamycin and CC-1065 are examples of minor groove binders which bind specifically to AT-rich sequences, particularly runs of A or T. WO 96/32496.

Many antibiotics are known to exert their effects by binding to DNA. Binding of antibiotics to DNA is often sequence-specific or exhibits sequence preferences. Actinomycin, for instance, is a relatively GC-specific DNA binding agent.

In a preferred embodiment, a DNA-binding domain is a polypeptide. Certain peptide and polypeptide sequences bind to double-stranded DNA in a sequence-specific manner. For example, certain transcription factors participate in transcription initiation by RNA Polymerase II through sequence-specific interactions with DNA in the promoter and/or enhancer regions of genes. Defined regions within the polypeptide sequence of various transcription factors have been shown to be responsible for sequence-specific binding to DNA. See, for example, Pabo et al. (1992) $Ann. Rev. Biochem.$ 61:1053–1095 and references cited therein. These regions include, but are not limited to, motifs known as leucine zippers, helix-loop-helix (HLH) domains, helix-turn-helix domains, zinc fingers, β-sheet motifs, steroid receptor motifs, bZIP domains homeodomains, AT-hooks and others. The amino acid sequences of these motifs are known and, in some cases, amino acids that are critical for sequence specificity have been identified. Polypeptides involved in other process involving DNA, such as replication, recombination and repair, will also have regions involved in specific interactions with DNA. Peptide sequences involved in specific DNA recognition, such as those found in proteins involved in transcription, replication, recombination and repair, can be obtained through recombinant DNA cloning and expression techniques or by chemical synthesis, and can be attached to other components of a fusion molecule by methods known in the art.

In a more preferred embodiment, a DNA-binding domain comprises a zinc finger DNA-binding domain (ZFP). See, for example, Miller et al. (1985) $EMBO J.$ 4:1609–1614; Rhodes et al. (1993) $Scientific American$ Feb.:56–65; and Klug (1999) $J. Mol. Biol.$ 293:215–218. In one embodiment, a target site for a zinc finger DNA-binding domain is identified according to site selection rules disclosed in co-owned WO 00/42219. ZFP DNA-binding domains are designed and/or selected to recognize a particular target site as described in co-owned WO 00/42219 and WO 00/41566; as well as U.S. Pat. Nos. 5,789,538; 6,007,408; and 6,013,453; and PCT publications WO 95/19431, WO 98/53057, WO 98/53058, WO 98/53059, WO 98/53060, WO 98/54311, WO 00/23464 and WO 00/27878.

Certain DNA-binding domains are capable of binding to DNA that is packaged in nucleosomes. See, for example, Cordingley et al. (1987) $Cell$ 48:261–270; Pina et al. (1990) $Cell$ 60:719–731; and Cirillo et al. (1998) $EMBO J.$ 17:244–254. Certain ZFP-containing proteins such as, for example, members of the nuclear hormone receptor superfamily, are capable of binding DNA sequences packaged into chromatin. These include, but are not limited to, the glucocorticoid receptor and the thyroid hormone receptor. Archer et al. (1992) $Science$ 255:1573–1576; Wong et al. (1997) $EMBO J.$ 16:7130–7145. Other DNA-binding domains, including certain ZFP-containing binding domains, require more accessible DNA for binding. In the latter case, the binding specificity of the DNA-binding domain can be determined by identifying accessible regions in the cellular chromatin. Accessible regions can be determined as described, for example, in co-owned PCT/US01/13631 and PCT/US01/40617, the disclosures of which are incorporated by reference herein in their entireties. A DNA-binding domain is then designed and/or selected to bind to a target site within the accessible region.

Fusion Molecules

The discovery that localization domains are involved in transcriptional corepression complexes in different vertebrate and invertebrate species also allows for the design of fusion molecules which facilitate regulation of gene expression. Thus, in certain embodiments, the compositions and methods disclosed herein involve fusions between a DNA-binding domain and a localization domain (such as, for example, a MBD) or functional fragment, as described supra, or a polynucleotide encoding such a fusion. In this way, a localization domain is brought into proximity with a sequence in a gene that is bound by the DNA-binding domain. The transcriptional repression function of the localization domain is then able to act on the gene, by recruiting additional corepressors and/or by transporting the bound gene to a repressive compartment of the nucleus.

In additional embodiments, target remodeling of chromatin, as disclosed in co-owned PCT/US01/40606 (the disclosure of which is incorporated by reference herein in its entirety) can be used to generate one or more sites in cellular chromatin that are accessible to the binding of a localization domain/DNA binding domain fusion molecule.

Fusion molecules are constructed by methods of cloning and biochemical conjugation that are well-known to those of skill in the art. Fusion molecules comprise a DNA-binding domain and a localization domain or a functional fragment thereof. In certain embodiments, fusion molecules comprise a DNA-binding domain, a localization domain, and a regulatory domain (e.g., a transcriptional activation or repression domain or a component of a chromatin remodeling complex). Fusion molecules also optionally comprise nuclear localization signals (such as, for example, that from the SV40 medium T-antigen) and epitope tags (such as, for example, FLAG, myc and hemagglutinin). Fusion proteins (and nucleic acids encoding them) are designed such that the translational reading frame is preserved among the components of the fusion.

Fusions between a polypeptide component of a localization domain (or a functional fragment thereof) on the one hand, and a non-protein DNA-binding domain (e.g., antibiotic, intercalator, minor groove binder, nucleic acid) on the other, are constructed by methods of biochemical conjugation known to those of skill in the art. See, for example, the Pierce Chemical Company (Rockford, Ill.) Catalogue. Methods and compositions for making fusions between a minor groove binder and a polypeptide have been described. Mapp et al. (2000) $Proc. Natl. Acad. Sci. USA$ 97:3930–3935.

The fusion molecules disclosed herein comprise a DNA-binding domain which binds to a target site. In certain embodiments, the target site is present in an accessible region of cellular chromatin. Accessible regions can be determined as described, for example, in co-owned PCT/ US01/13631 and PCT/US01/40617, the disclosures of which are hereby incorporated by reference herein in their entireties. If the target site is not present in an accessible region of cellular chromatin, one or more accessible regions can be generated as described in co-owned PCT/US01/ 40616, the disclosure of which is hereby incorporated by reference herein in its entirety. In additional embodiments, the DNA-binding domain of a fusion molecule is capable of binding to cellular chromatin regardless of whether its target site is in an accessible region or not. For example, such DNA-binding domains are capable of binding to linker DNA and/or nucleosomal DNA. Examples of this type of "pioneer" DNA binding domain are found in certain steroid receptor and in hepatocyte nuclear factor 3 (HNF3). Cordingley et al. (1987) Cell 48:261–270; Pina et al. (1990) Cell 60:719–731; and Cirillo et al. (1998) EMBO J. 17:244–254.

Methods of chromatin modification or binding using a localization domain can be combined with methods involving binding of endogenous or exogenous transcriptional regulators in the region of interest to achieve modulation of gene expression. Modulation of gene expression can be in the form of repression as, for example, when the target gene resides in a pathological infecting microorganism or in an endogenous gene of the subject, such as an oncogene or a viral receptor, that contributes to a disease state. Further, as described supra, repression of a specific target gene can be achieved by using a fusion molecule comprising a localization domain (or functional fragment thereof) and a DNA-binding domain, for compartmentalizing the target DNA (and related gene) into a transcriptionally repressed nuclear location.

Alternatively, modulation can be in the form of activation, for example, if activation of a gene (e.g., a tumor suppressor gene) can ameliorate a disease state. In this case, a cell is contacted with a fusion molecule comprising, a localization domain, a DNA-binding domain and a transcriptional activation domain. The localization domain portion of the fusion molecule localizes it to the repressive compartment of the nucleus, where the DNA-binding domain is able to access the target gene. The activation domain is then able to activate transcription of the silenced gene, by removing it from the repressive nuclear compartment and/or by recruiting additional coactivators that overcome the repressive environment of the target gene. These embodiments are particularly suitable for the reactivation of genes whose expression has been silenced during development, as such developmental silencing mechanisms often depend upon methylation of the silenced gene.

A further exemplary method for reactivation of a gene located in a repressive nuclear compartment is to utilize a fusion comprising a localization domain, a DNA-binding domain and a component of a chromatin remodeling complex. In this case, the localization domain localizes the fusion molecule to a repressive nuclear compartment, in which the DNA-binding portion of the fusion molecule gains access to the target gene. The chromatin remodeling component is able to assemble an active chromatin remodeling complex on the target gene, resulting in modification of the chromatin structure on the target gene into a transcriptionally active conformation.

Additional embodiments involve the use of a fusion molecule comprising a DNA-binding domain and a localization domain, in combination with a second molecule having transcriptional regulatory activity which binds in the region of interest, to regulate expression of one or more target genes. In certain embodiments, the second molecule comprises a fusion between a DNA-binding domain and either a transcriptional activation domain or a transcriptional repression domain. Any polypeptide sequence or domain capable of influencing gene expression, which can be fused to a DNA-binding domain, is suitable for use. Activation and repression domains are known to those of skill in the art and are disclosed, for example, in co-owned WO 00/41566.

Exemplary activation domains include, but are not limited to, VP16, VP64, p300, CBP, PCAF, SRC1 PvALF, AtHD2A and ERF-2. See, for example, Robyr et al. (2000) Mol Endocrinol. 14:329–347; Collingwood et al. (1999) J. Mol. Endocrinol. 23:255–275; Leo et al. (2000) Gene 245:1–11; Manteuffel-Cymborowska (1999) Acta Biochim. Pol. 46:77–89; McKenna et al. (1999) J. Steroid Biochem. Mol. Biol. 69:3–12; Malik et al. (2000) Trends Biochem. Sci. 25:277–283; and Lemon et al. (1999) Curr. Opin. Genet. Dev. 9:499–504. Additional exemplary activation domains include, but are not limited to, OsGAI, HALF-1, C1, AP1, ARF-5, -6, -7, and -8, CPRF1, CPRF4, MYC-RP/GP, and TRAB1. See, for example, Ogawa et al. (2000) Gene 245:21–29; Okanami et al. (1996) Genes Cells 1:87–99; Goff et al. (1991) Genes Dev. 5:298–309; Cho et al. (1999) Plant Mol. Biol. 40:419–429; Ulmason et al. (1999) Proc. Natl. Acad. Sci. USA 96:5844–5849; Sprenger-Haussels et al. (2000) Plant J. 22:1–8; Gong et al. (1999) Plant Mol. Biol. 41:33–44; and Hobo et al. (1999) Proc. Natl. Acad. Sci. USA 96:15,348–15,353.

Exemplary repression domains include, but are not limited to, KRAB, SID, MBD2, MBD3, members of the DNMT family (e.g., DNMT1, DNMT3A, DNMT3B), Rb, and MeCP2. See, for example, Bird et al. (1999) Cell 99:451–454; Tyler et al. (1999) Cell 99:443–446; Knoepfler et al. (1999) Cell 99:447–450; and Robertson et al. (2000) Nature Genet. 25:338–342. Additional exemplary repression domains include, but are not limited to, ROM2 and AtHD2A. See, for example, Chern et al. (1996) Plant Cell 8:305–321; and Wu et al. (2000) Plant J. 22:19–27.

Common regulatory domains for use in a fusion molecule include, e.g., effector domains from transcription factors (activators, repressors, co-activators, co-repressors), silencers, nuclear hormone receptors, oncogene transcription factors (e.g., myc, jun, fos, myb, max, mad, rel, ets, bcl, myb, mos family members etc.); DNA repair enzymes and their associated factors and modifiers; DNA rearrangement enzymes and their associated factors and modifiers; chromatin associated proteins and their modifiers (e.g., kinases, acetylases and deacetylases); and DNA modifying enzymes (e.g., methyltransferases, topoisomerases, helicases, ligases, kinases, phosphatases, polymerases, endonucleases) and their associated factors and modifiers.

Transcription factor polypeptides from which one can obtain a regulatory domain include those that are involved in regulated and basal transcription. Such polypeptides include transcription factors, their effector domains, coactivators, silencers, nuclear hormone receptors (see, e.g., Goodrich et al., Cell 84:825–30 (1996) for a review of proteins and nucleic acid elements involved in transcription; transcription factors in general are reviewed in Barnes & Adcock, Clin. Exp. Allergy 25 Suppl. 2:46–9 (1995) and Roeder, Methods Enzymol. 273:165–71 (1996)). Databases dedicated to transcription factors are known (see, e.g., Science 269:630 (1995)). Nuclear hormone receptor transcription factors are described in, for example, Rosen et al., J. Med. Chem. 38:4855–74 (1995). The C/EBP family of transcription factors are reviewed in Wedel et al., Immunobiology 193:171–85 (1995). Coactivators and co-repressors that mediate transcription regulation by nuclear hormone receptors are reviewed in, for example, Meier, *Eur. J. Endocrinol.* 134(2):158–9 (1996); Kaiser et al., *Trends Biochem. Sci.* 21:342–5 (1996); and Utley et al., *Nature* 394:498–502 (1998)). GATA transcription factors, which are involved in regulation of hematopoiesis, are described in, for example, Simon, *Nat. Genet.* 11:9–11(1995); Weiss et al., *Exp. Hematol.* 23:99–107. TATA box binding protein (TBP) and its associated TAF polypeptides (which include TAF30, TAF55, TAF80, TAF110, TAF150, and TAF250) are described in Goodrich & Tjian, *Curr. Opin. Cell Biol.* 6:403–9 (1994) and Hurley, *Curr. Opin. Struct. Biol.* 6:69–75 (1996). The STAT family of transcription factors are reviewed in, for example, Barahmand-Pour et al., *Curr. Top. Microbiol. Immunol.* 211:121–8 (1996). Transcription factors involved in disease are reviewed in Aso et al.,*J. Clin. Invest.* 97:1561–9 (1996).

In one embodiment, the KRAB repression domain from the human KOX-1 protein is used as a repression domain (Thiesen et al., *New Biologist* 2:363–374 (1990); Margolin et al., *PNAS* 91:4509–4513 (1994); Pengue et al., *Nucl. Acids Res.* 22:2908–2914 (1994); Witzgall et al., *PNAS* 91:4514–4518 (1994); see also Example 3)). In another embodiment, KAP-1, a KRAB co-repressor, is used with KRAB (Friedman et al., *Genes Dev.* 10:2067–2078 (1996)). Other preferred transcription factors and transcription factor domains that act as transcriptional repressors include MAD (see, e.g., Sommer et al., *J. Biol. Chem.* 273:6632–6642 (1998); Guptaetal., *Oncogene* 16:1149–1159 (1998); Queva et al., *Oncogene* 16:967–977 (1998); Larsson et al., *Oncogene* 15:737–748 (1997); Laherty et al., *Cell* 89:349–356 (1997); and Cultraro et al., *Mol Cell. Biol.* 17:2353–2359 (19977)); FKHR (forkhead in rhapdosarcoma gene; Ginsberg et al., *Cancer Res.* 15:3542–3546 (1998); Epstein et al., *Mol. Cell. Biol.* 18:4118–4130 (1998)); EGR-1 (early growth response gene product-1; Yan et al., *PNAS* 95:8298–8303 (1998); and Liu et al., *Cancer Gene Ther.* 5:3–28 (1998)); the ets2 repressor factor repressor domain (ERD; Sgouras et al., *EMBO J.* 14:4781–4793 ((19095)); and the MAD smSIN3 interaction domain (SID; Ayer et al., *Mol. Cell. Biol.* 16:5772–5781 (1996)).

In one embodiment, the HSV VP16 activation domain is used as a transcriptional activator (see, e.g., Hagmann et al., *J. Virol.* 71:5952–5962 (1997)). Other preferred transcription factors that could supply activation domains include the VP64 activation domain (Seipel et al., *EMBO J.* 11:4961–4968 (1996)); nuclear hormone receptors (see, e.g., Torchia et al., *Curr. Opin. Cell. Biol.* 10:373–383 (1998)); the p65 subunit of nuclear factor kappa B (Bitko & Barik,*J. Virol.* 72:5610–5618 (1998) and Doyle & Hunt, *Neuroreport* 8:2937–2942 (1997)); and EGR-1 (early growth response gene product-1; Yan et al., *PNAS* 95:8298–8303 (1998); and Liu et al., *Cancer Gene Ther.* 5:3–28 (1998)).

Kinases, phosphatases, and other proteins that modify polypeptides involved in gene regulation are also useful as regulatory domains for use in fusion molecules. Such modifiers are often involved in switching on or off transcription mediated by, for example, hormones. Kinases involved in transcription regulation are reviewed in Davis, *Mol. Reprod. Dev.* 42:459–67 (1995), Jackson et al., *Adv. Second Messenger Phosphoprotein Res.* 28:279–86 (1993), and Boulikas, *Crit. Rev. Eukaryot. Gene Expr.* 5:1–77 (1995), while phosphatases are reviewed in, for example, Schonthal & Semin, *Cancer Biol.* 6:239–48 (1995). Nuclear tyrosine kinases are described in Wang, *Trends Biochem. Sci.* 19:373–6 (1994).

As described, useful domains can also be obtained from the gene products of oncogenes (e.g., myc, jun, fos, myb, max, mad, rel, ets, bcl, myb, mos, erb family members) and their associated factors and modifiers. Oncogenes are described in, for example, Cooper, *Oncogenes,* 2nd ed., The Jones and Bartlett Series in Biology, Boston, Mass., Jones and Bartlett Publishers, 1995. The ets transcription factors are reviewed in Waslylk et al., *Eur. J. Biochem.* 211:7–18 (1993) and Crepieux et al., *Crit. Rev. Oncog.* 5:615–38 (1994). Myc oncogenes are reviewed in, for example, Ryan et al., *Biochem. J.* 314:713–21 (1996). The jun and fos transcription factors are described in, for example, *The Fos and Jun Families of Transcription Factors*, Angel & Herrlich, eds. (1994). The max oncogene is reviewed in Hurlin et al., Cold Spring Harb. Symp. Quant. Biol. 59:109–16. The myb gene family is reviewed in Kanei-Ishii et al., *Curr. Top. Microbiol. Immunol.* 211:89–98 (1996). The mos family is reviewed in Yew et al., *Curr. Opin. Genet. Dev.* 3:19–25 (1993).

Regulatory domains can also be obtained from DNA replication and repair enzymes and their associated factors and modifiers. DNA repair systems are reviewed in, for example, Vos, *Curr. Opin. Cell Biol.* 4:385–95 (1992); Sancar, *Ann. Rev. Genet.* 29:69–105 (1995); Lehmann, *Genet. Eng.* 17:1–19 (1995); and Wood,*Ann. Rev. Biochem.* 65:135–67 (1996). DNA rearrangement enzymes and their associated factors and modifiers can also be used as regulatory domains (see, e.g., Gangloff et al., *Experientia* 50:261–9 (1994); Sadowski, *FASEB J.* 7:760–7 (1993)).

Similarly, regulatory domains can be derived from DNA modifying enzymes (e.g., DNA methyltransferases, topoisomerases, helicases, ligases, kinases, phosphatases, polymerases) and their associated factors and modifiers. Helicases are reviewed in Matson et al., *Bioessays,* 16:13–22 (1994), and methyltransferases are described in Cheng, *Curr. Opin. Struct. Biol.* 5:4–10 (1995). Chromatin associated proteins and their modifiers (e.g., kinases, methylases, acetylases and deacetylases), such as histone deacetylase (Wolffe, *Science* 272:371–2 (1996)) are also useful as regulatory domains for use in a fusion molecule. In one embodiment, the regulatory domain is a DNA methyl transferase that acts as a transcriptional repressor (see, e.g., Van den Wyngaert et al., *FEBS Lett.* 426:283–289 (1998); Flynn et al.,*J. Mol. Biol.* 279:101–116 (1998); Okano et al., *Nucleic Acids Res.* 26:2536–2540 (1998); and Zardo & Caiafa,*J. Biol. Chem.* 273:16517–16520 (1998)). In another embodiment, endonucleases such as Fok1 are used as transcriptional repressors, which act via gene cleavage (see, e.g., WO 94/18313 and WO95/09233).

Factors that control chromatin and DNA structure, movement and localization and their associated factors and modifiers; factors derived from microbes (e.g., prokaryotes, eukaryotes and virus) and factors that associate with or modify them can also be used in the synthesis of fusion molecules. In one embodiment, recombinases and integrases are used as regulatory domains. In one embodiment, histone acetyltransferase is used as a transcriptional activator (see, e.g., Jin & Scotto, *Mol. Cell. Biol.* 18:4377–4384 (1998); Wolffe,*Science* 272:371–372 (1996); Taunton et al., *Science* 272:408–411 (1996); and Hassig et al.,*PNAS* 95:3519–3524 (1998)). In another embodiment, histone deacetylase is used as a transcriptional repressor (see, e.g., Jin & Scotto, *Mol. Cell. Biol.* 18:4377–4384 (1998); Syntichaki & Thireos, *J. Biol. Chem.* 273:24414–24419 (1998); Sakaguchi et al., *Genes Dev.* 12:2831–2841 (1998); and Martinez et al., *J. Biol. Chem.* 273:23781–23785 (1998)).

Another suitable repression domain is methyl binding domain protein 2B (MBD-2B) (see, also Hendrich et al. (1999) *Mamm Genome* 10:906–912 for description of MBD proteins). Another useful repression domain is that associated with the v-ErbA protein (see infra). See, for example, Damm, et al. (1989) *Nature* 339:593–597; Evans (1989) *Int. J. Cancer Suppl.* 4:26–28; Pain et al. (1990) *New Biol.* 2:284–294; Sap et al. (1989) *Nature* 340:242–244; Zenke et al. (1988) *Cell* 52:107–119; and Zenke et al. (1990) *Cell* 61:1035–1049. Additional exemplary repression domains include, but are not limited to, thyroid hormone receptor (TR, see infra), SID, MBD1, MBD2, MBD3, MBD4, MBD-like proteins, members of the DNMT family (e.g., DNMT1, DNMT3A, DNMT3B), Rb, MeCP1 and MeCP2. See, for example, Bird et al. (1999) *Cell* 99:451–454; Tyler et al. (1999) *Cell* 99:443–446; Knoepfler et al. (1999) *Cell* 99:447–450; and Robertson et al. (2000) *Nature Genet.* 25:338–342. Additional exemplary repression domains include, but are not limited to, ROM2 and AtHD2A. See, for example, Chern et al. (1996) *Plant Cell* 8:305–321; and Wu et al. (2000) *Plant J.* 22:19–27.

Certain members of the nuclear hormone receptor (NHR) superfamily, including, for example, thyroid hormone receptors (TRs) and retinoic acid receptors (RARs) are among the most potent transcriptional regulators currently known. Zhang et al., *Annu. Rev. Physiol.* 62:439–466 (2000) and Sucov et al., *Mol Neurobiol* 10(2–3):169–184 (1995). In the absence of their cognate ligand, these proteins bind with high specificity and affinity to short stretches of DNA (e.g., 12–17 base pairs) within regulatory loci (e.g., enhancers and promoters) and effect robust transcriptional repression of adjacent genes. The potency of their regulatory action stems from the concurrent use of two distinct functional pathways to drive gene silencing: (i) the creation of a localized domain of repressive chromatin via the targeting of a complex between the corepressor N-CoR and a histone deacetylase, HDAC3 (Guenther et al., *Genes Dev* 14:1048–1057 (2000); Urnov et al., *EMBO J* 19:4074–4090 (2000); Li et al, *EMBO J* 19, 4342–4350 (2000) and Underhill et al., *J. Biol. Chem.* 275:40463–40470 (2000)) and (ii) a chromatin-independent pathway (Urnov et al., supra) that may involve direct interference with the function of the basal transcription machinery (Fondell et al., *Genes Dev* 7(7B):1400–1410 (1993) and Fondell et al., *Mol Cell Biol* 16:281–287 (1996).

In the presence of very low (e.g., nanomolar) concentrations of their ligand, these receptors undergo a conformational change which leads to the release of corepressors, recruitment of a different class of auxiliary molecules (e.g., coactivators) and potent transcriptional activation. Collingwood et al., *J. Mol. Endocrinol.* 23(3):255–275 (1999).

The portion of the receptor protein responsible for transcriptional control (e.g., repression and activation) can be physically separated from the portion responsible for DNA binding, and retains full functionality when tethered to other polypeptides, for example, other DNA-binding domains. Accordingly, a nuclear hormone receptor transcription control domain can be used as a portion of a fusion molecule, such that the transcriptional regulatory activity of the receptor can be targeted to a chromosomal region of interest (e.g., a gene) by virtue of a DNA-binding domain (e.g., a ZFP binding domain).

Moreover, the structure of TR and other nuclear hormone receptors can be altered, either naturally or through recombinant techniques, such that it loses all capacity to respond to hormone (thus losing its ability to drive transcriptional activation), but retains the ability to effect transcriptional repression. This approach is exemplified by the transcriptional regulatory properties of the oncoprotein v-ErbA. The v-ErbA protein is one of the two proteins required for leukemic transformation of immature red blood cell precursors in young chicks by the avian erythroblastosis virus. TR is a major regulator of erythropoiesis (Beug et al., *Biochim Biophys Acta* 1288(3):M35–47 (1996); in particular, in its unliganded state, it represses genes required for cell cycle arrest and the differentiated state. Thus, the administration of thyroid hormone to immature erythroblasts leads to their rapid differentiation. The v-ErbA oncoprotein is an extensively mutated version of TR; these mutations include: (i) deletion of 12 amino-terminal amino acids; (ii) fusion to the gag oncoprotein; (iii) several point mutations in the DNA binding domain that alter the DNA binding specificity of the protein relative to its parent, TR, and impair its ability to heterodimerize with the retinoid X receptor; (iv) multiple point mutations in the ligand-binding domain of the protein that effectively eliminate the capacity to bind thyroid hormone; and (v) a deletion of a carboxy-terminal stretch of amino acids that is essential for transcriptional activation. Stunnenberg et al., *Biochim Biophys Acta* 1423(1):F15–33 (1999). As a consequence of these mutations, v-ErbA retains the capacity to bind to naturally occurring TR target genes and is an effective transcriptional repressor when bound (Urnov et al., supra; Sap et al., *Nature* 340:242–244 (1989); and Ciana et al., *EMBO J.* 17(24):7382–7394 (1999). In contrast to TR, however, v-ErbA is completely insensitive to thyroid hormone, and thus maintains transcriptional repression in the face of a challenge from any concentration of thyroids or retinoids, whether endogenous to the medium, or added by the investigator.

This functional property of v-ErbA is retained when its repression domain is fused to a heterologous, synthetic DNA binding domain. Accordingly, in one aspect, v-ErbA or its functional fragments are used as a repression domain. In additional embodiments, TR or its functional domains are used as a repression domain in the absence of ligand and/or as an activation domain in the presence of ligand (e.g., 3,5,3'-triiodo-L-thyronine or T3). Thus, TR can be used as a switchable functional domain (i.e., a bifunctional domain); its activity (activation or repression) being dependent upon the presence or absence (respectively) of ligand.

Additional exemplary repression domains are obtained from the DAX protein and its functional fragments. Zazopoulos et al., *Nature* 390:311–315 (1997). In particular, the C-terminal portion of DAX-1, including amino acids 245–470, has been shown to possess repression activity. Altincicek et al., *J. Biol. Chem.* 275:7662–7667 (2000). A further exemplary repression domain is the RBP1 protein and its functional fragments. Lai et al., *Oncogene* 18:2091–2100 (1999); Lai et al., *Mol. Cell. Biol.* 19:6632–6641 (1999); Lai et al., *Mol. Cell. Biol.* 21:2918–2932 (2001) and WO 01/04296. The full-length RBP1 polypeptide contains 1257 amino acids. Exemplary functional fragments of RBP1 are a polypeptide comprising amino acids 1114–1257, and a polypeptide comprising amino acids 243–452.

Members of the TIEG family of transcription factors contain three repression domains known as R1, R2 and R3. Repression by TIEG family proteins is achieved at least in part through recruitment of mSIN3A histone deacetylases complexes. Cook et al. (1999) *J. Biol. Chem.* 274:29, 500–29,504; Zhang et al. (2001) *Mol. Cell. Biol.* 21:5041–5049. Any or all of these repression domains (or their functional fragments) can be fused alone, or in combination with additional repression domains (or their functional fragments), to a DNA-binding domain to generate a targeted exogenous repressor molecule.

Furthermore, the product of the human cytomegalovirus (HCMV) UL34 open reading frame acts as a transcriptional repressor of certain HCMV genes, for example, the US3 gene. LaPierre et al. (2001) *J. Virol.* 75:6062–6069. Accordingly, the UL34 gene product, or functional fragments thereof, can be used as a component of a fusion molecule. Nucleic acids encoding such fusions are also useful in the methods and compositions disclosed herein.

Yet another exemplary repression domain is the CDF-1 transcription factor and/or its functional fragments. See, for example, WO 99/27092.

The Ikaros family of proteins are involved in the regulation of lymphocyte development, at least in part by transcriptional repression. Accordingly, an Ikaros family member (e.g., Ikaros, Aiolos) or a functional fragment thereof, can be used as a repression domain. See, for example, Sabbattini et al. (2001) *EMBO J.* 20:2812–2822.

The yeast Ash1p protein comprises a transcriptional repression domain. Maxon et al. (2001) *Proc. Natl. Acad. Sci. USA* 98:1495–1500. Accordingly, the Ash1p protein, its functional fragments, and homologues of Ash1p, such as those found, for example, in, vertebrate, mammalian, and plant cells, can serve as a repression domain for use in the methods and compositions disclosed herein.

Additional exemplary repression domains include those derived from histone deacetylases (HDACs, e.g., Class I HDACs, Class II HDACs, SIR-2 homologues), HDAC-interacting proteins (e.g., SIN3, SAP30, SAP15, NCoR, SMRT, RB, p107, p130, RBAP46/48, MTA, Mi-2, Brg1, Brm), DNA-cytosine methyltransferases (e.g., Dnmt1, Dnmt3a, Dnmt3b), proteins that bind methylated DNA (e.g., MBD1, MBD2, MBD3, MBD4, MeCP2, DMAP1), protein methyltransferases (e.g., lysine and arginine methylases, SuVar homologues such as Suv39H1), polycomb-type repressors (e.g., Bmi-1, eed1, RING1, RYBP, E2F6, Mel18, YY1 and CtBP), viral repressors (e.g., adenovirus E1b 55K protein, cytomegalovirus UL34 protein, viral oncogenes such as v-erbA), hormone receptors (e.g., Dax-1, estrogen receptor, thyroid hormone receptor), and repression domains associated with naturally-occurring zinc finger proteins (e.g., WT1, KAP1). Further exemplary repression domains include members of the polycomb complex and their homologues, HPH1, HPH2, HPC2, NC2, groucho, Eve, tramtrak, mHP1, SIP1, ZEB1, ZEB2, and Enx1/Ezh2. In all of these cases, either the full-length protein or a functional fragment can be used as a repression domain in a fusion molecule. Furthermore, any homologues of the aforementioned proteins can also be used as repression domains, as can proteins (or their functional fragments) that interact with any of the aforementioned proteins.

Additional repression domains, and exemplary functional fragments, are as follows. Hes1 is a human homologue of the *Drosophila hairy* gene product and comprises a functional fragment encompassing amino acids 910–1014. In particular, a WRPW (trp-arg-pro-trp) motif can act as a repression domain. Fisher et al. (1996) *Mol. Cell. Biol.* 16:2670–2677.

The TLE1, TLE2 and TLE3 proteins are human homologues of the *Drosophila groucho* gene product. Functional fragments of these proteins possessing repression activity reside between amino acids 1–400. Fisher et al., supra.

The Tbx3 protein possesses a functional repression domain between amino acids 524–721. He et al. (1999) *Proc. Natl. Acad. Sci. USA* 96:10,212–10,217. The Tbx2 gene product is involved in repression of the p14/p16 genes and contains a region between amino acids 504–702 that is homologous to the repression domain of Tbx3; accordingly Tbx2 and/or this functional fragment can be used as a repression domain. Carreira et al. (1998) *Mol. Cell. Biol.* 18:5,099–5,108.

The human Ezh2 protein is a homologue of *Drosophila* enhancer of zeste and recruits the eed1 polycomb-type repressor. A region of the Ezh2 protein comprising amino acids 1–193 can interact with eed1 and repress transcription; accordingly Ezh2 and/or this functional fragment can be used as a repression domain. Denisenko et al. (1998) *Mol. Cell. Biol.* 18:5634–5642.

The RYBP protein is a corepressor that interacts with polycomb complex members and with the YY1 transcription factor. A region of RYBP comprising amino acids 42–208 has been identified as functional repression domain. Garcia et al. (1999) *EMBO J.* 18:3404–3418.

The RING finger protein RING1A is a member of two different vertebrate polycomb-type complexes, contains multiple binding sites for various components of the polycomb complex, and possesses transcriptional repression activity. Accordingly, RING1A or its functional fragments can serve as a repression domain. Satjin et al. (1997) *Mol. Cell. Biol.* 17:4105–4113.

The Bmi-1 protein is a member of a vertebrate polycomb complex and is involved in transcriptional silencing. It contains multiple binding sites for various polycomb complex components. Accordingly, Bmi-1 and its functional fragments are useful as repression domains. Gunster et al. (1997) *Mol. Cell. Biol.* 17:2326–2335; Hemenway et al. (1998) *Oncogene* 16:2541–2547.

The E2F6 protein is a member of the mammalian Bmi-1-containing polycomb complex and is a transcriptional repressor that is capable or recruiting RYBP, Bmi-1 and RING1A. A functional fragment of E2F6 comprising amino acids 129–281 acts as a transcriptional repression domain. Accordingly, E2F6 and its functional fragments can be used as repression domains. Trimarchi et al. (2001) *Proc Natl. Acad. Sci. USA* 98:1519–1524.

The eed1 protein represses transcription at least in part through recruitment of histone deacetylases (e.g., HDAC2). Repression activity resides in both the N- and C-terminal regions of the protein. Accordingly, eed1 and its functional fragments can be used as repression domains. van der Vlag et al. (1999) *Nature Genet.* 23:474–478.

The CTBP2 protein represses transcription at least in part through recruitment of an HPC2-polycomb complex. Accordingly, CTBP2 and its functional fragments are useful as repression domains. Richard et al. (1999) *Mol. Cell. Biol.* 19:777–787.

Neuron-restrictive silencer factors are proteins that repress expression of neuron-specific genes. Accordingly, a NRSF or functional fragment thereof can serve as a repression domain. See, for example, U.S. Pat. No. 6,270,990.

It will be clear to those of skill in the art that, in the formation of a fusion protein (or a nucleic acid encoding same) between a DNA-binding domain and a regulatory domain, either a repressor or a molecule that interacts with a repressor is suitable as a repression domain. Essentially any molecule capable of recruiting a repressive complex and/or repressive activity (such as, for example, histone deacetylation) to the target gene is useful as a repression domain of a fusion protein.

Additional exemplary activation domains include, but are not limited to, p300, CBP, PCAF, SRC1 PvALF, AtHD2A and ERF-2. See, for example, Robyr et al. (2000) Mol. Endocrinol. 14:329–347; Collingwood et al. (1999) J. Mol. Endocrinol. 23:255–275; Leo et al. (2000) Gene 245:1–11;

Manteuffel-Cymborowska (1999) Acta Biochim. Pol. 46:77–89; McKenna et al. (1999) J. Steroid Biochem. Mol. Biol. 69:3–12; Malik et al. (2000) Trends Biochem. Sci. 25:277–283; and Lemon et al. (1999) Curr. Opin. Genet. Dev. 9:499–504. Additional exemplary activation domains include, but are not limited to, OsGAI, HALF-1, C1, AP1, ARF-5, -6, -7, and -8, CPRF1, CPRF4, MYC-RP/GP, and TRAB1. See, for example, Ogawa et al. (2000) Gene 245:21–29; Okanami et al. (1996) Genes Cells 1:87–99; Goff et al. (1991) Genes Dev. 5:298–309; Cho et al. (1999) Plant Mol. Biol. 40:419–429; Ulmason et al. (1999) Proc. Natl. Acad. Sci. USA 96:5844–5849; Sprenger-Haussels et al. (2000) Plant J. 22:1–8; Gong et al. (1999) Plant Mol. Biol. 41:33–44; and Hobo et al. (1999) Proc. Natl. Acad. Sci. USA 96:15,348–15,353.

It will be clear to those of skill in the art that, in the formation of a fusion protein (or a nucleic acid encoding same), either an activator or a molecule that interacts with an activator is suitable as a regulatory domain. Essentially any molecule capable of recruiting an activating complex and/or activating activity (such as, for example, histone acetylation) to the target gene is useful as an activating domain of a fusion molecule.

Chromatin remodeling proteins and components of chromatin remodeling complexes for use as regulatory domains in fusion molecules are described, for example, in co-owned PCT application US01/40616, the disclosure of which is hereby incorporated by reference in its entirety.

In a further embodiment, a DNA-binding domain (e.g., a zinc finger domain) is fused to a bifunctional domain (BFD). A bifunctional domain is a transcriptional regulatory domain whose activity depends upon interaction of the BFD with a second molecule. The second molecule can be any type of molecule capable of influencing the functional properties of the BFD including, but not limited to, a compound, a small molecule, a peptide, a protein, a polysaccharide or a nucleic acid. An exemplary BFD is the ligand binding domain of the estrogen receptor (ER). In the presence of estradiol, the ER ligand binding domain acts as a transcriptional activator; while, in the absence of estradiol and the presence of tamoxifen or 4-hydroxy-tamoxifen, it acts as a transcriptional repressor. Another example of a BFD is the thyroid hormone receptor (TR) ligand binding domain which, in the absence of ligand, acts as a transcriptional repressor and in the presence of thyroid hormone (T3), acts as a transcriptional activator. An additional BFD is the glucocorticoid receptor (GR) ligand binding domain. In the presence of dexamethasone, this domain acts as a transcriptional activator; while, in the presence of RU486, it acts as a transcriptional repressor. An additional exemplary BFD is the ligand binding domain of the retinoic acid receptor. In the presence of its ligand all-trans-retinoic acid, the retinoic acid receptor recruits a number of co-activator complexes and activates transcription. In the absence of ligand, the retinoic acid receptor is not capable of recruiting transcriptional co-activators. Additional BFDs are known to those of skill in the art. See, for example, U.S. Pat. Nos. 5,834,266 and 5,994,313 and PCT WO 99/10508.

In additional embodiments, a plurality of fusion molecules can be used in the disclosed methods. For example, a plurality of localization domain/DNA-binding domain fusions can be used; and a plurality of localization domain/DNA-binding domain/regulatory domain fusions can be used.

For these and other applications, exogenous molecules can be formulated with a pharmaceutically acceptable carrier, as is known to those of skill in the art. See, for example, Remington's Pharmaceutical Sciences, 17$^{th}$ ed., 1985; and co-owned WO 00/42219.

Polynucleotide and Polypeptide Delivery

The compositions described herein can be provided to the target cell in vitro or in vivo. In addition, the compositions can be provided as polypeptides, polynucleotides or combination thereof.

A. Delivery of Polynucleotides

In certain embodiments, the compositions are provided as one or more polynucleotides. Further, as noted above, a localization domain-containing composition can be designed as a fusion between a polypeptide DNA-binding domain and a localization domain and can be encoded by a fusion nucleic acid. In both fusion and non-fusion cases, the nucleic acid can be cloned into intermediate vectors for transformation into prokaryotic or eukaryotic cells for replication and/or expression. Intermediate vectors for storage or manipulation of the nucleic acid or production of protein can be prokaryotic vectors, (e.g., plasmids), shuttle vectors, insect vectors, or viral vectors for example. A nucleic acid encoding a localization domain or a localization domain fusion can also cloned into an expression vector, for administration to a bacterial cell, fungal cell, protozoal cell, plant cell, or animal cell, preferably a mammalian cell, more preferably a human cell.

To obtain expression of a cloned nucleic acid, it is typically subcloned into an expression vector that contains a promoter to direct transcription. Suitable bacterial and eukaryotic promoters are well known in the art and described, e.g., in Sambrook et al., supra; Ausubel et al., supra; and Kriegler, Gene Transfer and Expression: A Laboratory Manual (1990). Bacterial expression systems are available in, e.g., E. coli, Bacillus sp., and Salmonella. Palva et al. (1983) Gene 22:229–235. Kits for such expression systems are commercially available. Eukaryotic expression systems for mammalian cells, yeast, and insect cells are well known in the art and are also commercially available, for example, from Invitrogen, Carlsbad, Calif. and Clontech, Palo Alto, Calif.

The promoter used to direct expression of the nucleic acid of choice depends on the particular application. For example, a strong constitutive promoter is typically used for expression and purification. In contrast, when a dedifferentiation protein is to be used in vivo, either a constitutive or an inducible promoter is used, depending on the particular use of the protein. In addition, a weak promoter can be used, such as HSV TK or a promoter having similar activity. The promoter typically can also include elements that are responsive to transactivation, e.g., hypoxia response elements, Gal4 response elements, lac repressor response element, and small molecule control systems such as tet-regulated systems and the RU-486 system. See, e.g., Gossen et al. (1992) Proc. Natl. Acad. Sci USA 89:5547–5551; Oligino et al. (1998) Gene Ther. 5:491–496; Wang et al. (1997) Gene Ther. 4:432–441; Neering et al. (1996) Blood 88:1147–1155; and Rendahl et al. (1998) Nat. Biotechnol. 16:757–761.

In addition to a promoter, an expression vector typically contains a transcription unit or expression cassette that contains additional elements required for the expression of the nucleic acid in host cells, either prokaryotic or eukaryotic. A typical expression cassette thus contains a promoter operably linked, e.g., to the nucleic acid sequence, and signals required, e.g., for efficient polyadenylation of the transcript, transcriptional termination, ribosome binding, and/or translation termination. Additional elements of the cassette may include, e.g., enhancers, and heterologous spliced intronic signals.

The particular expression vector used to transport the genetic information into the cell is selected with regard to the intended use of the encoded polypeptide, e.g., expression in plants, animals, bacteria, fungi, protozoa etc. Standard bacterial expression vectors include plasmids such as pBR322, pBR322-based plasmids, pSKF, pET23D, and commercially available fusion expression systems such as GST and LacZ. Epitope tags can also be added to recombinant proteins to provide convenient methods of isolation, for monitoring expression, and for monitoring cellular and subcellular localization, e.g., hemagglutinin (HA), c-myc or FLAG.

Expression vectors containing regulatory elements from eukaryotic viruses are often used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the SV40 early promoter, SV40 late promoter, CMV promoter, metallothionein promoter, murine mammary tumor virus promoter, Rous sarcoma virus promoter, polyhedrin promoter, or other promoters shown effective for expression in eukaryotic cells.

Some expression systems have markers for selection of stably transfected cell lines such as thymidine kinase, hygromycin B phosphotransferase, and dihydrofolate reductase. High-yield expression systems are also suitable, such as baculovirus vectors in insect cells, with an inserted nucleic acid sequence under the transcriptional control of the polyhedrin promoter or any other strong baculovirus promoter.

Elements that are typically included in expression vectors also include a replicon that functions in *E. coli* (or in the prokaryotic host, if other than *E. coli*), a selective marker, e.g., a gene encoding antibiotic resistance, to permit selection of bacteria that harbor recombinant plasmids, and unique restriction sites in nonessential regions of the vector to allow insertion of recombinant sequences.

Standard transfection methods can be used to produce bacterial, mammalian, yeast, insect, or other cell lines that express large quantities of heterologous proteins, which can be purified, if desired, using standard techniques. See, e.g., Colley et al. (1989) *J. Biol. Chem.* 264:17619–17622; and *Guide to Protein Purification, in Methods in Enzymology*, vol. 182 (Deutscher, ed.) 1990. Transformation of eukaryotic and prokaryotic cells are performed according to standard techniques. See, e.g., Morrison (1977) *J. Bacteriol.* 132:349–351; Clark-Curtiss et al. (1983) in *Methods in Enzymology* 101:347–362 (Wu et al., eds).

Any procedure for introducing foreign nucleotide sequences into host cells can be used. These include, but are not limited to, the use of calcium phosphate transfection, DEAE-dextran-mediated transfection, polybrene, protoplast fusion, electroporation, lipid-mediated delivery (e.g., liposomes), microinjection, particle bombardment, introduction of naked DNA, plasmid vectors, viral vectors (both episomal and integrative) and any of the other well known methods for introducing cloned genomic DNA, cDNA, synthetic DNA or other foreign genetic material into a host cell (see, e.g., Sambrook et al, supra). It is only necessary that the particular genetic engineering procedure used be capable of successfully introducing at least one gene into the host cell capable of expressing the protein of choice.

Conventional viral and non-viral based gene transfer methods can be used to introduce nucleic acids into mammalian cells or target tissues. Such methods can be used to administer nucleic acids encoding fusion polypeptides to cells in vitro. Preferably, nucleic acids are administered for in vivo or ex vivo gene therapy uses. Non-viral vector delivery systems include DNA plasmids, naked nucleic acid, and nucleic acid complexed with a delivery vehicle such as a liposome. Viral vector delivery systems include DNA and RNA viruses, which have either episomal or integrated genomes after delivery to the cell. For reviews of gene therapy procedures, see, for example, Anderson (1992) *Science* 256:808–813; Nabel et al. (1993) *Trends Biotechnol.* 11:211–217; Mitani et al. (1993) *Trends Biotechnol.* 11:162–166; Dillon (1993) *Trends Biotechnol.* 11:167–175; Miller (1992) *Nature* 357:455–460; Van Brunt (1988) *Biotechnology* 6(10):1149–1154; Vigne (1995) *Restorative Neurology and Neuroscience* 8:35–36; Kremer et al. (1995) *British Medical Bulletin* 51(1):31–44; Haddada et al., in *Current Topics in Microbiology and Immunology*, Doerfler and Böhm (eds), 1995; and Yu et al. (1994) *Gene Therapy* 1:13-26.

Methods of non-viral delivery of nucleic acids include lipofection, microinjection, ballistics, virosomes, liposomes, immunoliposomes, polycation or lipid:nucleic acid conjugates, naked DNA, artificial virions, and agent-enhanced uptake of DNA. Lipofection is described in, e.g., U.S. Pat. Nos. 5,049,386; 4,946,787; and 4,897,355 and lipofection reagents are sold commercially (e.g., Transfectam™ and Lipofectin™). Cationic and neutral lipids that are suitable for efficient lipofection of polynucleotides include those of Felgner, WO 91/17424 and WO 91/16024. Nucleic acid can be delivered to cells (in vitro or ex vivo administration) or to target tissues (in vivo administration).

The preparation of lipid:nucleic acid complexes, including targeted liposomes such as immunolipid complexes, is well known to those of skill in the art. See, e.g., Crystal (1995) *Science* 270:404–410; Blaese et al. (1995) *Cancer Gene Ther.* 2:291–297; Behr et al. (1994) *Bioconjugate Chem.* 5:382–389; Remy et al. (1994) *Bioconjugate Chem.* 5:647–654; Gao et al. (1995) *Gene Therapy* 2:710–722; Ahmad et al. (1992) *Cancer Res.* 52:4817–4820; and U.S. Pat. Nos. 4,186,183; 4,217,344; 4,235,871; 4,261,975; 4,485,054; 4,501,728; 4,774,085; 4,837,028 and 4,946,787.

The use of RNA or DNA virus-based systems for the delivery of nucleic acids takes advantage of highly evolved processes for targeting a virus to specific cells in the body and trafficking the viral payload to the nucleus. Viral vectors can be administered directly to patients (in vivo) or they can be used to treat cells in vitro, wherein the modified cells are administered to patients (ex vivo). Conventional viral based systems for the delivery of nucleic acids include retroviral, lentiviral, poxviral, adenoviral, adeno-associated viral, vesicular stomatitis viral and herpesviral vectors. Integration in the host genome is possible with certain viral vectors, including the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, allowing alteration and/or expansion of the potential target cell population. Lentiviral vectors are retroviral vector that are able to transduce or infect non-dividing cells and typically produce high viral titers. Selection of a retroviral gene transfer system would therefore depend on the target tissue. Retroviral vectors have a packaging capacity of up to 6–10 kb of foreign sequence and are comprised of cis-acting long terminal repeats (LTRs). The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), simian immunodeficiency virus (SIV), human immunodeficiency virus (HIV), and combinations thereof. Buchscher et al. (1992) *J. Virol.* 66:2731–2739; Johann et al. (1992) *J. Virol.* 66:1635–1640; Sommerfelt et al. (1990) *Virol.* 176:58–59; Wilson et al. (1989) *J. Virol.* 63:2374–2378; Miller et al. (1991) *J. Virol.* 65:2220–2224; and PCT/US94/05700).

Adeno-associated virus (AAV) vectors are also used to transduce cells with target nucleic acids, e.g., in the in vitro production of nucleic acids and peptides, and for in vivo and ex vivo gene therapy procedures. See, e.g., West et al. (1987) *Virology* 160:38–47; U.S. Pat. No. 4,797,368; WO 93/24641; Kotin (1994) *Hum. Gene Ther.* 5:793–801; and Muzyczka (1994) *J. Clin. Invest.* 94:1351. Construction of recombinant AAV vectors are described in a number of publications, including U.S. Pat. No. 5,173,414; Tratschin et al. (1985) *Mol. Cell. Biol.* 5:3251–3260; Tratschin, et al (1984) *Mol. Cell. Biol.* 4:2072–2081; Hermonat et al. (1984) *Proc. Natl. Acad. Sci. USA* 81:6466–6470; and Samulski et al. (1989) *J. Virol.* 63:3822–3828.

Recombinant adeno-associated virus vectors based on the defective and nonpathogenic parvovirus adeno-associated virus type 2 (AAV-2) are a promising gene delivery system. Exemplary AAV vectors are derived from a plasmid containing the AAV 145 bp inverted terminal repeats flanking a transgene expression cassette. Efficient gene transfer and stable transgene delivery due to integration into the genomes of the transduced cell are key features for this vector system. Wagner et al. (1998) *Lancet* 351⊗(9117):1702–3; and Kearns et al. (1996) *Gene Ther.* 9:748–55.

pLASN and MFG-S are examples are retroviral vectors that have been used in clinical trials. Dunbar et al. (1995) *Blood* 85:3048–305; Kohn et al. (1995) *Nature Med.* 1:1017–102; Malech et al. (1997) *Proc. Natl. Acad. Sci. USA* 94:12133–12138. PA317/pLASN was the first therapeutic vector used in a gene therapy trial. (Blaese et al. (1995) *Science* 270:475–480. Transduction efficiencies of 50% or greater have been observed for MFG-S packaged vectors. Ellem et al. (1997) *Immunol Immunother.* 44(1):10–20; Dranoff et al. (1997) *Hum. Gene Ther.* 1:111–2.

In applications for which transient expression is preferred, adenoviral-based systems are useful. Adenoviral based vectors are capable of very high transduction efficiency in many cell types and are capable of infecting, and hence delivering nucleic acid to, both dividing and non-dividing cells. With such vectors, high titers and levels of expression have been obtained. Adenovirus vectors can be produced in large quantities in a relatively simple system.

Replication-deficient recombinant adenoviral (Ad) can be produced at high titer and they readily infect a number of different cell types. Most adenovirus vectors are engineered such that a transgene replaces the Ad E1a, E1b, and/or E3 genes; the replication defector vector is propagated in human 293 cells that supply the required E1 functions in trans. Ad vectors can transduce multiple types of tissues in vivo, including non-dividing, differentiated cells such as those found in the liver, kidney and muscle. Conventional Ad vectors have a large carrying capacity for inserted DNA. An example of the use of an Ad vector in a clinical trial involved polynucleotide therapy for antitumor immunization with intramuscular injection. Sterman et al. (1998) *Hum. Gene Ther.* 7:1083–1089. Additional examples of the use of adenovirus vectors for gene transfer in clinical trials include Rosenecker et al. (1996) *Infection* 24:5–10; Sterman et al., supra; Welsh et al. (1995) *Hum. Gene Ther.* 2:205–218; Alvarez et al. (1997) *Hum. Gene Ther.* 5:597–613; and Topf et al. (1998) *Gene Ther.* 5:507–513.

Packaging cells are used to form virus particles that are capable of infecting a host cell. Such cells include 293 cells, which package adenovirus, and Ψ2 cells or PA317 cells, which package retroviruses. Viral vectors used in gene therapy are usually generated by a producer cell line that packages a nucleic acid vector into a viral particle. The vectors typically contain the minimal viral sequences required for packaging and subsequent integration into a host, other viral sequences being replaced by an expression cassette for the protein to be expressed. Missing viral functions are supplied in trans, if necessary, by the packaging cell line. For example, AAV vectors used in gene therapy typically only possess ITR sequences from the AAV genome, which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment, which preferentially inactivates adenoviruses.

In many gene therapy applications, it is desirable that the gene therapy vector be delivered with a high degree of specificity to a particular tissue type. A viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al. (1995) *Proc. Natl. Acad. Sci. USA* 92:9747–9751 reported that Moloney murine leukemia virus can be modified to express human heregulin fused to gp70, and the recombinant virus infects certain human breast cancer cells expressing human epidermal growth factor receptor. This principle can be extended to other pairs of virus expressing a ligand fusion protein and target cell expressing a receptor. For example, filamentous phage can be engineered to display antibody fragments (e.g., $F_{ab}$ or $F_v$) having specific binding affinity for virtually any chosen cellular receptor. Although the above description applies primarily to viral vectors, the same principles can be applied to non-viral vectors. Such vectors can be engineered to contain specific uptake sequences thought to favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described infra. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Ex vivo cell transfection for diagnostics, research, or for gene therapy (e.g., via re-infusion of the transfected cells into the host organism) is well known to those of skill in the art. In a preferred embodiment, cells are isolated from the subject organism, transfected with a nucleic acid (gene or cDNA), and re-infused back into the subject organism (e.g., patient). Various cell types suitable for ex vivo transfection are well known to those of skill in the art. See, e.g., Freshney et al., *Culture of Animal Cells, A Manual of Basic Technique*, 3rd ed., 1994, and references cited therein, for a discussion of isolation and culture of cells from patients.

In one embodiment, hematopoietic stem cells are used in ex vivo procedures for cell transfection and gene therapy. The advantage to using stem cells is that they can be differentiated into other cell types in vitro, or can be introduced into a mammal (such as the donor of the cells) where they will engraft in the bone marrow. Methods for differentiating CD34+ stem cells in vitro into clinically important immune cell types using cytokines such a GM-CSF, IFN-γ and TNF-α are known. Inaba et al. (1992) *J. Exp. Med.* 176:1693–1702.

Stem cells are isolated for transduction and differentiation using known methods. For example, stem cells are isolated from bone marrow cells by panning the bone marrow cells with antibodies which bind unwanted cells, such as CD4+ and CD8+ (T cells), CD45+ (panB cells), GR-1 (granulocytes), and Iad (differentiated antigen presenting cells). See Inaba et al., supra.

Vectors (e.g., retroviruses, adenoviruses, liposomes, etc.) containing therapeutic nucleic acids can be also administered directly to the organism for transduction of cells in vivo. Alternatively, naked DNA can be administered. Administration is by any of the routes normally used for introducing a molecule into ultimate contact with blood or tissue cells. Suitable methods of administering such nucleic acids are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions, as described below. See, e.g., *Remington's Pharmaceutical Sciences*, 17th ed., 1989.

B. Delivery of Polypeptides

In other embodiments, for example in certain in vitro situations, target cells are cultured in a medium containing localization domain fusion polypeptides or functional fragments thereof.

An important factor in the administration of polypeptide compounds is ensuring that the polypeptide has the ability to traverse the plasma membrane of a cell, or the membrane of an intracellular compartment such as the nucleus. Cellular membranes are composed of lipid-protein bilayers that are freely permeable to small, nonionic lipophilic compounds and are inherently impermeable to polar compounds, macromolecules, and therapeutic or diagnostic agents. However, proteins, lipids and other compounds, which have the ability to translocate polypeptides across a cell membrane, have been described.

For example, "membrane translocation polypeptides" have amphiphilic or hydrophobic amino acid subsequences that have the ability to act as membrane-translocating carriers. In one embodiment, homeodomain proteins have the ability to translocate across cell membranes. The shortest internalizable peptide of a homeodomain protein, Antennapedia, was found to be the third helix of the protein, from amino acid position 43 to 58. Prochiantz (1996) *Curr. Opin. Neurobiol.* 6:629–634. Another subsequence, the h (hydrophobic) domain of signal peptides, was found to have similar cell membrane translocation characteristics. Lin et al. (1995) *J. Biol. Chem.* 270:14255–14258.

Examples of peptide sequences which can be linked to a polypeptide for facilitating its uptake into cells include, but are not limited to: an 11 amino acid peptide of the tat protein of HIV; a 20 residue peptide sequence which corresponds to amino acids 84–103 of the p16 protein (see Fahraeus et al. (1996) *Curr. Biol.* 6:84); the third helix of the 60-amino acid long homeodomain of Antennapedia (Derossi et al. (1994) *J. Biol. Chem.* 269:10444); the h region of a signal peptide, such as the Kaposi fibroblast growth factor (K-FGF) h region (Lin et al., supra); and the VP22 translocation domain from HSV (Elliot et al. (1997) *Cell* 88:223–233). Other suitable chemical moieties that provide enhanced cellular uptake can also be linked, either covalently or non-covalently, to the fusion polypeptides disclosed herein.

Toxin molecules also have the ability to transport polypeptides across cell membranes. Often, such molecules (called "binary toxins") are composed of at least two parts: a translocation or binding domain and a separate toxin domain. Typically, the translocation domain, which can optionally be a polypeptide, binds to a cellular receptor, facilitating transport of the toxin into the cell. Several bacterial toxins, including *Clostridium perfringens* iota toxin, diphtheria toxin (DT), *Pseudomonas* exotoxin A (PE), pertussis toxin (PT), *Bacillus anthracis* toxin, and pertussis adenylate cyclase (CYA), have been used to deliver peptides to the cell cytosol as internal or amino-terminal fusions. Arora et al. (1993) *J. Biol. Chem.* 268:3334–3341; Perelle et al. (1993) *Infect. Immun.* 61:5147–5156; Stenmark et al. (1991) *J. Cell Biol.* 113:1025–1032; Donnelly et al. (1993) *Proc. Natl. Acad. Sci. USA* 90:3530–3534; Carbonetti et al. (1995) *Abstr. Annu. Meet. Am. Soc. Microbiol.* 95:295; Sebo et al. (1995) *Infect. Immun.* 63:3851–3857; Klimpel et al. (1992) *Proc. Natl. Acad. Sci. USA.* 89:10277–10281; and Novak et al. (1992) *J. Biol. Chem.* 267:17186–17193.

Such subsequences can be used to translocate polypeptides, including the fusion polypeptides disclosed herein, across a cell membrane. This is accomplished, for example, by derivatizing the fusion polypeptide with one of these translocation sequences, or by forming an additional fusion of the translocation sequence with the fusion polypeptide. Optionally, a linker can be used to link the fusion polypeptide and the translocation sequence. Any suitable linker can be used, e.g., a peptide linker.

A suitable polypeptide can also be introduced into an animal cell, preferably a mammalian cell, via liposomes and liposome derivatives such as immunoliposomes. The term "liposome" refers to vesicles comprised of one or more concentrically ordered lipid bilayers, which encapsulate an aqueous phase. The aqueous phase typically contains the compound to be delivered to the cell.

The liposome fuses with the plasma membrane, thereby releasing the compound into the cytosol. Alternatively, the liposome is phagocytosed or taken up by the cell in a transport vesicle. Once in the endosome or phagosome, the liposome is either degraded or it fuses with the membrane of the transport vesicle and releases its contents.

In current methods of drug delivery via liposomes, the liposome ultimately becomes permeable and releases the encapsulated compound at the target tissue or cell. For systemic or tissue specific delivery, this can be accomplished, for example, in a passive manner wherein the liposome bilayer is degraded over time through the action of various agents in the body. Alternatively, active drug release involves using an agent to induce a permeability change in the liposome vesicle. Liposome membranes can be constructed so that they become destabilized when the environment becomes acidic near the liposome membrane. See, e.g., *Proc. Natl. Acad. Sci. USA* 84:7851 (1987); *Biochemistry* 28:908 (1989). When liposomes are endocytosed by a target cell, for example, they become destabilized and release their contents. This destabilization is termed fusogenesis. Dioleoylphosphatidylethanolamine (DOPE) is the basis of many "fusogenic" systems.

For use with the methods and compositions disclosed herein, liposomes typically comprise a fusion polypeptide as disclosed herein, a lipid component, e.g., a neutral and/or cationic lipid, and optionally include a receptor-recognition molecule such as an antibody that binds to a predetermined cell surface receptor or ligand (e.g., an antigen). A variety of methods are available for preparing liposomes as described in, e.g.; U.S. Pat. Nos. 4,186,183; 4,217,344; 4,235,871; 4,261,975; 4,485,054; 4,501,728; 4,774,085; 4,837,028; 4,235,871; 4,261,975; 4,485,054; 4,501,728; 4,774,085; 4,837,028; 4,946,787; PCT Publication No. WO 91/17424; Szoka et al. (1980) *Ann. Rev. Biophys. Bioeng.* 9:467; Deamer et al. (1976) *Biochim. Biophys. Acta* 443:629–634; Fraley, et al. (1979) *Proc. Natl. Acad. Sci. USA* 76:3348–3352; Hope et al. (1985) *Biochim. Biophys. Acta* 812:55–65; Mayer et al. (1986) *Biochim. Biophys. Acta* 858:161–168; Williams et al. (1988) *Proc. Natl. Acad. Sci. USA* 85:242–246; *Liposomes, Ostro* (ed.), 1983, Chapter 1); Hope et al. (1986) *Chem. Phys. Lip.* 40:89; Gregoriadis, *Liposome Technology* (1984) and Lasic, *Liposomes: from Physics to Applications* (1993). Suitable methods include, for example, sonication, extrusion, high pressure/homogenization, microfluidization, detergent dialysis, calcium-induced fusion of small liposome vesicles and ether-fusion methods, all of which are well known in the art.

In certain embodiments, it may be desirable to target a liposome using targeting moieties that are specific to a particular cell type, tissue, and the like. Targeting of liposomes using a variety of targeting moieties (e.g., ligands, receptors, and monoclonal antibodies) has been previously described. See, e.g., U.S. Pat. Nos. 4,957,773 and 4,603,044.

Examples of targeting moieties include monoclonal antibodies specific to antigens associated with neoplasms, such as prostate cancer specific antigen and MAGE. Tumors can also be diagnosed by detecting gene products resulting from the activation or over-expression of oncogenes, such as ras or c-erbB2. In addition, many tumors express antigens normally expressed by fetal tissue, such as the alphafetoprotein (AFP) and carcinoembryonic antigen (CEA). Sites of viral infection can be diagnosed using various viral antigens such as hepatitis B core and surface antigens (HBVc, HBVs) hepatitis C antigens, Epstein-Barr virus antigens, human immunodeficiency type-1 virus (HIV-1) and papilloma virus antigens. Inflammation can be detected using molecules specifically recognized by surface molecules which are expressed at sites of inflammation such as integrins (e.g., VCAM-1), selectin receptors (e.g., ELAM-1) and the like.

Standard methods for coupling targeting agents to liposomes are used. These methods generally involve the incorporation into liposomes of lipid components, e.g., phosphatidylethanolamine, which can be activated for attachment of targeting agents, or incorporation of derivatized lipophilic compounds, such as lipid derivatized bleomycin. Antibody targeted liposomes can be constructed using, for instance, liposomes which incorporate protein A. See Renneisen et al. (1990) *J. Biol. Chem.* 265:16337–16342 and Leonetti et al. (1990) *Proc. Natl. Acad. Sci. USA* 87:2448–2451.

Pharmaceutical Compositions and Administration

Fusion molecules as disclosed herein, and expression vectors encoding these polypeptides, can be used in conjunction with various methods of gene therapy to facilitate the action of a therapeutic gene product. In such applications, the fusion molecule can be administered directly to a patient, e.g., to facilitate the modulation of gene expression and for therapeutic or prophylactic applications, for example, cancer, ischemia, diabetic retinopathy, macular degeneration, rheumatoid arthritis, psoriasis, HIV infection, sickle cell anemia, Alzheimer's disease, muscular dystrophy, neurodegenerative diseases, vascular disease, cystic fibrosis, stroke, and the like. Examples of microorganisms whose inhibition can be facilitated through use of the methods and compositions disclosed herein include pathogenic bacteria, e.g., *Chlamydia, Rickettsial* bacteria, *Mycobacteria, Staphylococci, Streptococci, Pneumococci, Meningococci* and *Conococci, Klebsiella, Proteus, Serratia, Pseudomonas, Legionella, Diphtheria, Salmonella, Bacilli* (e.g., anthrax), *Vibrio* (e.g., cholera), *Clostridium* (e.g., tetanus, botulism), *Yersinia* (e.g., plague), *Leptospirosis,* and *Borrellia* (e.g., Lyme disease bacteria); infectious fungus, e.g., *Aspergillus, Candida* species; protozoa such as sporozoa (e.g., *Plasmodia*), rhizopods (e.g., *Entamoeba*) and flagellates (*Trypanosoma, Leishmania, Trichomonas, Giardia,* etc.); viruses, e.g., hepatitis (A, B, or C), herpes viruses (e.g., VZV, HSV-1, HHV-6, HSV-11, CMV, and EBV), HIV, Ebola, Marburg and related hemorrhagic fever-causing viruses, adenoviruses, influenza viruses, flaviviruses, echoviruses, rhinoviruses, coxsackie viruses, cornaviruses, respiratory syncytial viruses, mumps viruses, rotaviruses, measles viruses, rubella viruses, parvoviruses, vaccinia viruses, HTLV viruses, retroviruses, lentiviruses, dengue viruses, papillomaviruses, polioviruses, rabies viruses, and arboviral encephalitis viruses, etc.

Administration of therapeutically effective amounts of a localization domain-DNA-binding domain fusion molecule, a localization domain-DNA-binding domain-regulatory doomain fusion or a nucleic acid encoding these fusion polypeptides is by any of the routes normally used for introducing polypeptides or nucleic acids into ultimate contact with the tissue to be treated. The polypeptides or nucleic acids are administered in any suitable manner, preferably in a pharmaceutically acceptable carrier. Suitable methods of administering such modulators are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions. See, e.g., *Remington's Pharmaceutical Sciences,* 17th ed. 1985.

Fusion polypeptides or nucleic acids, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intravenous, intramuscular, intradermal, intracardiac and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Compositions can be administered, for example, by intravenous infusion, orally, topically, intraperitoneally, intrapluerally, intravesically or intrathecally. The formulations of compounds can be presented in unit-dose or multi-dose sealed containers, such as ampoules and vials. Injection solutions and suspensions can be prepared from sterile powders, granules, and tablets of the kind known to those of skill in the art.

Applications

The compositions and methods disclosed herein can be used to modulate a number of cellular processes. These include, but are not limited to, transcription, replication, recombination, repair, integration, maintenance of telomeres, and processes involved in chromosome stability and disjunction. Accordingly, the methods and compositions disclosed herein can be used to affect any of these processes, as well as any other process which are influenced by localization domain fusion molecules and their effects on gene expression, intranuclear localization and chromatin structure.

In preferred embodiments, a localization domain/DNA-binding domain fusion is used to achieve targeted repression of gene expression. Targeting is based upon the specificity of the DNA-binding domain. In another embodiment, a localization domain/DNA-binding domain/transcriptional activation domain fusion is used to achieve reactivation of a developmentally-silenced gene. In additional embodiments a localization domain/DNA-binding domain/chromatin remodeling complex component fusion is used to remodel the chromatin structure of a repressed gene located in a heterochromatic nuclear compartment, to allow access of transcriptional activators, either endogenous or exogenous. In these embodiments, additional molecules, exogenous and/or endogenous, can be used to facilitate repression or activation of gene expression. The additional molecules can also be fusion molecules, for example, fusions between a DNA-binding domain and a functional domain such as an activation or repression domain or a component of a chromatin remodeling complex.

Accordingly, expression of any gene in any organism can be modulated using the methods and compositions disclosed herein, including therapeutically relevant genes, genes of infecting microorganisms, viral genes, and genes whose expression is modulated in the process of target validation. Such genes include, but are not limited to, vascular endothelial growth factor (VEGF), VEGF receptors flt and flk, CCR-5, low density lipoprotein receptor (LDLR), estrogen receptor, HER-2/neu, BRCA-1, BRCA-2, phosphoenolpyruvate carboxykinase (PEPCK), CYP7, fibrinogen, apolipoprotein A (ApoA), apolipoprotein B (ApoB), renin, phosphoenolpyruvate carboxykinase (PEPCK), CYP7, fibrinogen, nuclear factor κB (NF-κB), inhibitor of NF-κB (I-κB), tumor necrosis factors (e.g., TNF-α, TNF-β), interleukin-1 (IL-1), FAS (CD95), FAS ligand (CD95L), atrial natriuretic factor, platelet-derived factor (PDF), amyloid precursor protein (APP), tyrosinase, tyrosine hydroxylase, β-aspartyl hydroxylase, alkaline phosphatase, calpains (e.g., CAPN10) neuronal pentraxin receptor, adriamycin response protein, apolipoprotein E (apoE), leptin, leptin receptor, UCP-1, IL-1, IL-1 receptor, IL-2, IL-3, IL-4, IL-5, IL-6, IL-12, IL-15, interleukin receptors, G-CSF, GM-CSF, colony stimulating factor, erythropoietin (EPO), platelet-derived growth factor (PDGF), PDGF receptor, fibroblast growth factor (FGF), FGF receptor, PAF, p16, p19, p53, Rb, p21, myc, myb, globin, dystrophin, eutrophin, cystic fibrosis transmembrane conductance regulator (CFTR), GNDF, nerve growth factor (NGF), NGF receptor, epidermal growth factor (EGF), EGF receptor, transforming growth factors (e.g., TGF-α, TGF-β), fibroblast growth factor (FGF), interferons (e.g., IFN-α, IFN-β and IFN-γ), insulin-related growth factor-1 (IGF-1), angiostatin, ICAM-1, signal transducer and activator of transcription (STAT), androgen receptors, e-cadherin, cathepsins (e.g., cathepsin W), topoisomerase, telomerase, bcl, bcl-2, Bax, T Cell-specific tyrosine kinase (Lck), p38 mitogen-activated protein kinase, protein tyrosine phosphatase (hPTP), adenylate cyclase, guanylate cyclase, α7 neuronal nicotinic acetylcholine receptor, 5-hydroxytryptamine (serotonin)-2A receptor, transcription elongation factor-3 (TEF-3), phosphatidylcholine transferase, ftz, PTI-1, polygalacturonase, EPSP synthase, FAD2–1, Δ-9 desaturase, Δ-12 desaturase, Δ-15 desaturase, acetyl-Coenzyme A carboxylase, acyl-ACP thioesterase, ADP-glucose pyrophosphorylase, starch synthase, cellulose synthase, sucrose synthase, fatty acid hydroperoxide lyase, and peroxisome proliferator-activated receptors, such as PPAR-γ2. See also *Science* 291:1177–1351 (2001) and *Nature* 409:813–958 (2001).

Expression of human, mammalian, bacterial, fungal, protozoal, Archaeal, plant and viral genes can be modulated. Viral genes include, but are not limited to, hepatitis virus genes such as, for example, HBV-C, HBV-S, HBV-X and HBV-P; and HIV genes such as, for example, tat and rev. Modulation of expression of genes encoding antigens of a pathogenic organism can be achieved using the disclosed methods and compositions.

Additional genes include those encoding cytokines, lymphokines, interleukins, growth factors, mitogenic factors, apoptotic factors, cytochromes, chemotactic factors, chemokine receptors (e.g., CCR-2, CCR-3, CCR-5, CXCR-4), phospholipases (e.g., phospholipase C), nuclear receptors, retinoid receptors, organellar receptors, hormones, hormone receptors, oncogenes, tumor suppressors, cyclins, cell cycle checkpoint proteins (e.g., Chk1, Chk2), senescence-associated genes, immunoglobulins, genes encoding heavy metal chelators, protein tyrosine kinases, protein tyrosine phosphatases, tumor necrosis factor receptor-associated factors (e.g., Traf-3, Traf-6), apolipoproteins, thrombic factors, vasoactive factors, neuroreceptors, cell surface receptors, G-proteins, G-protein-coupled receptors (e.g., substance K receptor, angiotensin receptor, α- and β-adrenergic receptors, serotonin receptors, and PAF receptor), muscarinic receptors, acetylcholine receptors, GABA receptors, glutamate receptors, dopamine receptors, adhesion proteins (e.g., CAMs, selectins, integrins and immunoglobulin superfamily members), ion channels, receptor-associated factors, hematopoietic factors, transcription factors, and molecules involved in signal transduction. Expression of disease-related genes, and/or of one or more genes specific to a particular tissue or cell type such as, for example, brain, muscle, heart, nervous system, circulatory system, reproductive system, genitourinary system, digestive system and respiratory system can also be modulated.

Thus, the methods and compositions disclosed herein can be used in processes such as, for example, therapeutic regulation of disease-related genes, engineering of cells for manufacture of protein pharmaceuticals, pharmaceutical discovery (including target discovery, target validation and engineering of cells for high throughput screening methods) and plant agriculture.

EXAMPLES

The following examples are presented as illustrative of, but not limiting, the claimed subject matter.

Example 1

Materials and Methods

Cloning of dMBD-Like and dMBD-LikeΔ dMBD-likeΔ was obtained as an EST clone (LD03777, 23) and the coding sequence amplified and cloned using a T/A cloning kit (Invitrogen) according to the manufacturer's directions. DNA sequencing confirmed the fidelity of amplification and the coding sequence was then subcloned into pET-21a(+) (Novagen) using the NheI-XhoI sites.

dMBD-like expression clones were prepared by RT-PCR from total Drosophila RNA using the following primer pair:

```
MBDf:
5'-GGAATTGGGAATTGCGCTAGCATGAACCCGAGCG  (SEQ ID NO:2)
                   TCACAATC-3';

MBDr:
5'-GCGAATTCTGTCTTGAGTGCATCCTGCAGCTTTC  (SEQ ID NO:3)
                   GCGCAACTCCG-3'.
```

PCR products were isolated on agarose gels, excised, reamplified and cloned into the EcoRI-NheI sites of pTYB1 (NEB). Fidelity of reverse transcription and amplification was verified by DNA sequencing.

Purification of Recombinant Protein

Recombinant dMBD-likeΔ was expressed in E. coli BL21 (DE3). 500 ml of LB were inoculated with 5 ml of an overnight culture and incubated at 37° C. to $A_{600}$ of 0.7. Induction was performed by addition of isopropyl β-thiogalactosidase to 1 mM and incubation at 37° C. for 3 additional hours. Cells were harvested and resuspended in 10 ml of sonication buffer (20 mM Tris-HCl pH 8.0, 500 mM NaCl, 5 mM imidazole, 0.1% Nonidet-P-40 (NP-40), 1 mM 2-mercaptoethanol). Purification of the soluble His-tagged protein was performed with TALON resin (Clontech) according to the manufacturer's protocol. Protein was dialyzed versus 20 mM Tris-HCl, pH 8.0, 500 mM NaCl, 1 mM 2-mercaptoethanol, 2 mM $MgCl_2$. Quantitation was performed using the BioRad protein assay. Recombinant dMBD-like was prepared using the Impact CN System (New England Biolabs) according to the manufacturer's protocol.

Gel Mobility-shift and Southwestern Assays

Gel mobility shifts were performed in 10% polyacrylamide gels run in 0.5×TBE buffer (45 mM Tris, pH 8.0, 45 mM boric acid, 1 mM EDTA) using GAC12 or GAM12 double-stranded oligonucleotide probes, essentially as described in Wade et al. (1999) Nature Genet. 23:62–66. One picomole of radiolabelled probe was mixed with purified recombinant protein as indicated in the figure legends in 10 mM Tris HCl pH 8.0, 3 mM $MgCl_2$, 50 mM NaCl, 0.1 mM EDTA, 0.1% NP-40, 2 mM DTT, 5% glycerol and 0.4 mg/ml BSA. The samples were incubated for 30 min at 37° C. 30 pmoles of competitor DNA (GAC12 or GAM12) were used per binding reaction. Gels were scanned on a Phosphormager (Molecular Dynamics). The procedure used for southwestern assays is as described in Wade et al. (1999), supra.

Antibodies, Immunoblots and Immunoprecipitations

Protein samples were resolved by SDS-PAGE and transferred to Immobilon-P membrane (Millipore) following the manufacturer's recommendations. The Drosophila MBD-like antibodies were elicited in rabbits by subcutaneous injection of recombinant dMBD-likeΔ by Covance Laboratories, Inc. For immunoprecipitations, antibodies were immobilized on Protein A beads (Pierce) and subsequently incubated with 100 μg nuclear extract, or 100 μg of the BioRex 0.5 M fraction for 2 h at 4° C. with rotation. The beads were washed three times with Buffer C (0.1 M NaCl, see below) and analyzed by histone deacetylase or ATPase assays. NP-40 (0.01%) was included in all buffers.

Histone Deacetylase and ATPase Assays

Chicken histone octamers (20.25 nmoles) were acetylated using recombinant yeast HAT1p and $^3$H-acetyl CoA (5.3 nm) followed by a cold Acetyl-CoA (100 nm) chase for complete acetylation. Deacetylation of the samples was carried out in a reaction (200 μl) containing 25 mM Tris pH 8.0, 50 mM NaCl, 1 mM EDTA, 10% glycerol, and 1 μg $^3$H-histone octamer substrate. Reactions were incubated for 30 min at 30° C., were terminated by adding 50 μl stop solution (0.1 M HCl and 0.16 M HAc), and extracted with 600 μl ethyl acetate. 450 μl of the organic layer was counted in a liquid scintillation counter. Released acetate is indicated in the figures as cpm.

In an ATPase assay, samples were incubated with γ-$[^{32}P]$ ATP in the absence or presence of chicken erythrocyte mononucleosomes for 30 min at room temperature. Reactions were spotted on PEI-cellulose thin-layer chromatography plates and developed in 1 M formic acid and 0.5 M LiCl. ATP hydrolysis was quantitated using a PhosphorImager (Molecular Dynamics) with Image Quant Software.

Fractionation of dMBD-like-containing Complexes

S2 cells were grown in suspension culture in Grace's Insect media supplemented with 10% heat-treated fetal bovine serum (FBS). Cells were centrifuged at 5,000 rpm for 10 min. The pellet was resuspended in 40 ml of Buffer A (10 mM Hepes pH 7.5, 15 mM KCl, 2 mM $MgCl_2$, 0.1 mM EDTA, 1 mM DTT, 0.5 mM PMSF) and 2.7 ml of Buffer B (50 mM Hepes pH 7.5, 1 M KCl, 30 mM $MgCl_2$, 0.1 mM EDTA, 1 mM DTT, 0.5 mM PMSF) and centrifuged at 5,000 rpm for 10 min. The pellet was resuspended in 10 ml of Buffer A and re-centrifuged as above. Cells were resuspended in 20 ml of Buffer A and homogenized with a Dounce homogenizer. 1.5 ml of Buffer B were added and the mixture was again homogenized for a few additional strokes. The homogenate was centrifuged at 8,000 rpm for 8 min. Nuclei were resuspended in 20 ml of buffer A and homogenized with 6–8 strokes. 2 ml of 4 M $(NH_4)_2SO4$ were added. The suspension was rotated for 30 min and centrifuged at 10,000 rpm for 30 min. The supernatant was dialyzed versus Buffer C (100 mM KCl, 20 mM Hepes pH 7.5, 1 mM EGTA, 1.5 mM $MgCl_2$, 1 mM PMSF, 0.5 mM DTT, 10% glycerol) and cleared in a SW50.1 rotor at 40,000 rpm for 60 minutes.

The dialyzed extract was loaded onto a BioRex70 (Na$^+$) (BioRad) column equilibrated with Buffer C at 10 mg protein per ml packed bed volume (cv), washed with 3 cv Buffer C (0.1 M), and step eluted with Buffer C (0.5 M). The 0.5 M fraction containing all the detectable dMBD-likeΔ was fractionated over MonoQ HR5/5 (Pharmacia Biotech) in a 20 cv linear gradient from Buffer C (0.1 M) to Buffer C (1 M) and collected in 0.5 ml fractions. All fractions were analyzed by immunoblot and histone-deacetylase assay. The fraction containing the peak of dMBD-likeΔ was dialyzed, centrifuged, and fractionated on a Superose6 HR10/30 gel filtration column (Pharmacia Biotech). All fractions were analyzed by immunoblotting and HDAC assay. Antisera to Mi-2 and Mta1 were described elsewhere (Wade et al., 1999, supra) as were SIN3 and RPD3 antisera.

Northern Blot Analysis

RNA was prepared from staged embryos, larvae, or adult flies using the Trizol reagent (Life Technologies) according to the manufacturer's directions. 10 μg total RNA was loaded per lane, resolved on 1.2% agarose gels containing formaldehyde, transferred to nylon, and hybridized with a random-primed probe corresponding to the coding sequence of dMBD-likeΔ.

Cotransfection Assays

Drosophila S2 cells were grown in Schneider's medium (Sigma) at 27° C. containing 10% FBS and penicillin/streptomycin. Cells were transfected using the Superfect reagent (Qiagen) following the manufacturer's directions. Transfection assays included 1.5 μg of either the pG$_5$DE$_5$tkLuc reporter or the p-37tkRLuc internal control, essentially as described in Chen et al. (1998) Mol Cell Biol 18:7259–7268. The Gal4 DNA binding domain constructs, pACTIN-SV-Gal4-Gro, pACTIN-SV-Gal4-MBD and pACTIN-SV-Gal4-MBDΔ were constructed by insertion of the Gal4 DBD into the HindIII/PstI sites of pACTIN-SV followed by insertion of Gro, dMBD-like and dMBD-likeΔ into the EcoRI site of the resulting plasmid. Quantities of individual Gal4 plasmids were varied as described in the figure legends. The total amount of plasmid was normalized to 4 μg by addition of pACTIN-SV vector (Huynh et al. (1999) J. Mol Biol 288:13–20) as carrier. Cells were harvested 12 h after transfection and luciferase assays were performed using an Enhanced Luciferase Assay Kit (Pharmingen) according to the manufacturer's instructions. Where indicated, transfected cells were treated with Trichostatin A (TSA, Wako) for 24 h before harvest.

Polytene Chromosome Staining

Polytene chromosome squashes and staining were performed on Canton-S flies as described in Zink and Paro (1989) Nature 337:468–471 and Westwood (1991) Nature 353:822–827. Briefly, salivary glands were dissected in PBS and were placed directly in fixative containing 3.7% formaldehyde, 45% acetic acid for 1 min prior to squashing. The spreads were stained with α-dMBD-like (1:200) followed by Alexa 594-conjugated donkey α-goat IgG (1:400) (Molecular Probes). DNA was visualized with 4,6-diamidino-2-phenylindole (DAPI; 1:1000). Control spreads stained with pre-immune serum, at an equivalent concentration to that indicated above, showed no staining. Each staining experiment was performed multiple times.

Example 2

Identification of a Drosophila MBD Family

A search for Drosophila sequences similar to vertebrate methyl CpG binding proteins (MBD's) yielded multiple candidates (FIG. 1A). The Drosophila proteins are similar to vertebrate MBD proteins only in the putative methyl CpG binding domain with the exception of dMBD-like. The solution structure of this motif has been solved for MeCP2 (Wakefield et al. (1999) J Mol Biol 291:1055–1065) and for MBD1 (Ohki et al. (1999) EMBO J. 18:6653–6661). It consists of a wedge-shaped structure composed of four antiparallel β-strands on one face and an α-helix and hairpin loop on the other (Rubin et al. (2000) Science 287:2204–2215).

The sequences of the putative Drosophila MBD proteins were compared with those of their vertebrate counterparts, focusing on residues critical to the structure of the methyl CpG binding domain. Two uncharacterized products of the Drosophila genome project, CG10042 and CG12196 (Adams et al. (2000) Science 287:2185–2195), and the product of the six-banded gene (sba, Zeidler et al (1997) Biol Chem. 378:1119–1124) contain most of these sequence features. Specifically, the regions corresponding to the four beta strands are well conserved, including hydrophobic residues (FIG. 1A) proposed to be crucial for integrity of the fold (Ohki et al., supra). There is some variation in the number of amino acids between loop L2 and the hairpin loop, although the vertebrate MBD family members also differ in this aspect. Basic residues that constitute a charged surface on one side of the vertebrate MBD structures are also well conserved (FIG. 1A). Finally, two hydrophobic residues critical to the structure of the hairpin loop are also present. An important difference between the Drosophila and vertebrate proteins occurs in the loop L1, located between β-strands two and three (FIG. 1A). In vertebrate methyl CpG binding proteins, the spacing between strands β2 and β3 is invariant and the amino acid side chains in this loop are very similar. In contrast, the Drosophila proteins have variations both in length and in side chain chemistry in this loop (FIG. 1A). This region of MBD1 and MeCP2 undergoes a conformational change upon binding to methylated DNA and is implicated as crucial for protein-DNA interaction. It seems likely that alterations in this region of the protein will abolish methyl CpG binding activity.

Drosophila MBD-like (dMBD-like) was previously identified as a sequence relative of vertebrate MBD2 and MBD3 (Zhang et al. (1999) Genes Dev 13:1924–1935; Tweedie et al. (1999) Nature Genet 23:329–390). It is similar to MBD2 and MBD3 throughout its length (FIG. 1B) and is encoded by a single gene (Flybase ID FBgn0027950, 1). Two mRNAs are generated from this locus, one of 1115 bases, a second of 842 bases (Rubin et al. (2000) Science 287:2222–2224). The protein products of these alternatively spliced mRNAs differ in the amino acids encoded by exon 2 (FIG. 1B).

The two methyl CpG binding domain protein homologs were named dMBD-like (product of the 1115 base mRNA) and dMBD-likeΔ (product of the 842 base mRNA). Both dMBD-like isoforms share extensive sequence similarity with the recently described forms of MBD3 from Xenopus (Wade et al. (1999) Nature Genet 23:62–66), particularly the third exon of the Drosophila gene (FIG. 1B). However, there are several gaps and non-conserved amino acids in the region corresponding to the MBD (FIG. 1B). The two dMBD-like proteins have an opa-like repeat (Wharton et al. (1985) Cell 40:55–62) inserted in the loop between strands β2 and β3 (FIG. 1B)—this region is predicted to interact with DNA (Wakefield et al. (1999) J Mol Biol 291:1055–1065). In addition, dMBD-like lacks the distal portion of the α-helix making up one face of the wedge (FIG. 1B). The shorter isoform, dMBD-likeΔ, completely lacks the fourth β-strand, the α-helix, and the hairpin loop. Finally, there are numerous amino acid changes at positions predicted to be crucial for DNA interaction and structural integrity of the domain. Thus, it seemed unlikely that either protein would bind methylated DNA.

Example 3 dMBD-like Fails to Bind Methylated DNA

The two dMBD-like proteins were expressed in bacteria, purified, and their binding properties were compared to Xenopus MBD3, a protein previously demonstrated to bind selectively to methylated DNA (Wade et al. (1999), supra). In Southwestern assays using immobilized protein, neither isoform interacted with the probes, regardless of methylation status (FIG. 1C). Thus, either the proteins fail to bind or they are unable to refold on the membrane surface.

Solution interactions with DNA were also examined using an electrophoretic mobility shift assay (FIG. 1D). Neither of the *Drosophila* proteins bound, under conditions where *Xenopus* MBD3 bound methylated DNA selectively. In fact, no binding was observed for the dMBD-like isoforms even after reducing the concentrations of cold competitor DNA up to 50 fold, resulting in a mass excess of radiolabelled probe over cold competitor (see Example 1). No interaction was detected under these conditions, even non-specific aggregation. Therefore, the results indicate that neither dMBD-like isoform binds DNA, in keeping with the lack of genome-wide methylation in *Drosophila*.

Example 4 dMBD-likeΔ Associates with HDAC and Nucleosome-stimulated ATPase Activities

The sequence similarity between exon three of dMBD-like and vertebrate MBD2 and MBD3 (Yao et al. (1993) *Nature* 366:476–479) implies conservation of function. One potential role for this region is interaction with other proteins. As *Drosophila* contains homologs of many proteins known to be components of HDAC-containing corepressor complexes in other systems (Rubin et al. (2000) *Science* 287:2204–2215 and Adams et al. (2000) *Science* 287:2185–2195), the presence of dMBD-like as a component of such a complex (or complexes) in *Drosophila* was examined.

α-dMBD-like polyclonal antisera were used to investigate potential interactions between dMBD-like and known components of corepressor complexes. Immunoblot analysis confirmed that the antisera recognized both isoforms of dMBD-like (FIG. 2A). Interestingly, only the shorter isoform, dMBD-likeΔ, was detected in nuclear extracts from S2 cells (FIG. 2A). Immunoprecipitations were then performed from S2 nuclear extracts and the precipitated proteins were assayed for enzymatic activities associated with corepressor complexes. Immune serum, but not preimmune serum, efficiently precipitated histone deacetylase activity (FIG. 2B) and also precipitated ATPase activity (FIG. 2C). Like vertebrate and Drosophila Mi-2 (Chen et al. (1999) *Genes Devel.* 13:2218–2230; Guschin et al. (2000) *Biochemistry* 39:5238–5245) the precipitated ATPase activity was stimulated by nucleosomes (FIG. 2C). These results indicate that MBD-likeΔ is associated with an undefined histone deacetylase and a nucleosome-stimulated ATPase in S2 nuclei, suggesting inclusion of dMBD-likeΔ in a Drosophila Mi-2-like corepressor complex.

The relationship of dMBD-likeΔ with other proteins in S2 cells using classical biochemical techniques was also examined. Nuclear extracts were fractionated using ion exchange and gel filtration chromatography; dMBD-likeΔ was assayed in the fractions by immunoblot. All the detectable dMBD-likeΔ bound the BioRex 70 column and was eluted at 0.5 M NaCl. Gradient elution of the BioRex 70 pool on MonoQ yielded a major peak of deacetylase activity, precisely coeluting with SIN3 and RPD3 (FIG. 3A). The peak of dMBD-likeΔ by immunoblot was resolved from the peaks of HDAC activity, RPD3, and SIN3 by a single fraction (FIG. 3A). The peak fraction of dMBD-likeΔ from the MonoQ column was further purified using a Superose 6 gel filtration column. The peaks of dMBD-likeΔ, Mi-2, and MTA1-like (Wade et al. (1999) *Nature Genet.* 23:62–66) coeluted at a position consistent with a molecular mass of approximately 1 MDa (FIG. 3B). SIN3, RPD3, and p55 (Zeidler et al., supra; Martinez-Balbas et al. (1998) *Proc. Natl. Acad. Sci. USA* 95:132–137), the Drosophila RbA p48/p46 homolog, also closely, but not precisely, coeluted. Thus, dMBD-likeΔ copurifies with Mi-2 and MTA1-like, consistent with its inclusion in a Drosophila Mi-2 complex similar to that observed in vertebrates.

Example 5 dMBD-like Represses Transcription when Tethered Near a Promoter

A transcription assay, essentially as described in Chen et al. (1999) *Genes Devel* 13:2218–2230 and Chen et al. (1998) *Mol Cell Biol* 18:7259–7268, was used to assess the consequences of tethering the dMBD-like isoforms at a promoter. Both dMBD-like and dMBD-likeΔ were filsed to the Gal4 DNA binding domain (DBD). A Gal4-Groucho fusion (see, Chen et al (1998) and Chen et al. (1999), both supra) and the Gal4 DBD were used as positive and negative controls for transcriptional repression, respectively (FIG. 4A). Gal4 fusions to dMBD-like, dMBD-likeΔ and Groucho mediated dose-dependent transcriptional repression following transfection into S2 cells (FIG. 4B). Control experiments showed that repression required a Gal4 site in the reporter plasmid (FIG. 4B, lower) and that transfection of dMBD-like or dMBD-likeΔ lacking the Gal4 DBD failed to repress transcription. The expression levels of the transfected Gal4 fusion proteins were equivalent by immunoblot (FIG. 4C). Further, the repression seen with the two tethered dMBD-like isoforms was similar to that observed with the well-characterized repressor Groucho (FIG. 4B).

If dMBD-like represses transcription through recruitment of a Drosophila Mi-2 complex, transcriptional repression should be sensitive to inhibitors of histone deacetylases. Accordingly, the effect of Trichostatin-A, a histone deacetylase inhibitor, on dMBD-like-mediated repression was tested. Repression mediated by tethering of dMBD-like or dMBD-likeΔ was largely relieved by Trichostatin-A (TSA); this effect was qualitatively very similar to that of TSA on Groucho-mediated repression (FIG. 4D).

In sum, the results indicate that both isoforms of dMBD-like function as transcriptional corepressors through recruitment of histone deacetylase activity, consistent with the proposed function of the Drosophila Mi-2 complex.

Example 6

Developmental Expression Profile of dMBD-like

Northern analysis was used to ascertain the expression patterns of the two dMBD-like isoforms during Drosophila development (FIG. 5). Two transcripts, corresponding to the splice variants of dMBD-like, were present in early embryos (FIG. 5A). Interestingly, the 0–2 hour embryos had only the longer mRNA. Levels of this mRNA decline precipitously after 12 hours of embryonic development and remain undetectable in larval stages and adult males; however this mRNA is present in adult females, possibly due to maternal mRNA in the ovary. Protein expression patterns partially mimic the mRNA expression data (FIG. 5B). Again, only dMBD-like was observed in 0–2 hour embryos while both dMBD-like and dMBD-likeΔ were present in 12–24 hour embryos. In the final embryonic stage and in the first larval stage, only the dMBD-likeΔ isoform was present. Neither protein isoform was detectable in the remaining larval stages or in adults, despite the presence of their mRNAs (FIG. 5A).

Example 7 dMBD-like Associates with Heterochromatin and a Small Number of Euchromatic Sites in Polytene Chromosomes To investigate target gene specificity of dMBD-like, its distribution on Drosophila salivary gland polytene chromosomes from third instar larvae was examined. Polytene chromosomes are ideal for this analysis since they are thought to reflect the biochemical and structural properties of chromatin of diploid interphase cells and their large size allows for the identification of individual chromosomal sites (Hill et al. (1987) *Int Rev Cytol* 108:61–118). At this developmental stage, only the shorter mRNA was detected, corresponding to dMBD-likeΔ (see Example 6).

To visualize the banding pattern of the polytene chromosomes, the chromosomes were counterstained with DAPI, which stains brightest in the condensed, banded regions of euchromatin and the constitutively condensed heterochromatin at the chromocenter. Immunofluorescence staining with the antibody to dMBD-like revealed preferential association with 29 euchromatic sites as well as weaker association with ~100 euchromatic sites and centric heterochromatin. In addition to localization to a set of discrete sites within the euchromatic chromosome arms, dMBD-likeΔ is present at the chromocenter, a region of constitutive heterochromatin. No staining was observed with preimmune sera or at the hunchback-regulated Ubx locus. Interestingly, 69% of the predominant sites correspond to developmental puffs that are transcriptionally induced by pulses of the steroid hormone 20-hydroxyecdysone (ecdysone) during the late larval and prepupal periods (Ashburner et al. (1972) *Results Probl Cell Differ* 4:101–151).

These binding studies indicate that dMBD-likeΔ is a component of an Mi-2 complex in flies and not a component of a SIN3 containing complex. Further, the Mi-2 complex in flies appears to have a role in either establishment or maintenance of heterochromatin.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. A method of compartmentalizing a region of interest in cellular chromatin, the method comprising contacting the region of interest with a composition that binds to a binding site in cellular chromatin, wherein the binding site is in a gene of interest and wherein the composition comprises:
   (a) a localization domain wherein the localization domain is a chromodomain or is a localization domain from a protein selected from the group consisting of methylated DNA-binding proteins (MBDs), DNA-N-methyl transferases (dNMTs) and MBD-like proteins, and
   (b) a DNA binding domain that is heterologous to the localization domain, or functional fragment thereof.

2. The method of claim 1, wherein the composition is a fusion molecule.

3. The method of claim 1, wherein the DNA binding domain comprises a zinc finger DNA-binding domain.

4. The method of claim 1, wherein the region of interest is compartmentalized into a nuclear compartment for packaging as heterochromatin.

5. The method of claim 1, wherein the cellular chromatin is present in a plant cell.

6. The method of claim 1, wherein the cellular chromatin is present in an animal cell.

7. The method of claim 6, wherein the cell is a human cell.

8. The method of claim 1, wherein the localization domain is a methyl CpU binding domain.

9. The method of claim 1, wherein the protein is selected from the group consisting of dMBD-like and dMBD-likeΔ.

10. The method of claim 1, wherein the DNA-binding domain comprises a triplex-forming nucleic acid or a minor groove binder.

11. The method of claim 1, wherein compartmentalization facilitates modulation of expression of a gene associated with the region of interest.

12. The method of claim 11, wherein compartmentalization facilitates repression of expression of a gene associated with the region of interest.

13. The method of claim 2, wherein the fusion molecule is a polypeptide.

14. The method of claim 13, wherein the method further comprises the step of contacting a cell with a polynucleotide encoding the polypeptide, wherein the polypeptide is expressed in the cell.

15. The method of claim 1, wherein the gene encodes a product selected from the group consisting of vascular endothelial growth factor, erythropoietin, androgen receptor, PPAR-γ2, p16, p53, pRb, dystrophin and e-cadherin.

16. The method of claim 8, wherein the methyl CpG binding domain is from a gene involved in a disease state selected from the group consisting of ICF syndrome, Rett syndrome and Fragile X syndrome.

17. A method of modulating expression of a gene, the method comprising the step of contacting a region of DNA in cellular chromatin with a fusion molecule that binds to a binding site in cellular chromatin, wherein the binding site is in the gene and wherein the fusion molecule comprises:
   (a) a DNA binding domain or functional fragment thereof and
   (b) a localization domain wherein the localization domain is a chromodomain or is a localization domain from a protein selected from the group consisting of methylated DNA-binding proteins (MBDs), DNA-N-methyl transferases (dNMTs) and MBD-like proteins and wherein the DNA binding domain is heterologous to the localization domain.

18. The method of claim 17, wherein modulation comprises repression of expression of the gene.

19. The method of claim 17, wherein the DNA-binding domain of the fusion molecule comprises a zinc finger DNA-binding domain.

20. The method of claim 17, wherein the DNA binding domain binds to a target site in a gene encoding a product selected from the group consisting of vascular endothelial growth factor, erythropoietin, androgen receptor, PPAR-γ2, p16, p53, pRb, dystrophin and e-cadherin.

21. The method of claim 17, wherein the localization domain is a methyl CpG binding domain.

22. The method of claim 17, wherein the protein is selected from the group consisting of dMBD-like and dMBD-likeΔ.

23. The method of claim 17, wherein the gene is in a plant cell.

24. The method of claim 17, wherein the gene is in an animal cell.

25. The method of claim 24, wherein the cell is a human cell.

26. The method of claim 17, wherein the fusion molecule is a polypeptide.

27. The method of claim 26, wherein the method further comprises the step of contacting a cell with a polynucleotide encoding the polypeptide, wherein the polypeptide is expressed in the cell.

28. The method of claim 17, wherein a plurality of fusion molecules is contacted with cellular chromatin, wherein each of the fusion molecules binds to a distinct binding site.

29. The method of claim 28, wherein at least one of the fusion molecules comprises a zinc finger DNA-binding domain.

30. The method of claim 28, wherein the expression of a plurality of genes is modulated.

31. The method of claim 1, wherein the protein is HP1.

32. The method of claim 17, wherein the protein is HP1.

* * * * *

SEQUENCE LISTING

```
<160> NUMBER OF SEQ ID NOS: 17

<210> SEQ ID NO 1
<211> LENGTH: 23
<212> TYPE: PRT
<213> ORGANISM: Artificial Sequence
<220> FEATURE:
<223> OTHER INFORMATION: Description of Artificial Sequence:   segment
      from Drosophila MBD-like sequence

<400> SEQUENCE: 1

Asn Asn Asn Ala Ser Ser Asn Asn Asn Ser Ser Ala Thr Ala Ser Ser
 1               5                  10                  15

Asn Asn Asn Asn Asn Lys Val
            20

<210> SEQ ID NO 2
<211> LENGTH: 42
<212> TYPE: DNA
<213> ORGANISM: Artificial Sequence
<220> FEATURE:
<223> OTHER INFORMATION: Description of Artificial Sequence:   MBDf

<400> SEQUENCE: 2
ggaattggga attgcgctag catgaacccg agcgtcacaa tc                           42

<210> SEQ ID NO 3
<211> LENGTH: 45
<212> TYPE: DNA
<213> ORGANISM: Artificial Sequence
<220> FEATURE:
<223> OTHER INFORMATION: Description of Artificial Sequence:   MBDr

<400> SEQUENCE: 3
gcgaattctg tcttgagtgc atcctgcagc tttcgcgcaa ctccg                        45

<210> SEQ ID NO 4
<211> LENGTH: 25
<212> TYPE: PRT
<213> ORGANISM: Artificial Sequence
<220> FEATURE:
<223> OTHER INFORMATION: Description of Artificial Sequence:   exemplary
      motif characterizing C2H2 class proteins
<220> FEATURE:
```

```
<221> NAME/KEY: MOD_RES
<222> LOCATION: (2)..(3)
<223> OTHER INFORMATION: Xaa = any amino acid
<220> FEATURE:
<221> NAME/KEY: MOD_RES
<222> LOCATION: (4)..(5)
<223> OTHER INFORMATION: Xaa = any amino acid, may be present or absent
<220> FEATURE:
<221> NAME/KEY: MOD_RES
<222> LOCATION: (7)..(18)
<223> OTHER INFORMATION: Xaa = any amino acid
<220> FEATURE:
<221> NAME/KEY: MOD_RES
<222> LOCATION: (20)..(22)
<223> OTHER INFORMATION: Xaa = any amino acid
<220> FEATURE:
<221> NAME/KEY: MOD_RES
<222> LOCATION: (23)..(24)
<223> OTHER INFORMATION: Xaa = any amino acid, may be present or absent

<400> SEQUENCE: 4

Cys Xaa Xaa Xaa Xaa Cys Xaa Xaa Xaa Xaa Xaa Xaa Xaa Xaa Xaa
 1               5                  10                  15

Xaa Xaa His Xaa Xaa Xaa Xaa Xaa His
            20                  25

<210> SEQ ID NO 5
<211> LENGTH: 68
<212> TYPE: PRT
<213> ORGANISM: Artificial Sequence
<220> FEATURE:
<223> OTHER INFORMATION: Description of Artificial Sequence:  MeCP2

<400> SEQUENCE: 5

Tyr Asp Asp Pro Thr Leu Pro Glu Gly Trp Thr Arg Lys Leu Lys Gln
 1               5                  10                  15

Arg Lys Ser Gly Arg Ser Ala Gly Lys Tyr Asp Val Tyr Leu Ile Asn
            20                  25                  30

Pro Gln Gly Lys Ala Phe Arg Ser Lys Val Glu Leu Ile Ala Tyr Phe
        35                  40                  45

Glu Lys Val Gly Asp Thr Ser Leu Asp Pro Asn Asp Phe Asp Phe Thr
    50                  55                  60

Val Thr Gly Arg
 65

<210> SEQ ID NO 6
<211> LENGTH: 64
<212> TYPE: PRT
<213> ORGANISM: Artificial Sequence
<220> FEATURE:
<223> OTHER INFORMATION: Description of Artificial Sequence:  MBD1

<400> SEQUENCE: 6

Leu Asp Cys Pro Ala Leu Gly Pro Gly Trp Lys Arg Arg Glu Val Phe
 1               5                  10                  15

Arg Lys Ser Gly Ala Thr Cys Gly Arg Ser Asp Thr Tyr Tyr Gln Ser
            20                  25                  30

Pro Thr Gly Asp Arg Ile Arg Ser Lys Val Glu Leu Thr Arg Tyr Leu
        35                  40                  45

Gly Pro Ala Cys Asp Leu Thr Leu Phe Asp Phe Lys Gln Gly Ile Leu
    50                  55                  60

<210> SEQ ID NO 7
<211> LENGTH: 68
<212> TYPE: PRT
```

```
<213> ORGANISM: Artificial Sequence
<220> FEATURE:
<223> OTHER INFORMATION: Description of Artificial Sequence:  MBD4

<400> SEQUENCE: 7

Glu Cys Arg Lys Ser Val Pro Cys Gly Trp Glu Arg Val Val Lys Gln
 1               5                  10                  15

Arg Leu Phe Gly Lys Thr Ala Gly Arg Phe Asp Val Tyr Phe Tyr Ser
            20                  25                  30

Pro Gln Gly Leu Lys Phe Arg Ser Lys Ser Ser Leu Ala Asn Tyr Leu
        35                  40                  45

His Lys Asn Gly Glu Thr Ser Leu Lys Pro Glu Asp Phe Asp Phe Thr
    50                  55                  60

Val Leu Ser Lys
 65

<210> SEQ ID NO 8
<211> LENGTH: 64
<212> TYPE: PRT
<213> ORGANISM: Artificial Sequence
<220> FEATURE:
<223> OTHER INFORMATION: Description of Artificial Sequence:  MBD2

<400> SEQUENCE: 8

Met Asp Cys Pro Ala Leu Pro Pro Gly Trp Lys Lys Glu Glu Val Ile
 1               5                  10                  15

Arg Lys Ser Gly Leu Ser Ala Gly Lys Ser Asp Val Tyr Tyr Phe Ser
            20                  25                  30

Pro Ser Gly Lys Lys Phe Arg Ser Lys Pro Gln Leu Ala Arg Tyr Leu
        35                  40                  45

Gly Asn Thr Val Asp Leu Ser Ser Phe Asp Phe Arg Thr Gly Lys Met
    50                  55                  60

<210> SEQ ID NO 9
<211> LENGTH: 63
<212> TYPE: PRT
<213> ORGANISM: Artificial Sequence
<220> FEATURE:
<223> OTHER INFORMATION: Description of Artificial Sequence:  xMBD3

<400> SEQUENCE: 9

Trp Glu Cys Ser Ala Leu Gln Gly Trp Lys Lys Glu Glu Val Thr Arg
 1               5                  10                  15

Arg Ser Gly Leu Ser Ala Gly Lys Ser Asp Val Tyr Tyr Phe Ser Pro
            20                  25                  30

Ser Gly Lys Lys Phe Arg Ser Lys Pro Gln Leu Ala Arg Tyr Leu Gly
        35                  40                  45

Asn Ser Met Asp Leu Ser Thr Phe Asp Phe Arg Thr Gly Lys Met
    50                  55                  60

<210> SEQ ID NO 10
<211> LENGTH: 65
<212> TYPE: PRT
<213> ORGANISM: Artificial Sequence
<220> FEATURE:
<223> OTHER INFORMATION: Description of Artificial Sequence:  CG10042

<400> SEQUENCE: 10

Val Gln Asp Trp Phe Leu Pro Pro Gly Trp Ile Lys His Met Tyr Gln
 1               5                  10                  15

Arg Ser Asn Val Leu Gly Lys Trp Asp Val Ile Leu Val Ser Pro Ser
```

```
                    20                  25                  30

Gly Lys Arg Phe Arg Ser Lys Ser Asp Leu Lys Leu Phe Leu Glu Ser
         35                  40                  45

Gln Asn Leu Val Tyr Asn Pro Asp Val Tyr Asp Tyr Met Glu Ala Pro
     50                  55                  60

Val
 65

<210> SEQ ID NO 11
<211> LENGTH: 62
<212> TYPE: PRT
<213> ORGANISM: Artificial Sequence
<220> FEATURE:
<223> OTHER INFORMATION: Description of Artificial Sequence:  CG12196

<400> SEQUENCE: 11

Pro Leu Ala Lys Pro Leu Leu Ser Gly Trp Glu Arg Leu Val Met Arg
 1               5                  10                  15

Gln Lys Thr Lys Lys Ser Val Val Tyr Lys Gly Pro Cys Gly Lys Ser
                20                  25                  30

Leu Arg Ser Leu Ala Glu Val His Arg Tyr Leu Arg Ala Thr Glu Asn
         35                  40                  45

Val Leu Asn Val Asp Asn Phe Asp Phe Thr Pro Asp Leu Lys
     50                  55                  60

<210> SEQ ID NO 12
<211> LENGTH: 66
<212> TYPE: PRT
<213> ORGANISM: Artificial Sequence
<220> FEATURE:
<223> OTHER INFORMATION: Description of Artificial Sequence:  sba

<400> SEQUENCE: 12

Ser Tyr Asn Gly Asn Leu Ala Pro Gly Trp Arg Arg Leu Thr Asn Asn
 1               5                  10                  15

Asn Glu Val Ala Tyr Ile Ser Pro Ser Gly Lys Thr Leu Arg Thr Gln
                20                  25                  30

Phe Gln Ile Lys Asp Tyr Leu Leu Thr Gln Gly Thr Cys Lys Cys Gly
         35                  40                  45

Leu Pro Leu Pro Leu Arg Pro Glu Tyr Leu Phe Asp Phe Asn Ala Gln
     50                  55                  60

Val Pro
 65

<210> SEQ ID NO 13
<211> LENGTH: 51
<212> TYPE: PRT
<213> ORGANISM: Artificial Sequence
<220> FEATURE:
<223> OTHER INFORMATION: Description of Artificial Sequence:  dMBD-like

<400> SEQUENCE: 13

Val Asp Cys Ser Val Leu Pro Lys Gly Trp Gln Arg Asp Glu Val Arg
 1               5                  10                  15

Lys Ser Gly Ser Ser Ala Asp Val Phe Tyr Tyr Ser Pro Thr Gly Lys
                20                  25                  30

Arg Ala Glu Gly Lys Pro Gln Asp Ile Ala Ile Pro Asp Phe Gln Pro
         35                  40                  45

Gly Lys Met
     50
```

-continued

<210> SEQ ID NO 14
<211> LENGTH: 339
<212> TYPE: PRT
<213> ORGANISM: Artificial Sequence
<220> FEATURE:
<223> OTHER INFORMATION: Description of Artificial Sequence: Drosophila
      MBD-like

<400> SEQUENCE: 14

Met Gln Met Asn Pro Ser Val Thr Ile Glu Arg Lys Arg Val Asp Cys
 1               5                  10                  15

Ser Val Leu Pro Lys Gly Trp Gln Arg Asp Glu Val Arg Lys Ser Gly
                20                  25                  30

Ser Ser Ala Asn Asn Ala Ser Ser Asn Asn Asn Ser Ser Ala Thr
            35                  40                  45

Ala Ser Ser Asn Asn Asn Asn Lys Val Asp Val Phe Tyr Tyr Ser
        50                  55                  60

Pro Thr Gly Lys Arg Ala Glu Gly Lys Pro Gln Asp Ile Ala Ile Pro
 65                  70                  75                  80

Asp Phe Gln Pro Gly Lys Met Pro His Cys Ala Leu Pro Ser Pro Ser
                85                  90                  95

Ile Ser Leu Tyr Arg Cys Ser Ala Met Pro Leu Pro Ile Ala Ser Gly
                100                 105                 110

Gly Gly Asn Gly Ala Thr Ser Gly Ser Ala Ala Asn Ala Leu Lys Arg
            115                 120                 125

Lys Phe Ala Arg Ser Gln Gly Gly Asn Ala Ala Gly Ala Ala Gly Ala
        130                 135                 140

Ala Pro Pro Ala Ala Thr Ala Ser Ser Ala Ala Thr Ala Thr Ala Ala
145                 150                 155                 160

Ser Ala Ser Pro Ser Thr Ala Asn Arg Gln Gln Gln Ile Glu Leu
                165                 170                 175

Ser Arg Ala Leu Arg Thr Asp Val Ser Leu Val Pro Pro Ile Arg Gln
            180                 185                 190

Thr Ala Ser Ile Phe Lys Gln Pro Val Thr Val Ile Arg Asn His Lys
        195                 200                 205

Gln Asp Pro Ala Lys Ala Lys Asn Glu Pro Lys His Gly Thr Arg Glu
    210                 215                 220

Lys Pro Lys Gln Leu Phe Trp Glu Lys Arg Leu Glu Arg Leu Arg Ala
225                 230                 235                 240

Cys His Asp Ser Gly Glu Glu Leu Asp Ile Ser Leu Pro Lys Thr
                245                 250                 255

Ile Arg Thr Val Gly Pro Asn Val Asn Glu Gln Thr Val Leu Gln Ser
            260                 265                 270

Val Ala Thr Ala Leu His Met Leu Asn Ala Gly Val His Gly Gln Ser
        275                 280                 285

Ser Thr Lys Ala Asp Leu Thr Lys Asn Ala Met Ala Phe Met Asn Pro
    290                 295                 300

Glu Gln Pro Leu Met His Ala Val Ile Ile Ser Glu Asp Asp Ile Arg
305                 310                 315                 320

Lys Gln Glu Asp Arg Val Gly Val Ala Arg Arg Lys Leu Gln Asp Ala
                325                 330                 335

Leu Lys Thr

<210> SEQ ID NO 15

```
<211> LENGTH: 226
<212> TYPE: PRT
<213> ORGANISM: Artificial Sequence
<220> FEATURE:
<223> OTHER INFORMATION: Description of Artificial Sequence: Drosophila
      MBD-like delta

<400> SEQUENCE: 15
```

Met Gln Met Asn Pro Ser Val Thr Ile Glu Arg Lys Arg Val Asp Cys
1               5                   10                  15

Ser Val Leu Pro Lys Gly Trp Gln Arg Asp Glu Val Arg Lys Ser Gly
            20                  25                  30

Ser Ser Ala Asn Asn Asn Ala Ser Asn Asn Asn Ser Ala Thr
        35                  40                  45

Ala Ser Asn Asn Asn Asn Lys Val Asp Val Phe Tyr Tyr Ser
    50                  55                  60

Arg Ala Leu Arg Thr Asp Val Ser Leu Val Pro Pro Ile Arg Gln Thr
65                  70                  75                  80

Ala Ser Ile Phe Lys Gln Pro Val Thr Val Ile Arg Asn His Lys Gln
                85                  90                  95

Asp Pro Ala Lys Ala Lys Asn Glu Pro Lys His Gly Thr Arg Glu Lys
            100                 105                 110

Pro Lys Gln Leu Phe Trp Glu Lys Arg Leu Glu Arg Leu Arg Ala Cys
        115                 120                 125

His Asp Ser Gly Glu Glu Leu Asp Asp Ile Ser Leu Pro Lys Thr Ile
    130                 135                 140

Arg Thr Val Gly Pro Asn Val Asn Glu Gln Thr Val Leu Gln Ser Val
145                 150                 155                 160

Ala Thr Ala Leu His Met Leu Asn Ala Gly Val His Gly Gln Ser Ser
                165                 170                 175

Thr Lys Ala Asp Leu Thr Lys Asn Ala Met Ala Phe Met Asn Pro Glu
            180                 185                 190

Gln Pro Leu Met His Ala Val Ile Ile Ser Glu Asp Asp Ile Arg Lys
        195                 200                 205

Gln Glu Asp Arg Val Gly Val Ala Arg Arg Lys Leu Gln Asp Ala Leu
    210                 215                 220

Lys Thr
225

```
<210> SEQ ID NO 16
<211> LENGTH: 303
<212> TYPE: PRT
<213> ORGANISM: Artificial Sequence
<220> FEATURE:
<223> OTHER INFORMATION: Description of Artificial Sequence: X. laevis
      MBD3 LF

<400> SEQUENCE: 16
```

Met Glu Lys Lys Arg Trp Glu Cys Ser Ala Leu Pro Gln Gly Trp Lys
1               5                   10                  15

Lys Glu Glu Val Thr Arg Arg Ser Gly Leu Ser Ala Gly Lys Ser Asp
            20                  25                  30

Val Tyr Tyr Tyr Ser Ser Pro Ser Arg Tyr Asn Arg Ser Leu Arg
        35                  40                  45

Asp Arg Val Gly Cys Leu Asn Ile Asn Pro Ser Gly Lys Lys Phe Arg
    50                  55                  60

Ser Lys Pro Gln Leu Ala Arg Tyr Leu Gly Asn Ser Met Asp Leu Ser
65                  70                  75                  80

```
Thr Phe Asp Phe Arg Thr Gly Lys Met Leu Met Ser Lys Ile Asn Lys
                85                  90                  95
Asn Arg Gln Arg Met Arg Tyr Asp Gly Leu Asn Gln Ser Lys Gly Lys
            100                 105                 110
Pro Asp Leu Asn Thr Ala Leu Pro Val Arg Gln Thr Ala Ser Ile Phe
        115                 120                 125
Lys Gln Pro Val Thr Lys Val Thr Asn His Pro Thr Asn Lys Val Lys
    130                 135                 140
Ser Asp Pro Gln Lys Ala Val Asp Gln Pro Arg Gln Leu Phe Trp Glu
145                 150                 155                 160
Lys Lys Leu Ser Gly Leu Asn Ala Phe Asp Ile Ala Glu Glu Leu Val
                165                 170                 175
Lys Thr Met Glu Leu Pro Lys Gly Leu Gln Gly Val Gly Pro Gly Cys
            180                 185                 190
Thr Asp Glu Thr Leu Leu Ser Ala Ile Ala Ser Ala Leu His Thr Ser
        195                 200                 205
Thr Met Pro Ile Thr Gly Gln Leu Ser Ala Ala Val Glu Lys Asn Pro
    210                 215                 220
Gly Val Trp Leu Asn Thr Ser Gln Pro Leu Cys Lys Ala Phe Met Val
225                 230                 235                 240
Thr Asp Glu Asp Ile Arg Lys Gln Glu Glu Leu Val Gln Gln Val Arg
                245                 250                 255
Lys Lys Leu Glu Glu Ala Leu Met Ala Asp Met Leu Ala His Val Glu
            260                 265                 270
Glu Ile Ser Lys Asp Gly Gly Ala Pro Leu Asp Lys Asp Ile Asp Asp
        275                 280                 285
Glu Glu Glu Asp Gln Asp Pro Arg Glu Gln Glu Ala Asp Asp Val
    290                 295                 300

<210> SEQ ID NO 17
<211> LENGTH: 282
<212> TYPE: PRT
<213> ORGANISM: Artificial Sequence
<220> FEATURE:
<223> OTHER INFORMATION: Description of Artificial Sequence:  X. laevis
      MBD3

<400> SEQUENCE: 17

Met Glu Lys Lys Arg Trp Glu Cys Ser Ala Leu Gln Gly Trp Lys Lys
1               5                   10                  15
Glu Glu Val Thr Arg Arg Ser Gly Leu Ser Ala Gly Lys Ser Asp Val
            20                  25                  30
Tyr Tyr Tyr Ser Pro Ser Gly Lys Lys Phe Arg Ser Lys Pro Gln Leu
        35                  40                  45
Ala Arg Tyr Leu Gly Asn Ser Met Asp Leu Ser Thr Phe Asp Phe Arg
    50                  55                  60
Thr Gly Lys Met Leu Met Ser Lys Ile Asn Lys Asn Arg Gln Arg Met
65                  70                  75                  80
Arg Tyr Asp Gly Leu Asn Gln Ser Lys Gly Lys Pro Asp Leu Asn Thr
                85                  90                  95
Ala Leu Pro Val Arg Gln Thr Ala Ser Ile Phe Lys Gln Pro Val Thr
            100                 105                 110
Lys Val Thr Asn His Pro Thr Asn Lys Val Lys Ser Asp Pro Gln Lys
        115                 120                 125
Ala Val Asp Gln Pro Arg Gln Leu Phe Trp Glu Lys Lys Leu Ser Gly
```

-continued

```
              130                 135                 140
Leu Asn Ala Phe Asp Ile Ala Glu Glu Leu Val Lys Thr Met Glu Leu
145                 150                 155                 160

Pro Lys Gly Leu Gln Gly Val Gly Pro Gly Cys Thr Asp Glu Thr Leu
                165                 170                 175

Leu Ser Ala Ile Ala Ser Ala Leu His Thr Ser Thr Met Pro Ile Thr
                180                 185                 190

Gly Gln Leu Ser Ala Ala Val Glu Lys Asn Pro Gly Val Trp Leu Asn
            195                 200                 205

Thr Ser Gln Pro Leu Cys Lys Ala Phe Met Val Thr Asp Glu Asp Ile
        210                 215                 220

Arg Lys Gln Glu Glu Leu Val Gln Gln Val Arg Lys Lys Leu Glu Glu
225                 230                 235                 240

Ala Leu Met Ala Asp Met Leu Ala His Val Glu Glu Ile Ser Lys Asp
                245                 250                 255

Gly Gly Ala Pro Leu Asp Lys Asp Ile Asp Asp Glu Glu Glu Asp Gln
                260                 265                 270

Asp Pro Arg Glu Gln Glu Ala Asp Asp Val
            275                 280
```